United States Patent
Qiao et al.

(10) Patent No.: US 11,154,589 B2
(45) Date of Patent: Oct. 26, 2021

(54) ANTIMICROBIAL COMPOSITION COMBINATIONS COMPRISING STAR SHAPED PEPTIDE POLYMERS

(71) Applicant: The University of Melbourne, Melbourne (AU)

(72) Inventors: Greg GuangHua Qiao, Melbourne (AU); Neil Martin O'Brien-Simpson, Melbourne (AU); Shu Jie Lam, Melbourne (AU); Eric Charles Reynolds, Melbourne (AU)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 16/343,556

(22) PCT Filed: Nov. 2, 2017

(86) PCT No.: PCT/AU2017/051206
§ 371 (c)(1),
(2) Date: Apr. 19, 2019

(87) PCT Pub. No.: WO2018/081861
PCT Pub. Date: May 11, 2018

(65) Prior Publication Data
US 2019/0247459 A1    Aug. 15, 2019

(30) Foreign Application Priority Data
Nov. 2, 2016    (AU) ................................ 2016904472

(51) Int. Cl.
| | | |
|---|---|---|
| *A61K 38/16* | (2006.01) | |
| *A61P 31/04* | (2006.01) | |
| *A61K 38/12* | (2006.01) | |
| *A61K 38/14* | (2006.01) | |
| *A61K 38/02* | (2006.01) | |
| *A61K 31/7056* | (2006.01) | |
| *A61K 31/635* | (2006.01) | |
| *A61K 31/43* | (2006.01) | |
| *A61K 31/7052* | (2006.01) | |
| *A61K 31/437* | (2006.01) | |
| *A61K 31/422* | (2006.01) | |
| *A61K 31/546* | (2006.01) | |
| *A61K 31/496* | (2006.01) | |
| *A61K 31/7048* | (2006.01) | |
| *A61K 31/7036* | (2006.01) | |
| *A61K 31/4375* | (2006.01) | |
| *A61K 31/407* | (2006.01) | |
| *A61K 31/65* | (2006.01) | |

(52) U.S. Cl.
CPC ............ *A61K 38/16* (2013.01); *A61K 31/407* (2013.01); *A61K 31/422* (2013.01); *A61K 31/43* (2013.01); *A61K 31/437* (2013.01); *A61K 31/4375* (2013.01); *A61K 31/496* (2013.01); *A61K 31/546* (2013.01); *A61K 31/635* (2013.01); *A61K 31/65* (2013.01); *A61K 31/7036* (2013.01); *A61K 31/7048* (2013.01); *A61K 31/7052* (2013.01); *A61K 31/7056* (2013.01); *A61K 38/02* (2013.01); *A61K 38/12* (2013.01); *A61K 38/14* (2013.01); *A61P 31/04* (2018.01)

(58) Field of Classification Search
None
See application file for complete search history.

(56) References Cited

U.S. PATENT DOCUMENTS

2020/0123328 A1    4/2020    Qiao et al.

FOREIGN PATENT DOCUMENTS

| WO | WO 2000/015240 | 3/2000 |
| WO | WO 2014/165923 | 10/2014 |
| WO | WO 2015/144928 | 10/2015 |

OTHER PUBLICATIONS

Fishbain, Treatment of Acinetobacter Infectionsm Reviews of Anti-infective Agents, CID, 2010, pp. 79-83 (Year: 2010).*
Gao et al., "Synthesis and Mechanism Insight of a Peptide-Grafted Hyperbranched Polymer Nanosheet with Weak Positive Charges but Excellent Intrinsically Antibacterial Efficacy," Biomacromolecules, Jun. 13, 2016;17:2080-6.
Lam et al., "Combating multidrug-resistant Gram-negative bacteria with structurally nanoengineered antimicrobial peptide polymers," Nat Microbiol., Sep. 12, 2016;1(11):16162.
Lam et al., "SNAPPing Gram-negative bacteria with star-shaped polypeptides," Abstracts of Papers, 250th ACS National Meeting & Exposition, Boston, MA, U.S., Aug. 16-20, 2015, pmse-370.
Stach et al., "Combining topology and sequence design for the discovery of potent antimicrobial peptide dendrimers against multidrug-resistant Pseudomonas aeruginosa," Angew Chem Int Ed Engl., Nov. 17, 2014;53:12827-31.
Stach et al., "Membrane disrupting antimicrobial peptide dendrimers with multiple amino termini," Med. Chem. Commun., 2012;3:86-89.

(Continued)

*Primary Examiner* — Thomas S Heard
(74) *Attorney, Agent, or Firm* — Fish & Richardson P.C.

(57) ABSTRACT

This invention relates to compositions including antibacterial compounds. The invention also relates to the use of the compositions in methods of treating bacterial infections. In one aspect the present invention also provides a method of increasing the susceptibility of bacteria to the anti-bacterial activity of a compound, the method comprising contacting the bacteria with a star shaped peptide polymer of the invention, thereby increasing the susceptibility of the bacteria to the anti-bacterial activity of the compound. Preferably, the method further includes the step of contacting the bacteria with the compound for which the bacteria have increased susceptibility to. The invention is further relates to the combination of a star shaped peptide polymer and an anti-bacterial compound that restore the sensitivity of antibiotic resistant bacteria to antibiotics that are otherwise ineffective when administered alone.

26 Claims, 20 Drawing Sheets

(56) References Cited

OTHER PUBLICATIONS

International Search Report and Written Opinion for App. No. PCT/AU2017/051206, dated Dec. 13, 2017, 11 pages.
Chen et al., "The outer membrane protein LptO is essential for the O-deacylation of LPS and the co-ordinated secretion and attachment of A-LPS and CTD proteins in Porphyromonas gingivalis," Molecular Microbiology, Mar. 2011, 79(5):1380-401.
GenBank Accession No. AB011549, "*Escherichia coli* O157:H7 str. Sakai plasmid pO157 DNA, complete sequence," dated Jul. 26, 2016, 34 pages.
GenBank Accession No. AF074613, "*Escherichia coli* O157:H7 str. EDL933 plasmid pO157, complete sequence," dated Jul. 26, 2016, 47 pages.
GenBank Accession No. AJ007716, "*Escherichia coli* plasmid pO157, espP natural mutant with inserted IS1203," 4 pages.
GenBank Accession No. X97542, "*E.coli* 8.6 kb DNA from plasmid p0157," dated Jul. 24, 2016, 4 pages.
GenBank Accession No. Y11275, "*E.coli* 7.4 kb DNA from plasmid, pO157," Jul. 26, 2016, 4 pages.
Hegreness et al., "Accelerated evolution of resistance in multictrug environments," Proceedings of the National Academy of Sciences, Sep. 16, 2008, 105(37):13977-81.
Morones-Ramirez et al., "Silver enhances antibiotic activity against gram-negative bacteria," Science Translational Medicine, Jun. 19, 2013, 5(190):190ra81-.
Pankey et al., "Clinical relevance of bacteriostatic versus bactericidal mechanisms of action in the treatment of Gram-positive bacterial infections," Clinical Infectious Diseases, Mar. 15, 2004, 38(6):864-70.
PCT International Preliminary Report on Patentability in International Appln. No. PCT/AU2017/051207, dated May 7, 2019, 6 pages.
PCT International Preliminary Report on Patentability in International Appln. No. PCT/AU2017/051206, dated May 7, 2019, 8 pages.
PCT International Search Report and Written Opinion for App. No. PCT/AU2017/051207, dated Dec. 18, 2017, 8 pages.
Sani et al., "Maculatin 1.1 disrupts *Staphylococcus aureus* lipid membranes via a pore mechanism," Antimicrobial Agents and Chemotherapy, Aug. 1, 2013, 57(8):3593-600.

\* cited by examiner (c) *P. aeruginosa*

(d) CMDR *P. aeruginosa*

(e) *A. baumannii*

(f) CMDR *A. baumannii*

(c) CMDR *P. aeruginosa* - Dox (d) CMDR *A. baumannii* - Ag⁺

(e) CMDR *A. baumannii* - Imi (a) Controls:

S16:

Figure 6 continued…
(b) Controls:
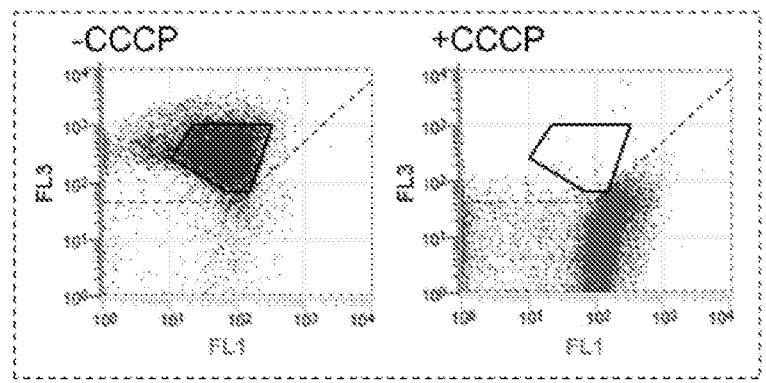
S16:
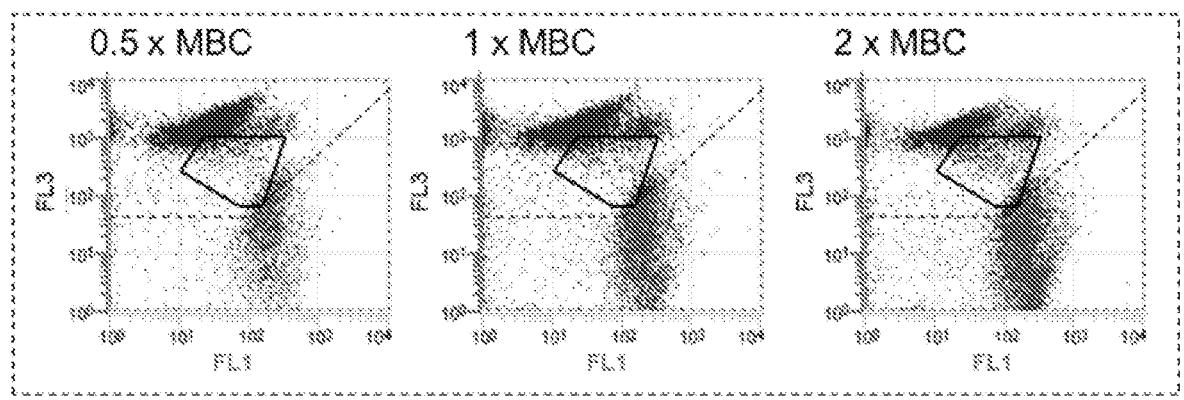

(a) *P. aeruginosa* - Amp (b) CMDR *P. aeruginosa* - Ag⁺

(c) CMDR *P. aeruginosa* - Dox (d) CMDR *A. baumannii* - Ag⁺

(e) CMDR *A. baumannii* - Imi (a) *P. aeruginosa* - Amp (b) CMDR *P. aeruginosa* - Ag⁺

(c) CMDR *P. aeruginosa* - Dox (d) CMDR *A. baumannii* - Ag⁺

(e) CMDR *A. baumannii* - Imi (a) *P. aeruginosa* - Amp (b) CMDR *P. aeruginosa* - Ag⁺

(c) CMDR *P. aeruginosa* - Dox (d) CMDR *A. baumannii* - Ag⁺

(e) CMDR *A. baumannii* - Imi

US 11,154,589 B2

ANTIMICROBIAL COMPOSITION COMBINATIONS COMPRISING STAR SHAPED PEPTIDE POLYMERS

CROSS REFERENCE TO RELATED APPLICATION(S)

This application claims priority from Australian application AU 2016904472, the contents of which is herein incorporated by reference in its entirety.

FIELD OF THE INVENTION

This invention relates to compositions including antibacterial compounds. The invention also relates to the use of the compositions in methods of treating bacterial infections.

BACKGROUND OF THE INVENTION

Named as one of the greatest healthcare advances in history, the discovery and development of potent and safe antibiotics have brought about major improvements to healthcare and quality of life in general. However, treatment of bacterial infections is currently limited by both the agents available and the bacterial resistance to those agents. In this regard, as clinical treatment options have become severely limited, there is a growing medical need for the development of novel antibacterial agents. Additionally, there is an unmet medical need to develop antibacterials where there are presently limited agents or in infections where the pathogens are difficult to treat. Such pathogens may include *Pseudomonas aeruginosa* and *Acinetobacter baumannii*.

The rise of antimicrobial resistance due to the widespread and prolonged misuse of conventional antibiotics, especially among Gram-negative bacteria, poses an alarming threat and has been linked to ineffective treatment, increased medical costs, and high morbidity and mortality rates. The problem is exacerbated by the fact that few new antibiotics are in development and most efforts are focused on developing antibiotics to combat resistant Gram-positive (but not Gram-negative) bacteria. Hence, there exists an urgent need for developing novel and effective antimicrobial agents to overcome multidrug-resistant (MDR) bacterial infections, particularly those caused by Gram-negative bacteria.

One such way to combat the continued spread of anti-bacterial resistance is to develop new antibacterials, particularly those with either a novel mechanism of action and/or containing new pharmacophoric groups. However, there are a large number of existing antibiotics of different classes which could find clinical application again if bacteria are susceptible to their anti-bacterial activity.

As such, there is a need for new or improved methods and compositions for treating infections caused by Gram-negative and/or Gram-positive bacterial pathogens, particularly those bacteria that exhibit resistance to antibiotics.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect the present invention provides a method of sensitizing bacteria to an anti-bacterial compound, the method comprising contacting the bacteria with a star shaped peptide polymer of the invention, thereby sensitizing the bacteria to an anti-bacterial compound.

In another aspect the present invention also provides a method of increasing the susceptibility of bacteria to an anti-bacterial activity of a compound, the method comprising contacting the bacteria with a star shaped peptide polymer of the invention, thereby increasing the susceptibility of the bacteria to the anti-bacterial activity of the compound. Preferably, the method further includes the step of contacting the bacteria with the compound for which the bacteria have increased susceptibility to.

In another aspect the present invention provides a pharmaceutical composition comprising a star shaped peptide polymer of the invention and an anti-bacterial compound. Preferably, the composition further comprises a physiologically acceptable carrier, diluent or excipient.

In another aspect the invention provides a pharmaceutical composition for treating or preventing a bacterial infection comprising a star shaped peptide polymer of the invention, an anti-bacterial compound and a pharmaceutically acceptable diluent, excipient or carrier. In one embodiment, the only active ingredients present in the composition are the star shaped peptide polymer and anti-bacterial compound.

In another aspect the invention provides a pharmaceutical composition for treating or preventing a bacterial infection comprising as active ingredients a star shaped peptide polymer of the invention and an anti-bacterial compound. Preferably, the composition further comprises a pharmaceutically acceptable diluent, excipient or carrier. In one embodiment, the only active ingredients present in the composition are the star shaped peptide polymer and anti-bacterial compound.

In another aspect the invention provides a pharmaceutical composition for treating or preventing a bacterial infection comprising as main ingredients a star shaped peptide polymer of the invention and an anti-bacterial compound. Preferably, the composition further comprises a pharmaceutically acceptable diluent, excipient or carrier. In one embodiment, the only active ingredients present in the composition are the star shaped peptide polymer and anti-bacterial compound.

In another aspect the present invention provides a method of treating a bacterial infection in a subject, the method comprising administering to the subject an anti-bacterial compound and a star shaped peptide polymer of the invention, thereby treating the bacterial infection in the subject.

In another aspect the present invention provides a method of reducing the risk of adverse events in a subject having antibiotic hypersensitivity, the method comprising administering to the subject a star shaped peptide polymer of the invention and an antibiotic to which the subject has hypersensitivity, thereby reducing the risk of adverse events in a subject having antibiotic hypersensitivity.

In another aspect the present invention provides a method of treating a bacterial infection in a subject having antibiotic hypersensitivity, the method comprising administering to the subject a star shaped peptide polymer of the invention and an antibiotic to which the subject has hypersensitivity, wherein the antibiotic is provided in an amount which does not result in any detectable adverse events associated with hypersensitivity, thereby treating a bacterial infection in a subject having antibiotic hypersensitivity.

It has now been found that the anti-bacterial efficacy of a composition containing an anti-bacterial compound can be significantly enhanced by the inclusion of a star shaped peptide polymer of the invention. Therefore, the present invention provides a method for increasing the anti-bacterial efficacy of a composition containing an anti-bacterial compound comprising adding a star shaped peptide polymer of the invention to the composition.

In another aspect, the present invention provides a star shaped peptide polymer of the invention for use in the treatment of a bacterial infection in a subject, wherein the treatment includes administering to the subject the star shaped peptide polymer of the invention and an anti-bacterial compound.

In another aspect the present invention provides a method of treating or preventing a bacterial infection in a subject in need thereof, the method comprising administering to the subject a therapeutically effective amount a pharmaceutical composition of the invention, thereby treating or preventing a bacterial infection in a subject.

In another aspect the present invention provides a method of treating a bacterial infection comprising administering to a subject diagnosed with, at risk for, or exhibiting symptoms of, a bacterial infection, a star shaped peptide polymer of the invention or a pharmaceutical composition of the invention, thereby treating a bacterial infection in a subject.

In another aspect the invention also provides a method of alleviating or ameliorating a symptom of a bacterial infection in a subject in need thereof, the method comprising administering to the subject in need thereof a therapeutically effective amount of a star shaped peptide polymer of the invention or a pharmaceutical composition of the invention, thereby alleviating or ameliorating a symptom of a bacterial infection in the subject.

In another aspect the present invention provides a method for the treatment of a bacterial infection in a subject comprising the steps of identifying a subject having a bacterial infection; and administering to the subject in need thereof a therapeutically effective amount of a star shaped peptide polymer of the invention or a pharmaceutical composition of the invention, thereby treating a bacterial infection in the subject.

In another aspect the present invention provides a combination of products for treating a bacterial infection in a subject comprising, a first composition comprising a star shaped peptide polymer of the invention and a second composition comprising an anti-bacterial compound. The first and second compositions may be administered simultaneously or sequentially.

In any aspect of the present invention the anti-bacterial compound is a molecule that exhibits bactericidal or bacteriostatic activity against bacteria. Bactericidal or bacteriostatic activity may be determined by any method described herein or known to a person skilled in the art. Typically, the anti-bacterial compound is selected from a known class of anti-bacterial compounds, including but not limited to:
(1) Macrolides or ketolides such as erythromycin, azithromycin, clarithromycin and telithromycin;
(2) Beta (β)-lactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, aztreonam, imipenem, meropenem, ertapenem, doripenem, ceftobiprole, and ceftaroline;
(3) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, garenoxacin, gemifloxacin and pazufloxacin;
(4) Antibacterial sulfonanmides and antibacterial sulphanilamides, including para-am inobenzoic acid, sulfadiazine, sulfisoxazole, sulfamethoxazole and sulfathalidine;
(5) Aminoglycosides such as streptomycin, neomycin, kanamycin, paromycin, gentamicin, tobramycin, amikacin, netilmicin, spectinomycin, sisomicin, dibekacin and isepamicin;
(6) Tetracyclines such as tetracycline, chlortetracycline, demeclocycline, minocycline, oxytetracycline, methacycline, tigecycline, doxycycline;
(7) Rifamycins such as rifampicin (also called rifampin), rifapentine, rifabutin, bezoxazinorifamycin and rifaximin;
(8) Lincosamides such as lincomycin and clindamycin;
(9) Glycopeptides such as telavancin, vancomycin and teicoplanin or lipopeptides such as daptomycin;
(10) Streptogramins such as quinupristin and daflopristin;
(11) Oxazolidinones such as linezolid;
(12) Polymyxin, colistin and colymycin; and
(13) Trimethoprim and bacitracin.

Preferably, the anti-bacterial compound is a β-lactam, an aminoglycoside or silver. Typically, the β-lactam is ampicillin, the amino glycoside is gentamicin, and the silver is in the form of dissolved ions, Ag+, preferably derived from a silver salt such as silver nitrate ($AgNO_3$).

In another aspect the present invention provides a method for treating a bacterial infection in a subject caused by, or comprising, *Escherichia coli, Klebsiella pneumoniae, P. aeruginosa*, and/or *A. baumannii*, the method comprising administering to the subject a star shaped peptide polymer of the invention and a β-lactam, thereby treating the bacterial infection in the subject. Preferably, the β-lactam is ampicillin.

In another aspect the present invention provides a method for treating a bacterial infection in a subject caused by, or comprising, *Escherichia coli, Klebsiella pneumoniae, P. aeruginosa*, and/or *A. baumannii*, the method comprising administering to the subject a star shaped peptide polymer of the invention and $AgNO_3$, thereby treating the bacterial infection in the subject.

In another aspect the present invention provides a method for treating a bacterial infection in a subject caused by, or comprising, *Escherichia coli, A. baumannii* and/or *Klebsiella pneumoniae*, the method comprising administering to the subject a star shaped peptide polymer of the invention and an aminoglycoside, thereby treating the bacterial infection in the subject. Preferably, the aminoglycoside is gentamicin.

In another aspect the present invention provides a method for treating a bacterial infection in a subject caused by, or comprising, *P. aeruginosa*, the method comprising administering to the subject a star shaped peptide polymer of the invention and a tetracycline, thereby treating the bacterial infection in the subject. Preferably, the tetracycline is doxycycline. Preferably, the *P. aeruginosa* exhibits resistance to any one or more anti-bacterial compounds as described herein. More preferably, the *P. aeruginosa* displays resistance to a tetracycline such as doxycycline. Typically, the *P. aeruginosa* displays resistance to any one or more, or all, of the antibiotics described in Table 4.

In another aspect the present invention provides a method for treating a bacterial infection in a subject caused by, or comprising, *A. baumannii*, the method comprising administering to the subject a star shaped peptide polymer of the invention and a β-lactam, thereby treating the bacterial infection in the subject. Preferably, the β-lactam is a carbapenem. Preferably, the carbapenem is imipenem. Preferably, the *A. baumannii* exhibits resistance to any one or more anti-bacterial compounds as described herein. More preferably, the *A. baumannii* displays resistance to a carbapenem such as imipenem. Typically, the *A. baumannii* displays resistance to any one or more, or all, of the antibiotics described in Table 5.

In any aspect of a method or use of the invention the *A. baumannii* present in the infection may exhibit resistance to any one or more of Amikacin, Ampicillin, Amoxicillin/Clavulanic Acid, Cefazolin, Cefepime, Cefoxitin, Ceftazidime, Ceftriaxone, Ciprofloxacin, Gentamicin, Meropenem, Nalidixic Acid, Nitrofurantoin, Norfloxacin, Piperacillin/Tazobactam, Ticarcillin/Clavulanic Aid, Tobramycin, Trimethoprim, Trimethoprim/Sulfamethoxazole, Imipenem and Colistin Sulfate. The *P. aeruginosa* present in the infection may exhibit resistance to any one or more of Ampicillin, Aztreonam, Ceftazidime, Gentamicin, Piperacillin, Ticarcillin, Tobramycin and Colistin Sulfate.

In another aspect the present invention provides a method for treating a bacterial infection in the peritoneal cavity of a subject, the method comprising administering to the subject a star shaped peptide polymer of the invention and a β-lactam, thereby treating the bacterial infection in the subject. Preferably, the β-lactam is a carbapenem.

Preferably, the carbapenem is imipenem. In one embodiment, the infection in the peritoneal cavity comprises or consists of *A. baumannii*. The *A. baumannii* may exhibit resistance to any one or more anti-bacterial compounds as described herein. More preferably, the *A. baumannii* displays resistance to a carbapenem such as imipenem. Typically, the *A. baumannii* displays resistance to any one or more, or all, of the antibiotics described in Table 5.

In another aspect the present invention provides a method of treating peritonitis in a subject, the method comprising administering to the subject a star shaped peptide polymer of the invention and a β-lactam, thereby treating peritonitis in the subject. Preferably, the β-lactam is a carbapenem. Preferably, the carbapenem is imipenem. In one embodiment, the peritonitis is caused by, or is associated with, *A. baumannii*. The *A. baumannii* may exhibit resistance to any one or more anti-bacterial compounds as described herein. More preferably, the *A. baumannii* displays resistance to a carbapenem such as imipenem. Typically, the *A. baumannii* displays resistance to any one or more, or all, of the antibiotics described in Table 5.

In any method or use of the invention described herein, a composition of the invention may be administered systemically or directly to the site of infection.

As used herein administration of a star shaped peptide polymer of the invention and an anti-bacterial compound includes either a fixed combination in one dosage unit form, or a kit of parts for the combined administration where a star shaped peptide polymer and an anti-bacterial compound may be administered independently at the same time or separately within time intervals that especially allow the combination to show a cooperative, e.g., synergistic, effect.

An anti-bacterial compound may be administered in combination with a star shaped peptide polymer of present invention wherein the antibacterial compound is administered prior to, simultaneously, or after a star shaped peptide polymer of the present invention. When simultaneous administration of a star shaped peptide polymer of the invention with an anti-bacterial compound is desired and the route of administration is the same, then a star shaped peptide polymer of the invention may be formulated with the anti-bacterial compound into the same dosage form.

In any method or use of the invention described herein, the bacterial infection may comprise, consisting essentially of or consist of Gram-negative or Gram-positive bacteria. The bacterial infection may include both Gram-negative and Gram-positive bacteria. Typically, the bacterial infection is an infection caused by one or more of Gram-negative bacterium selected from the group consisting of *Acinetobacter baumannii, Acinetobacter haemolyticus, Actinobacillus actinomycetemcomitans, Aeromonas hydrophila, Bacteroides fragilis, Bacteroides thetaiotaomicron, Bacteroides distasonis, Bacteroides ovatus, Bacteroides vulgatus, Bordetella pertussis, Brucella melitensis, Burkholderia cepacia, Burkholderia pseudomallei, Burkholderia mallei, Fusobacterium, Prevotella corporis, Prevotella intermedia, Prevotella endodontalis, Porphyromonas asaccharolytica, Campylobacter jejuni, Campylobacter fetus, Citrobacter freundii, Citrobacter koseri, Edwardsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella pneumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydia pneumoniae, Chlamydia trachomatis, Rickettsia prowazekii, Coxiella burnetii, Ehrlichia chaffeensis,* and *Bartonella henselae*. More preferably, the bacterial infection is an infection caused by one or more of bacterium selected from the group consisting of *Acinetobacter baumannii, Bordetella pertussis, Burkholderia cepacia, Burkholderia pseudomallei, Burkholderia mallei, Campylobacter jejuni, Campylobacter coli, Enterobacter cloacae, Enterobacter aerogenes, Escherichia coli, Francisella tularensis, Haemophilus influenzae, Haemophilus ducreyi, Helicobacter pylori, Klebsiella pneumoniae, Legionella pneumophila, Moraxella catarrhalis, Morganella morganii, Neisseria gonorrhoeae, Neisseria meningitidis, Pasteurella multocida, Proteus mirabilis, Proteus vulgaris, Pseudomonas aeruginosa, Salmonella typhi, Serratia marcescens, Shigella flexneri, Shigella boydii, Shigella sonnei, Shigella dysenteriae, Stenotrophomonas maltophilia, Vibrio cholerae,* and *Chlamydia pneumoniae*. Even more preferably, the bacterial infection is an infection caused by one or more of bacterium selected from the group consisting of *Acinetobacter baumannii, Bordetella pertussis, Burkholderia cepacia, Burkholderia pseudomallei, Burkholderia mallei, Campylobacter jejuni, Campylobacter coli, Enterobacter cloacae, Enterobacter aerogenes, Escherichia coli, Francisella tularensis, Haemophilus influenzae, Haemophilus ducreyi, Helicobacter pylori, Klebsiella pneumoniae, Legionella pneumophila, Moraxella catarrhalis, Morganella morganii, Proteus mirabilis, Proteus vulgaris, Pseudomonas aeruginosa, Serratia marcescens,* and *Stenotrophomonas maltophilia*.

In another aspect, the Gram-negative bacteria may be any one or more of the following implicated in chronic periodontitis: *Porphyromonas gingivalis, Treponema denticola, Tannerella forsythia, Aggregatibacter actinomycetemcomitans, Campylobacter rectus, Prevotella intermedia, Prevotella nigrescens, Fusobacterium nucleatum, Eikenella corrodens* and *Capnocytophaga ochracea*. Therefore, the present invention finds application to treat intra-oral bacteria, such as intra-oral antibiotic resistant bacteria.

In any aspect of the invention, the star shaped peptide polymer of the invention and anti-bacterial compound used display an additive or synergistic effect in inhibiting the growth of, or viability of, the bacteria. The capacity for the star shaped peptide polymer of the invention and anti-bacterial compound to display an additive or synergistic effect may be measured by any method described herein. Preferably, the additive or synergistic effect results in an about 2, 3, 4, 5, 6, 7, 8, 9, 10, 11, 12, 13, 14, 15, 16 or 20 fold reduction in the amount or concentration of anti-bacterial compound required to have a therapeutic, preventative or prophylactic effect.

In any aspect of the invention, the amount or concentration of star shaped peptide polymer of the invention and anti-bacterial compound administered to the subject or contact to the bacteria is sufficient for an additive or synergistic bacteriostatic or bactericidal effect.

In any aspect of the invention, the amount or concentration of star shaped peptide polymer of the invention administered to the subject or contact to the bacteria is sufficient to disrupt the bacterial membrane, for example as shown by the dose-dependent increase in the uptake of the membrane-impermeable propidium iodide (PI) dye (see, for example, Example 3 herein).

As used herein, except where the context requires otherwise, the term "comprise" and variations of the term, such as "comprising", "comprises" and "comprised", are not intended to exclude further additives, components, integers or steps. As used herein, the terms "including" and "comprising" may be used interchangeably.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
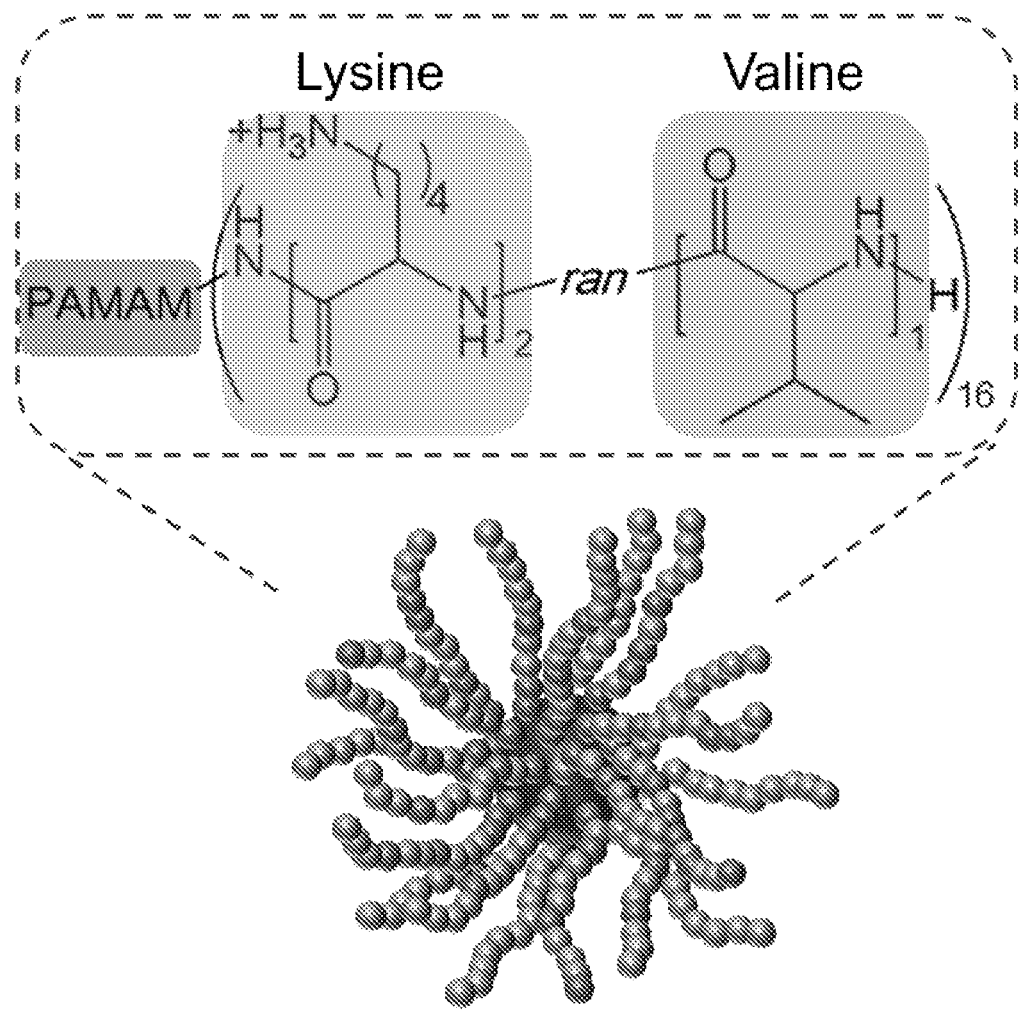
FIG. 1. Chemical structure of SNAPP S16.

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The rise and prevalence of multidrug-resistant bacteria, particularly Gram-negative bacteria has resulted in an urgent need for innovative approaches to treat life-threatening infections with these bacteria. Here, the inventors show that the star shaped peptide polymers described herein, are able to act as an effective adjuvant to different classes of conventional antibiotics in combating bacterial pathogens, including drug resistant bacteria such as colistin and multidrug-resistant (CMDR) species and opportunistic ESKAPE pathogens (which are named for their ability to 'escape' antibiotic action). Synergistic interactions were demonstrated between the star shaped peptide polymers described herein and ampicillin, imipenem, doxycycline, gentamicin, or silver ions. The inventors also show that the effective antibiotic dose could be decreased significantly (from about 3.7 to about 16-fold) from the original lethal dose while retaining synergistic interactions with the star shaped peptide polymer against CMDR bacteria. Further, the results in the Examples demonstrate that the combination treatment approach using a star shaped peptide polymer of the invention is able to attenuate toxicity associated with antibiotic monotherapy. Overall, the invention is based on the surprising finding of synergistic combinations of star shaped peptide polymers described herein with conventional antibiotics where the star shaped peptide polymer not only has anti-bacterial activity in its own right but also acts as an adjuvant for the conventional antibiotic to treat CMDR bacterial infections. The star shaped peptide polymers described herein may restore the anti-bacterial functionality of antibiotics which bacteria have developed complete or partial resistance to.

Through the combination of a star shaped peptide polymer as described herein and an anti-bacterial compound that interact with different and multiple bacterial targets, synergistic therapy has any one or more of the following advantages (1) reducing the likelihood of resistance acquisition, (2) re-sensitizing multi-drug resistant (MDR) bacteria to antibiotics that are otherwise ineffective when administered alone, and/or (3) mitigating toxic side-effects to the body as similar levels of antimicrobial efficacy could be attained with lower drug concentrations.

As used herein a "star shaped peptide polymer of the invention" is a star shaped peptide polymer as described below.

The star shaped peptide polymer of the invention comprises a multifunctional core with a plurality of terminal arms extending therefrom, wherein the terminal arms are statistical or random peptide copolymers of at least a cationic amino acid residue and a hydrophobic amino acid residue.

These star shaped peptide polymers are also referred to throughout this specification as star nanoparticles, and as 'Structurally Nanoengineered Antimicrobial Peptide Polymers' (SNAPPs).

In an embodiment, the terminal arms are statistical or random peptide copolymers of the cationic amino acid residue and the hydrophobic amino acid residue.

In an embodiment, the multifunctional core is a dendrimer.

In an embodiment the dendrimer comprises a dendrimer centre with a plurality of dendron arms extending therefrom, the dendron arms having a plurality of branches formed from repeat units, each branch terminated with a terminal unit having a terminal moiety; and wherein the plurality of terminal arms are each covalently bonded to terminal moieties of the dendrimer.

In an embodiment the terminal moiety is a secondary amine with one terminal arm covalently bonded thereto.

In an embodiment, the copolymer has a molar ratio of cationic amino acid residue to hydrophobic amino acid residue of from about 1.5:1 to about 3.5:1, and more preferably from about 1.8:1 to about 3:1. The molar ratio may be any one described herein, including in Table 6.

In an embodiment the cationic amino acid residue is an lysine residue (such as an L-lysine residue), and the hydrophobic amino acid residue is a valine residue (such as a D-valine, an L-valine, or DL-valine residues)

In an embodiment, the copolymer exhibits a degree of polymerisation of at least 5 and up to 50. In one form the degree of polymerisation is at least 8, in another form at least 10, in still another form at least 12, in yet another form at least 15, and in yet another form at least 20. Additionally, or alternatively, it is preferred that the degree of polymerisation is up to 45, more preferably up to 40.

In an embodiment, the degree of polymerisation is from about 5 to 35, and most preferably about 10 to about 30.

In one embodiment, the degree of copolymerisation is about 5, is about 10 to about 15, is 12 or 15, is about 20, is 18, is at least 25, or is at least 26 or 29.

In an embodiment, the dendrimer centre is a diamine core. Preferably the diamine core is of the form $R^1_2N$—($C_2$-$C_6$ alkyl)-$NR^1_2$, where each $R^1$ represents a covalent bond to a separate dendron arm. More preferably, the diamine core is of the form $R^1_2N$—($C_2$-$C_3$ alkyl)-$NR^1_2$. Most preferably, the diamine core is of the form $R^1_2N$—($C_2H_4$)—$NR^1_2$.

In an embodiment, the repeat unit is an amidoamine, such as of the form $R^A[C_2H_4C(=O)NH_2C_2H_4N]R^BR^C$ where $R^A$ is a single covalent bond to either the dendrimer centre (in which case $R^A$ is an $R^1$) or $R^A$ is a bond to a preceding repeat unit that is closer to the dendrimer centre (in which case $R^A$ is an $R^B$ or $R^C$ on the preceding repeat unit); $R^B$ and $R^C$ represent a single bond to a following repeat unit (in which case $R^B$ is an $R^A$ on the following repeat unit) or, where there are no following repeat units $R^B$ represents a single bond to the terminal arm, and $R^C$ represents a hydrogen atom.

There is no particular size limit on the dendrimer, for example, the dendrimer may be any generation of dendrimer. However, it is preferred that the dendrimer is a generation 0 to generation 5 dendrimer. More preferably, the dendrimer is a generation 0, 1, 2 or 3 dendrimer.

In an embodiment, the star shaped peptide polymer includes a number of terminal arms of from at least 3 and up to 256 terminal arms. Preferably the number of terminal arms is from at least 4 and up to 64. More preferably, the number of terminal arms is 4 to 32.

In an embodiment, the star shaped peptide polymer includes a number of terminal arms selected from the group consisting of: 4 terminal arms, 8 terminal arms, 16 terminal arms, 32 terminal arms, 64 terminal arms, 128 terminal arms, and 256 terminal arms. Preferably, the star shaped peptide polymer includes a number of terminal arms selected from the group consisting of: 4 terminal arms, 8 terminal arms, 16 terminal arms, 32 terminal arms.

In an embodiment, the statistical or random peptide copolymer exhibits an α-helix secondary structure. The presence of an α-helix secondary structure may be ascertained by circular dichroism (CD) spectroscopy. Where an α-helix secondary structure is present, the CD spectrum exhibits a characteristic band or bands in the far UV range (at wavelengths of 190 nm to 250 nm). In particular, a first negative band or trough is observable at a wavelength of between about 205 nm and about 210 nm, and a second negative band or trough is observable at a wavelength of between about 220 nm and about 225 nm. The presence of an α-helix secondary structure may also exhibit a positive band or peak at a wavelength between about 190 nm and 200 nm. The α-helix secondary structure is typically induced when the star shaped peptide polymer is exposed to a hydrophobic cell membrane. Thus, exposure of the star shaped peptide polymer to a hydrophobic environment that mimics that of the hydrophobic cell membrane can induce the α-helix secondary structure in the statistical or random peptide copolymer. In the present case, it is preferred that the statistical or random peptide copolymer exhibits the α-helix secondary structure when exposed to around 80% v/v trifluoroethanol (TFE), and such α-helix secondary structure is detectable using CD spectroscopy.

In an embodiment, the dendrimer is a PAMAM (Poly (amidoamine)) dendrimer. It is preferred that the PAMAM dendrimer. The number of branches that the PAMAM dendrimer has will depend on the number of repeat subunits that the dendrimer has. This may also be referred to as the "generation" of the PAMAM dendrimer. Those skilled in the art will appreciate that the PAMAM dendrimer may be continually grown outward through a series of two reactions (e.g. (i) the Michael addition of an amino terminated surface onto methyl acrylate, resulting in an ester-terminated outer layer, and (ii) coupling this with ethylene diamine to achieve a new amino-terminated surface).

However, it is preferred that the PAMAM dendrimer is a generation 1 to generation 5 PAMAM dendrimer, and preferably a generation 0, 1, 2 or 3 PAMAM dendrimer. For the avoidance of doubt, a generation 0 PAMAM dendrimer has 4 branches terminating in 4 terminal moieties, a generation 1 PAMAM dendrimer has 8 branches terminating in 8 terminal moieties, a generation 2 PAMAM dendrimer has 16 branches terminating in 16 terminal moieties, a generation 3 PAMAM dendrimer has 32 branches terminating in 32 terminal moieties, and so on.

In an embodiment, the star shaped peptide polymer is selected from:

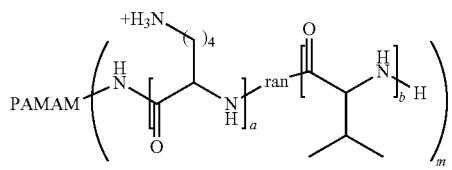

Where m is $2^n$ and n is a number between 2 and 8. Preferably n is 2, 3, 4 or 5, and m is 4, 8, 16 or 32 accordingly. In this context, cm' represents the total number of statistical or random peptide copolymers extending from the branches, and thus represents the total number of branches. 'a' and cb' represent the number of repeat units of lysine and valine in the peptide copolymer respectively.

In embodiments where n is 2, 3, 4 or 5, and m is 4, 8, 16 or 32 accordingly, it is preferred that the copolymer exhibits a degree of polymerisation of at least 5 and up to 50; preferably, at least 8 and up to 45; and more preferably at least 10 and up to 40.

Star shaped peptide polymers of the invention are generally described as comprising a multifunctional core with a plurality of terminal arms extending therefrom, wherein the terminal arms are statistical or random peptide copolymers of a cationic amino acid residue and a hydrophobic amino acid residue. The multifunctional core, may for example be a dendrimer. The dendrimer comprises a dendrimer centre, a plurality of dendron arms having a plurality of branches formed from repeat units and terminate with a terminal unity having a terminal moiety. The star shaped peptide polymer, may in certain embodiments, have a multifunctional core that is based on this dendrimer structure, wherein a statistical or random polypeptide copolymer (of at least a cationic amino acid residue and a hydrophobic amino acid residue) is covalently bonded to the terminal moieties of the dendrimer.

In this context, the term dendrimer centre is intended to refer to the molecule at the center of the dendrimer that gives rise to the final structure of the dendrimer. In the context of dendrimers formed via divergent synthesis techniques, the core molecule is effectively an "initiator" molecule which contains functional groups capable of acting as the initial active sites for forming the dendrimer. By way of example, in the context of a PAMAM based dendrimer, the dendrimer centre is based on an ethylene diamine initiator. Once the dendrimer has formed, each of the primary amine groups originally on the ethylene diamine molecule have been reacted with, and covalently bound to two dendron arms. Thus, the resultant dendrimer centre has the form of an ethylene diamine molecule wherein each amine group is a tertiary amine, such as of the form R2N(CH2)2NR2.

The term "dendron arms" is intended to refer to the branched groups that are covalently bound to the dendrimer centre. The number of dendron arms is dependent on the number of functional groups capable of acting as the initial active sites on the dendrimer centre. PAMAM has a core formed from an ethylene diamine initiator, and as such provides four active sites to which the dendron arms may be bound.

The dendron arms have a plurality of branches formed from repeat units and terminate with a terminal unity having a terminal moiety. It will be appreciated that the terms "terminal unit(s)" and the "terminal moiety" or "terminal moieties" relate to the dendrimer structure itself and are not intended to designate terminal groups of the star shaped peptide polymer. As is clear from the above, the star shaped peptide polymer further includes terminal arms (being statistical or random peptide copolymers of at least a cationic amino acid residue and a hydrophobic amino acid residue) which in one or more embodiments are covalently bound to the dendrimer via these terminal moieties on the terminal units of the dendrimer.

A number of different synthetic procedures can be used to generate the dendron arms. Typically, such procedures involve reacting functional groups on the core molecule with a further molecule having a first moiety that allows the nucleophilic addition of that further molecule onto the dendrimer centre (via the functional group on the dendrimer centre) and a second moiety for allowing the nucleophilic addition of two or more additional molecules. Again, in the context of PAMAM, the dendron arms can be formed via step (i) the Michael addition of two methyl acrylates onto each amine group of the ethylene diamine core, resulting in an ester-terminated outer layer, and step (ii) the subsequent coupling of ethylene diamine to ester-terminated outer layer to achieve two new amino-terminated surfaces for each amine surface prior to step (i). Thus, each repetition of reactions (i) and (ii) adds repeat units in a manner which doubles the number of branches in the dendron arms. Each repetition of this sequence of reactions to double the number of branches is referred to as a generation. The process may be repeated until dendron arms of the desired size (re desired number of generations) have been reached. The molecules that form the outer portions of the branches are the terminal units, and these terminal units include a terminal moiety (which in the context of PAMAM is an amine). Thus, in the context of this invention, the terminal moiety refers to the end moiety of the repeat units that form the branches of the dendron arms. Advantageously, another molecule (in particular a statistical or random peptide copolymer) can be conjugated to these terminal moieties.

A statistical or random peptide copolymer is a copolymer formed from at least two different peptide units or amino acid residues. Statistical copolymers are copolymers in which the sequence of monomer residues follows a statistical rule. If the probability of finding a given type monomer residue at a particular point in the chain is equal to the mole fraction of that monomer residue in the chain, then the polymer may be referred to as a random copolymer.

In this context, the "amino acid residues" is intended to refer to discrete amino acid monomers linked by peptide bonds in the copolymer. A cationic amino acid residue is one having a moiety exhibiting a positive charge. An example of this is a lysine residue which includes a protonated sidechain including an $NH^{3+}$ moiety. A hydrophobic amino acid residue is one which includes a non-polar residue, such as valine which has an isopropyl side chain rendering the residue hydrophobic.

In another aspect the present invention provides a star shaped peptide polymer of the invention prepared by a process comprising the steps of: forming a reaction solution comprising: a solvent, the multifunctional core, and either: (i) the statistical or random polypeptide copolymer, or (ii) a cationic peptide monomer and a hydrophobic peptide monomer; and agitating the solution for a period of time to form the star shaped peptide polymer. In an embodiment, the multifunctional core is the dendrimer.

In an embodiment, the solvent is a non-aqueous solution. The non-aqueous solvent may be a polar non-aqueous solvent and/or a water miscible solvent. Preferably, the solvent is an organic solvent. While a range of different solvents may be employed, the most preferred solvent is dimethylformamide (DMF), such as anhydrous DMF.

In an embodiment, the step of agitating the solution is conducted under an inert atmosphere. The term "inert atmosphere" is intended to refer to a gaseous mixture that contains little or no oxygen (preferably no oxygen) and primarily consists of gases or gases that are non-reactive within the context of this method. Suitable gases include nitrogen, argon, helium, carbon dioxide, and mixtures thereof. However, it is preferred that the inert atmosphere comprises argon gas. More preferably the inert atmosphere consists of argon gas.

In an embodiment, the step of agitating the solution includes agitating the solution at ambient temperature.

In an embodiment, the method includes forming a reaction solution comprising: a solvent, the multifunctional core, and a cationic peptide monomer and a hydrophobic peptide monomer. In this embodiment, it is preferred that the step of agitating the solution includes agitating the solution at a temperature of from greater than 0° C. and up to 10° C. Preferably, the temperature is from greater than 0° C. and up to 8° C. More preferably, the temperature is from greater than 0° C. and up to 6° C. Even more preferably, the temperature is from greater than 0° C. and up to 5° C. Most preferably, the temperature is from greater than 0° C. and up to 4° C.

In an embodiment, the solution is agitated for a period of at least 2 hours, preferably at least 6 hours, more preferably at least 12 hours, even more preferably at least 18 hours, most preferably at least 24 hours. The duration of the reaction is important for forming terminal arms of the desired composition and/or number of repeating units. Shorter reaction times result in shorter statistical or random peptide copolymer terminal arms. It is preferred that the solution is agitated for a period of up to 30 hours, more preferably up to 26 hours, and most preferably up to 24 hours.

In an embodiment where the reaction solution comprises the cationic peptide monomer and the hydrophobic peptide monomer, the step of forming the reaction solution includes adding the cationic peptide monomer and the hydrophobic peptide monomer to the solvent at substantially the same time. In this context, the term "substantially the same time"

is intended to cover the situation where the cationic peptide monomer and the hydrophobic peptide monomer are added simultaneously, or where the cationic peptide monomer and the hydrophobic peptide monomer are added sequentially. Where the cationic peptide monomer and the hydrophobic peptide monomer are added sequentially, it is preferred that this is within a time period of 10 minutes, and more preferably within a time period of 5 minutes.

The cationic peptide monomer may be a cationic amino acid or a cationic amino acid derivative that is polymerisable to form the cationic amino acid residue. Similarly, the hydrophobic peptide monomer may be a hydrophobic amino acid or a hydrophobic amino acid derivative that is polymerisable to form the hydrophobic amino acid residue. It is preferred that the cationic amino acid derivative and the hydrophobic amino acid derivative are in the form of amino acid N-carboxyanhydrides. In one form of the invention, the cationic peptide monomer is lysine or a lysine N-carboxyanhydride, and the hydrophobic peptide monomer is valine or a valine N-carboxyanhydride.

In an embodiment, the cationic peptide monomer includes a cationic moiety that is protected with a protecting group, such as with a Fluorenylmethyloxycarbonyl (FMOC) protecting group, a carboxybenzyl (Cbz) protecting group, or a tert-Butyloxycarbonyl (BOC) protecting group. In a preferred form, where the cationic peptide monomer is lysine or a lysine derivative, a pendant amine group is protected with a protecting group. In instances where a protecting group is present, the method may further include the step of removing the protecting group from the polypeptide copolymer. The protecting group may be removed by using techniques disclosed herein or techniques known to those skilled in the art.

In an embodiment, the process further includes precipitating the star shaped peptide polymer into a second solvent phase comprising a second solvent within which the star shaped peptide polymer is not soluble. Preferably, the solvent is a polar solvent, and the second solvent is a non-polar solvent. Diethyl ether is a suitable non-polar solvent.

The process for preparing a star shaped peptide polymer of the invention may include any one or more steps as described in the Examples or in Lam et al. Nature Microbiology. (2016) Sep. 12; 1:16162.

The frequency of administration of a star shaped peptide polymer of the invention may follow the normal frequency and time course for the anti-bacterial compound which it is co-administered.

Subjects suffering from a bacterial infection, or healthy control subjects, may be assessed before and after treatment of a star shaped peptide polymer of the invention, by using any one of, or combination of, numerous different standards or scales employed by a person having ordinary skill in the art. Examples of standards or scales for testing the effectiveness of the methods disclosed herein include assessment of body temperature, body weight, Lab-Score, procalcitonin levels, circulating white blood cell levels, Laboratory Risk Indicator for Necrotizing Fasciitis (LRINEC) score, mucus levels, urea breath test, or levels of bacteria present in a sample taken from a subject (e.g. blood, serum, mucus, skin, stool, urine, sputum, saliva, semen, or biopsy sample). The existence of a bacterial infection in a subject may be determined by any one of these methods or others as described herein or known in the art.

As used herein, a "subject" refers to an animal, such as a mammalian or an avian species, including a human, an ape, a horse, a cow, a sheep, a goat, a dog, and a cat. The subject may have a bacterial infection, may have been exposed to infectious bacteria, may be at risk for developing a bacterial infection, or may be at greater risk than the general population for developing a bacterial infection. Examples of subjects at greater risk for developing a bacterial infection include patients undergoing treatment for bacterial infections whereby normal gut flora is inhibited by antimicrobial therapy, patients with impaired immune function (e.g., immunoglobulin deficiency, splenic dysfunction, splenectomy, HIV infection, impaired leukocyte function, hemoglobinopathies), the elderly, people with certain malignancies (e.g., multiple myeloma, chronic lympocytic leukemia, lymphoma), people at increased occupational risk (e.g., public services workers, such a fire, water, sanitary, police, medical, and laboratory workers, hospital workers), people in closed populations (e.g., prisons, military, nursing homes) and others that have immunological deficiencies that might enhance their susceptibility to bacterial infection.

A subject having antibiotic hypersensitivity may exhibit an adverse event after exposure to an antibiotic. The adverse events associated with hypersensitivity may be IgE-mediated immediate hypersensitivity, IgE-independent reactions, or delayed reactions. IgE-mediated immediate hypersensitivity is characterised by the development of urticaria, angioedema, bronchospasm or anaphylaxis (with objectively demonstrated hypotension, hypoxia or tryptase elevation), usually within one hour of antibiotic administration. If there is more delay, there is less likelihood that the reaction is IgE-mediated. IgE-independent reactions do not involve IgE but may mimic IgE-mediated allergy (e.g. responses to vancomycin infusions such as 'red-man' syndrome) involve the direct release of vasoactive mediators (e.g. histamine). Delayed reactions may take the form of macular, papular, or morbilliform rashes occurring several days after commencement of treatment. Diagnosis of antibiotic hypersensitivity may be analysis of the clinical history of the subject, skin or blood testing or cross-reactivity.

A bacterial infection generally refers to:
(1) an elevated level of bacteria in a sample taken from the individual compared to an uninfected control sample;
(2) an increased proportion of one or more types of bacteria in a sample taken from the individual compared to the total level of bacteria in an uninfected control sample;
(3) an increased proportion of bacteria relative to one or more other bacteria species in a sample taken from the individual when compared to an uninfected control sample; or
(4) the presence of a bacteria in a sample compared to an uninfected control sample when that same bacteria is undetectable in the uninfected control.

A subject may be diagnosed as having a bacterial infection by any method described herein or known in the art. A biological sample such as a bodily fluid sample (e.g. blood) or tissue sample or scraping. Then the sample is prepared (various ways) and then cultured on different agar plates with defined media that will classify the microbe. Real time PCR is another method that may be used to identify bacteria in a sample.

In one aspect, the terms "infection" and "bacterial infection" refer to an infection caused by Gram-negative bacteria, also referred to as a "Gram-negative infection". In one aspect of this embodiment, the Gram-negative infection is an infection resistant to one or more antibiotics. In one aspect of this embodiment, the Gram-negative infection is a multi-drug resistant infection. In certain embodiments, the Gram-negative bacterium is *Acinetobacter* spp. In certain embodiments, the Gram-negative bacterium is *Acineto-* bacter spp., such as *Acinetobacter baumannii*. In certain embodiments, the Gram-negative bacterium is *Burkholderia* spp. In certain embodiments, the Gram-negative bacterium is *Burkholderia pseudomallei*. In certain embodiments, the Gram-negative bacterium is *Pseudomonas aeruginosa*. In certain embodiments, the Gram-negative bacterium is Enterobacteriaceae. In any of these embodiments, the Gram-negative infection arises from a pathogen or pathogen expressing one or more β-lactamase. In any of these embodiments, the Gram-negative infection arises from a pathogen or pathogen expressing one or more Class A, Class C and/or Class D β-lactamase. In any of these embodiments, the Gram-negative infection arises from a pathogen or pathogen expressing one or more Class A β-lactamase. In any of these embodiments, the Gram-negative infection arises from a pathogen or pathogen expressing one or more Class C β-lactamase. In any of these embodiments, the Gram-negative infection arises from a pathogen or pathogen expressing one or more Class D β-lactamase.

An infection caused by "Enterobacteriaceae" refers to any of the Gram-negative bacteria in this family of bacteria which includes, but is not limited to, species such as *Salmonella* spp., *Escherichia coli*, *Yersinia pestis*, *Klebsiella* spp., *Shigella* spp., *Proteus* spp., *Enterobacter* spp., *Serratia* spp., and *Citrobacter* spp. Thus, treatment of a bacterial infection caused by "Enterobacteriaceae" includes any infection caused by any one or more bacteria which is part of this family. In one embodiment, a bacterial infection caused by "Enterobacteriaceae" includes bacterial infections which have at least one *Salmonella* spp. pathogen present. In one embodiment, a bacterial infection caused by "Enterobacteriaceae" includes bacterial infections which have at least one *Escherichia coli* pathogen present. In one embodiment, a bacterial infection caused by "Enterobacteriaceae" includes bacterial infections which have at least one *Yersinia pestis* pathogen present. In one embodiment, a bacterial infection caused by "Enterobacteriaceae" includes bacterial infections which have at least one *Klebsiella* spp. pathogen present. In one embodiment, a bacterial infection caused by "Enterobacteriaceae" includes bacterial infections which have at least one *Shigella* spp. pathogen present. In one embodiment, a bacterial infection caused by "Enterobacteriaceae" includes bacterial infections which have at least one *Proteus* spp. pathogen present. In one embodiment, a bacterial infection caused by "Enterobacteriaceae" includes bacterial infections which have at least one *Enterobacter* spp. pathogen present. In one embodiment, a bacterial infection caused by "Enterobacteriaceae" includes bacterial infections which have at least one *Serratia* spp. pathogen present. In one embodiment, a bacterial infection caused by "Enterobacteriaceae" includes bacterial infections which have at least one *Citrobacter* spp. pathogen present.

In certain embodiments, the terms "infection" and "bacterial infection" refer to a infection caused by Gram-negative bacteria, wherein the Gram-negative bacterium is Enterobacteriaceae which expresses one or more Class A, Class B, Class C and/or Class D β-lactamase. In one aspect of this embodiment, the Gram-negative bacterium is an Enterobacteriaceae which expresses at least one Class B β-lactamase.

In certain embodiments, the Gram-negative bacterium is *Acinetobacter* spp. which expresses one or more β-lactamases. In one embodiment, the Gram-negative bacterium is *Acinetobacter baumannii* which expresses one or more Class A, Class C and/or Class D β-lactamase. In one embodiment, the Gram-negative bacterium is *Acinetobacter baumannii* which expresses one or more Class A β-lactamase. In one embodiment, the Gram-negative bacterium is *Acinetobacter baumannii* which expresses one or more Class C β-lactamase. In one embodiment, the Gram-negative bacterium is *Acinetobacter baumannii* which expresses one or more Class D β-lactamase. In one embodiment, the Gram-negative bacterium is *Acinetobacter baumannii* which expresses TEM-1 or KPC-2.

The term "Gram-negative" is art-recognized as those bacteria that do not retain crystal violet dye in the Gram staining protocol. For example, as used herein, the term "Gram-negative bacteria" describes one or more (i.e., a combination) of the following *Acinetobacter baumannii*, *Acinetobacter haemolyticus*, *Actinobacillus actinomycetemcomitans*, *Aeromonas hydrophila*, *Bacteroides fragilis*, *Bacteroides thetaiotaomicron*, *Bacteroides distasonis*, *Bacteroides ovatus*, *Bacteroides vulgatus*, *Bordetella pertussis*, *Brucella melitensis*, *Burkholderia cepacia*, *Burkholderia pseudomallei*, *Burkholderia mallei Fusobacterium*, *Prevotella corporis*, *Prevotella intermedia*, *Prevotella endodontalis*, *Porphyromonas asaccharolytica*, *Campylobacter jejuni*, *Campylobacter coli*, *Campylobacter fetus*, *Citrobacter freundii*, *Citrobacter koseri*, *Edwarsiella tarda*, *Eikenella corrodens*, *Enterobacter cloacae*, *Enterobacter aerogenes*, *Enterobacter agglomerans*, *Escherichia coli*, *Francisella tularensis*, *Haemophilus influenzae*, *Haemophilus ducreyi*, *Helicobacter pylori*, *Kingella kingae*, *Klebsiella pneumoniae*, *Klebsiella oxytoca*, *Klebsiella rhinoscleromatis*, *Klebsiella ozaenae*, *Legionella penumophila*, *Moraxella catarrhalis*, *Morganella morganii*, *Neisseria gonorrhoeae*, *Neisseria meningitidis*, *Pasteurella multocida*, *Plesiomonas shigelloides*, *Proteus mirabilis*, *Proteus vulgaris*, *Proteus penneri*, *Proteus myxofaciens*, *Providencia stuartii*, *Providencia rettgeri*, *Providencia alcalifaciens*, *Pseudomonas aeruginosa*, *Pseudomonas fluorescens*, *Salmonella typhi*, *Salmonella paratyphi*, *Serratia marcescens*, *Shigella flexneri*, *Shigella boydii*, *Shigella sonnei*, *Shigella dysenteriae*, *Stenotrophomonas maltophilia*, *Streptobacillus moniliformis*, *Vibrio cholerae*, *Vibrio parahaemolyticus*, *Vibrio vulnificus*, *Vibrio alginolyticus*, *Yersinia enterocolitica*, *Yersinia pestis*, *Yersinia pseudotuberculosis*, *Chlamydophila pneumoniae*, *Chlamydophila trachomatis*, *Ricketsia prowazekii*, *Coxiella burnetii*, *Ehrlichia chafeensis*, or *Bartonella hensenae*. Moreover, it is expected that the a star shaped peptide polymer or composition of the present invention will be useful in treating one or more bacterial infections.

In another aspect, the Gram-negative bacteria may be any one or more of the following implicated in chronic periodontitis: *Porphyromonas gingivalis*, *Treponema denticola*, *Tannerella forsythia*, *Aggregatibacter actinomycetemcomitans*, *Campylobacter rectus*, *Prevotella intermedia*, *Prevotella nigrescens*, *Fusobacterium nucleatum*, *Eikenella corrodens* and *Capnocytophaga ochracea*. Therefore, the present invention finds application to treat intra-oral bacteria, such as antibiotic resistant bacteria.

In another aspect, the terms "infection" and "bacterial infection" refer to an infection caused by Gram-positive bacteria, also referred to as a "Gram-positive infection".

Gram-positive bacteria refer to bacteria that are stained blue or violet by gram staining, and include, for example, *Staphylococcus aureus*, *Lactobacillus* spp, *Bifidobacteria* and *Scardovia wiggsiae* and the like. Gram-positive bacteria feature a thick peptidoglycan layer around a cell membrane and having no outer membrane on a periphery of the cell membrane. Gram-positive bacteria is not limited to Gram-positive cocci or Gram-positive bacilli.

A bacteria may be considered as resistant to a certain antibiotic if the MIC is above its breakpoint. Breakpoint tables are published by the relevant committees and known to the skilled person, for example:
1. European Committee on Antimicrobial Susceptibility http://www.eucast.org/clinical_breakpoints/-Clinical breakpoints-bacteria (v 6.0).
2. Clinical and Laboratory Standards Institute (CLSI) http://clsi.org/m100/

Any clinical or biochemical tests as described herein could be performed to determine whether particular bacteria are resistant to an antibiotic, including Broth microdilution (MIC) and disk diffusion assays.

Bacteria may be considered resistant to an antibiotic or anti-bacterial compound, if no bactericidal effect is observed at up to 5 mg/ml when tested in vitro. Alternatively, bacteria may be deemed resistant to an antibiotic or anti-bacterial compound because no improvement is seen clinically in a patient's condition upon administration of a full regimen of that antibiotic or anti-bacterial compound. Conversely, bacteria are considered to be sensitive to an antibiotic or anti-bacterial compound when bactericidal activity can be detected at therapeutically effective ranges or when an improvement is seen in a patient's condition upon administration of a full regimen of that antibiotic.

An "antibiotic resistant bacteria" or "bacteria that exhibit antibiotic resistance" may exhibit detectable resistance to one or more known antibiotics, including but not limited to:
(1) Macrolides or ketolides such as erythromycin, azithromycin, clarithromycin and telithromycin;
(2) Beta (β)-lactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, aztreonam, imipenem, meropenem, ertapenem, doripenem, ceftobiprole, and ceftaroline;
(3) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, garenoxacin, gemifloxacin and pazufloxacin;
(4) Antibacterial sulfonanmides and antibacterial sulphanilamides, including para-am inobenzoic acid, sulfadiazine, sulfisoxazole, sulfamethoxazole and sulfathalidine;
(5) Aminoglycosides such as streptomycin, neomycin, kanamycin, paromycin, gentamicin, tobramycin, amikacin, netilmicin, spectinomycin, sisomicin, dibekacin and isepamicin;
(6) Tetracyclines such as tetracycline, chlortetracycline, demeclocycline, minocycline, oxytetracycline, methacycline, tigecycline, doxycycline;
(7) Rifamycins such as rifampicin (also called rifampin), rifapentine, rifabutin, bezoxazinorifamycin and rifaximin;
(8) Lincosamides such as lincomycin and clindamycin;
(9) Glycopeptides such as telavancin, vancomycin and teicoplanin or lipopeptides such as daptomycin;
(10) Streptogramins such as quinupristin and daflopristin;
(11) Oxazolidinones such as linezolid;
(12) Polymyxin, colistin and colymycin; and
(13) Trimethoprim and bacitracin.

Non-limiting examples of bacteria exhibiting resistance to aztreonam include examples of staphylococci, *Staphylococcus aureus, Staphylococcus hemolyticus; Xanthomonas maltophilia; Aeromonas hydrophila; Citrobacter diversus; Enterobacter agglomerans, Haemophilus* spp., *Streptococcus pyogenes* and *P. aeruginosa*.

Non-limiting examples of bacteria that exhibit resistance to colistin include *Brucella, Burkholderia cepacia, Chryseobacterium indologenes, Edwardsiella, Elizabethkingia meningoseptica, Francisella tularensis* spp. Gram-negative cocci, *Helicobacter pylori, Moraxella catarrhalis, Morganella* spp., *Neisseria gonorrheae* and *Neisseria meningitides, Proteus, Providencia, Serratia, Stenotrophomonas maltophilia, Aeromonas, Vibrio, Prevotella, Fusobacterium*, and *Escherichia coli*.

The bacteria to be sensitized may exhibit complete, partial or no detectable resistance to a specific anti-bacterial compound. In the case that the bacteria exhibits complete resistance to an anti-bacterial compound, sensitization by the methods described herein causes the bacteria to exhibit susceptibility to cytostasis or cell death thereby restoring at least some efficacy of the anti-bacterial compound. In the case that the bacteria exhibit partial resistance to an anti-bacterial compound, sensitization by the methods described herein potentiates the efficacy or anti-bacterial activity of the anti-bacterial compound. In the case that the bacteria exhibit no detectable resistance to a specific anti-bacterial compound, sensitization by the methods described herein allows lower amounts or concentrations of anti-bacterial compound to achieve an anti-bacterial effect.

Sensitizing bacteria by any method or use of the invention described herein may at least (1) lower the clinically useful concentrations of anti-bacterial compounds/antibiotics used and lower anti-bacterial compound/antibiotic use, (2) prolong the usefulness of the current anti-bacterial compound/antibiotic treatments against bacterial infection by sensitizing antibiotic-resistant strains to those same antibiotics, (3) allow the use of current anti-bacterial compounds/antibiotics to treat a currently untreatable infection, and/or (4) extend the use of anti-bacterial compounds/antibiotics before the bacteria acquire resistance (if ever).

Sensitizing bacteria to an anti-bacterial compound by a method or use described herein may decrease the minimum bactericidal concentration or minimum inhibitory concentration by at least about 2, 3, 4, 5, 6, 7, 8, 9, 10, 11, 12, 13, 14, 15, 16 or 20 fold. Alternatively, sensitizing bacteria may result in a treatment refractory bacterial infection in a subject being treatable.

The present invention provides compositions and methods for potentiating the effects of antibiotics or anti-bacterial compounds against bacteria, which are sensitive to antibiotics or anti-bacterial compounds. In this embodiment, potentiation is in the form of reducing the amount of an antibiotic or anti-bacterial compounds that is needed to treat the infection compared to the amount needed without a star shaped peptide polymer of the invention. Accordingly, the present invention provides a method of treating a bacterial infection in a subject receiving an antibiotic or anti-bacterial compound, the method comprising the step of administering to the subject a star shaped peptide polymer of the invention, thereby treating the bacterial infection.

An increase in efficacy of an anti-bacterial compound by a star shaped peptide polymer of the invention may be determined using any method described herein including determining the minimum bactericidal concentration or minimum inhibitor concentration.

Exemplary bacteria which can result in an infection and which the present invention finds particular application in the treatment, prevention or prophylaxis of are now described below. Also described in the context of the different types of bacteria are conditions associated with, or caused by, a bacterial infection comprising or consisting of that type of bacteria.

*Escherichia coli* (*E. coli*) is a Gram-negative bacterium that is part of the normal flora of the gastrointestinal tract. There are hundreds of strains of *E. coli*, most of which are harmless and live in the gastrointestinal tract of healthy humans and animals. Currently, there are four recognized classes of enterovirulent *E. coli* (the "EEC group") that cause gastroenteritis in humans. Among these are the enteropathogenic (EPEC) strains and those whose virulence mechanism is related to the excretion of typical *E. coli* enterotoxins. Such strains of *E. coli* can cause various diseases including those associated with infection of the gastrointestinal tract and urinary tract, septicemia, pneumonia, and meningitis. Antibiotics are not effective against some strains and do not necessarily prevent recurrence of infection.

For example, *E. coli* strain 0157:H7 is estimated to cause 10,000 to 20,000 cases of infection in the United States annually (Federal Centers for Disease Control and Prevention). Hemorrhagic colitis is the name of the acute disease caused by *E. coli* 0157:H7. Preschool children and the elderly are at the greatest risk of serious complications.

Exemplary sequences for enterovirulent *E. coli* strains include GenBank Accession Numbers AB011549, X97542, AF074613, Y11275 and AJ007716.

*Salmonella thyphimurium*, are Gram-negative bacteria which cause various conditions that range clinically from localized gastrointestinal infections, gastroenterits (diarrhea, abdominal cramps, and fever) to enteric fevers (including typhoid fever) which are serious systemic illnesses. *Salmonella* infection also causes substantial losses of livestock.

Typical of Gram-negative bacilli, the cell wall of *Salmonella* spp. contains a complex lipopolysaccharide (LPS) structure that is liberated upon lysis of the cell and may function as an endotoxin, which contributes to the virulence of the organism.

Contaminated food is the major mode of transmission for non-typhoidal *salmonella* infection, due to the fact that *Salmonella* survive in meats and animal products that are not thoroughly cooked. The most common animal sources are chickens, turkeys, pigs, and cows; in addition to numerous other domestic and wild animals. The epidemiology of typhoid fever and other enteric fevers caused by *Salmonella* spp. is associated with water contaminated with human feces.

Vaccines are available for typhoid fever and are partially effective; however, no vaccines are available for non-typhoidal *Salmonella* infection. Non-typhoidal *salmonellosis* is controlled by hygienic slaughtering practices and thorough cooking and refrigeration of food. Antibiotics are indicated for systemic disease, and Ampicillin has been used with some success. However, in patients under treatment with excessive amounts of antibiotics, patients under treatment with immunsuppressive drugs, following gastric surgery, and in patients with hemolytic anemia, leukemia, lymphoma, or AIDS, *Salmonella* infection remains a medical problem.

*Pseudomonas* spp. are motile, Gram-negative rods which are clinically important because they are resistant to most antibiotics, and are a major cause of hospital acquired (nosocomial) infections. Infection is most common in: immunocompromised individuals, burn victims, individuals on respirators, individuals with indwelling catheters, IV narcotic users and individual with chronic pulmonary disease (e.g., cystic fibrosis). Although infection is rare in healthy individuals, it can occur at many sites and lead to urinary tract infections, sepsis, pneumonia, pharyngitis, and numerous other problems, and treatment often fails with greater significant mortality.

*Pseudomonas aeruginosa* is a Gram-negative, aerobic, rod-shaped bacterium with unipolar motility. An opportunistic human pathogen, *P. aeruginosa* is also an opportunistic pathogen of plants. Like other Pseudomonads, *P. aeruginosa* secretes a variety of pigments. Definitive clinical identification of *P. aeruginosa* can include identifying the production of both pyocyanin and fluorescein as well as the organism's ability to grow at 42° C. *P. aeruginosa* is also capable of growth in diesel and jet fuel, for which it is known as a hydrocarbon utilizing microorganism (or "HUM bug"), causing microbial corrosion.

*Vibrio cholerae* is a Gram-negative rod which infects humans and causes cholera, a disease spread by poor sanitation, resulting in contaminated water supplies. *Vibrio cholerae* can colonize the human small intestine, where it produces a toxin that disrupts ion transport across the mucosa, causing diarrhea and water loss. Individuals infected with *Vibrio cholerae* require rehydration either intravenously or orally with a solution containing electrolytes. The illness is generally self-limiting; however, death can occur from dehydration and loss of essential electrolytes. Antibiotics such as tetracycline have been demonstrated to shorten the course of the illness, and oral vaccines are currently under development.

*Neisseria gonorrhoea* is a Gram-negative coccus, which is the causative agent of the common sexually transmitted disease, gonorrhea. *Neisseria gonorrhoea* can vary its surface antigens, preventing development of immunity to reinfection. Nearly 750,000 cases of gonorrhea are reported annually in the United States, with an estimated 750,000 additional unreported cases annually, mostly among teenagers and young adults. Ampicillin, amoxicillin, or some type of penicillin used to be recommended for the treatment of gonorrhea. However, the incidence of penicillin-resistant gonorrhea is increasing, and new antibiotics given by injection, e.g., ceftriaxone or spectinomycin, are now used to treat most gonococcal infections.

*Staphylococcus aureus* is a Gram-positive coccus which normally colonizes the human nose and is sometimes found on the skin. *Staphylococcus* can cause bloodstream infections, pneumonia, and surgical-site infections in the hospital setting (i.e., nosocomial infections). Staph. *aureus* can cause severe food poisoning, and many strains grow in food and produce exotoxins. *Staphylococcus* resistance to common antibiotics, e.g., vancomycin, has emerged in the United States and abroad as a major public health challenge both in community and hospital settings. Recently, a vancomycin-resistant Staph. *aureus* isolate has also been identified in Japan.

*Mycobacterium tuberculosis* is a Gram positive bacterium which is the causative agent of tuberculosis, a sometimes crippling and deadly disease. Tuberculosis is on the rise and globally and the leading cause of death from a single infectious disease (with a current death rate of three million people per year).

It can affect several organs of the human body, including the brain, the kidneys and the bones, however, tuberculosis most commonly affects the lungs.

In the United States, approximately ten million individuals are infected with *Mycobacterium tuberculosis*, as indicated by positive skin tests, with approximately 26,000 new cases of active disease each year. The increase in tuberculosis (TB) cases has been associated with HIV/AIDS, homelessness, drug abuse and immigration of persons with active infections. Current treatment programs for drug-susceptible TB involve taking two or four drugs (e.g., isoniazid, rifampin, pyrazinamide, ethambutol or streptomycin), for a period of from six to nine months, because all of the TB germs cannot be destroyed by a single drug. In addition, the observation of drug-resistant and multiple drug resistant strains of *Mycobacterium tuberculosis* is on the rise.

*Helicobacter pylori* (*H. pylori*) is a micro-aerophilic, Gram-negative, slow-growing, flagellated organism with a spiral or S-shaped morphology which infects the lining of the stomach. *H. pylori* is a human gastric pathogen associated with chronic superficial gastritis, peptic ulcer disease, and chronic atrophic gastritis leading to gastric adenocarcinoma. *H. pylori* is one of the most common chronic bacterial infections in humans and is found in over 90% of patients with active gastritis. Current treatment includes triple drug therapy with bismuth, metronidazole, and either tetracycline or amoxicillin which eradicates *H. pylori* in most cases. Problems with triple therapy include patient compliance, side effects, and metronidazole resistance. Alternate regimens of dual therapy which show promise are amoxicillin plus metronidazole or omeprazole plus amoxicillin.

*Streptococcus pneumoniae* is a Gram-positive coccus and one of the most common causes of bacterial pneumonia as well as middle ear infections (otitis media) and meningitis. Each year in the United States, pneumococcal diseases account for approximately 50,000 cases of bacteremia; 3,000 cases of meningitis; 100,000-135,000 hospitalizations; and 7 million cases of otitis media. Pneumococcal infections cause an estimated 40,000 deaths annually in the United States. Children less than 2 years of age, adults over 65 years of age and persons of any age with underlying medical conditions, including, e.g., congestive heart disease, diabetes, emphysema, liver disease, sickle cell, HIV, and those living in special environments, e.g., nursing homes and long-term care facilities, at highest risk for infection.

Drug-resistant *S. pneumoniae* strains have become common in the United States, with many penicillin-resistant pneumococci also resistant to other antimicrobial drugs, such as erythromycin or trimethoprim-sulfamethoxazole.

*Treponema pallidum* is a spirochete which causes syphilis. *T. pallidum* is exclusively a pathogen which causes syphilis, yaws and non-venereal endemic syphilis or pinta. *Treponema pallidum* cannot be grown in vitro and does replicate in the absence of mammalian cells. The initial infection causes an ulcer at the site of infection; however, the bacteria move throughout the body, damaging many organs over time. In its late stages, untreated syphilis, although not contagious, can cause serious heart abnormalities, mental disorders, blindness, other neurologic problems, and death.

Syphilis is usually treated with penicillin, administered by injection. Other antibiotics are available for patients allergic to penicillin, or who do not respond to the usual doses of penicillin. In all stages of syphilis, proper treatment will cure the disease, but in late syphilis, damage already done to body organs cannot be reversed.

*Chlamydia trachomatis* is the most common bacterial sexually transmitted disease in the United States and it is estimated that 4 million new cases occur each year. The highest rates of infection are in 15 to 19 year olds. *Chlamydia* is a major cause of non-gonococcal urethritis (NGU), cervicitis, bacterial vaginitis, and pelvic inflammatory disease (PID). *Chlamydia* infections may have very mild symptoms or no symptoms at all; however, if left untreated *Chlamydia* infections can lead to serious damage to the reproductive organs, particularly in women. Antibiotics such as azithromycin, erythromycin, ofloxacin, amoxicillin or doxycycline are typically prescribed to treat *Chlamydia* infection.

*Bartonella henselae* Cat Scratch Fever (CSF) or cat scratch disease (CSD), is a disease of humans acquired through exposure to cats, caused by a Gram-negative rod originally named *Rochalimaea henselae*, and currently known as *Bartonella henselae*. Symptoms include fever and swollen lymph nodes and CSF is generally a relatively benign, self-limiting disease in people, however, infection with *Bartonella henselae* can produce distinct clinical symptoms in immunocompromised people, including, acute febrile illness with bacteremia, bacillary angiomatosis, peliosis hepatis, bacillary splenitis, and other chronic disease manifestations such as AIDS encephalopathy.

The disease is treated with antibiotics, such as doxycycline, erythromycin, rifampin, penicillin, gentamycin, ceftriaxone, ciprofloxacin, and azithromycin.

*Haemophilus influenzae* (*H. influenza*) is a family of Gram-negative bacteria; six types of which are known, with most *H. influenza*-related disease caused by type B, or "NIB". Until a vaccine for HIB was developed, HIB was a common causes of otitis media, sinus infections, bronchitis, the most common cause of meningitis, and a frequent culprit in cases of pneumonia, septic arthritis (joint infections), cellulitis (infections of soft tissues), and pericarditis (infections of the membrane surrounding the heart). The *H. influenza* type B bacterium is widespread in humans and usually lives in the throat and nose without causing illness. Unvaccinated children under age 5 are at risk for HIB disease. Meningitis and other serious infections caused by *H. influenza* infection can lead to brain damage or death.

*Shigella dysenteriae* (*Shigella* dys.) is a Gram-negative rod which causes dysentary. In the colon, the bacteria enter mucosal cells and divide within mucosal cells, resulting in an extensive inflammatory response. *Shigella* infection can cause severe diarrhea which may lead to dehydration and can be dangerous for the very young, very old or chronically ill. *Shigella* dys. forms a potent toxin (shiga toxin), which is cytotoxic, enterotoxic, neurotoxic and acts as a inhibitor of protein synthesis. Resistance to antibiotics such as ampicillin and TMP-SMX has developed, however, treatment with newer, more expensive antibiotics such as ciprofloxacin, norfloxacin and enoxacin, remains effective.

*Listeria* is a genus of Gram-positive, motile bacteria found in human and animal feces. *Listeria monocytogenes* causes such diseases as listeriosis, meningoencephalitis and meningitis. This organism is one of the leading causes of death from food-borne pathogens especially in pregnant women, newborns, the elderly, and immunocompromised individuals. It is found in environments such as decaying vegetable matter, sewage, water, and soil, and it can survive extremes of both temperatures and salt concentration making it an extremely dangerous food-born pathogen, especially on food that is not reheated. The bacterium can spread from the site of infection in the intestines to the central nervous system and the fetal-placental unit. Meningitis, gastroenteritis, and septicemia can result from infection. In cattle and sheep, *listeria* infection causes encephalitis and spontaneous abortion.

*Proteus mirabilis* is an enteric, Gram-negative commensal organism, distantly related to *E. coli*. It normally colonizes the human urethra, but is an opportunistic pathogen that is the leading cause of urinary tract infections in catheterized individuals. *P. mirabilis* has two exceptional characteristics: 1) it has very rapid motility, which manifests itself as a swarming phenomenon on culture plates; and 2) it produce urease, which gives it the ability to degrade urea and survive in the genitourinary tract.

*Yersinia pestis* is the causative agent of plague (bubonic and pulmonary) a devastating disease which has killed millions worldwide. The organism can be transmitted from rats to humans through the bite of an infected flea or from human-to-human through the air during widespread infection. *Yersinia pestis* is an extremely pathogenic organism that requires very few numbers in order to cause disease, and is often lethal if left untreated. The organism is enteroinvasive, and can survive and propagate in macrophages prior to spreading systemically throughout the host.

*Bacillus anthracis* is also known as anthrax. Humans become infected when they come into contact with a contaminated animal. Anthrax is not transmitted due to person-to-person contact. The three forms of the disease reflect the sites of infection which include cutaneous (skin), pulmonary (lung), and intestinal. Pulmonary and intestinal infections are often fatal if left untreated. Spores are taken up by macrophages and become internalized into phagolysozomes (membranous compartment) whereupon germination initiates. Bacteria are released into the bloodstream once the infected macrophage lyses whereupon they rapidly multiply, spreading throughout the circulatory and lymphatic systems, a process that results in septic shock, respiratory distress and organ failure. The spores of this pathogen have been used as a terror weapon.

*Burkholderia mallei* is a Gram-negative aerobic bacterium that causes Glanders, an infectious disease that occurs primarily in horses, mules, and donkeys. It is rarely associated with human infection and is more commonly seen in domesticated animals.

This organism is similar to *B. pseudomallei* and is differentiated by being nonmotile. The pathogen is host-adapted and is not found in the environment outside of its host. Glanders is often fatal if not treated with antibiotics, and transmission can occur through the air, or more commonly when in contact with infected animals. Rapid-onset pneumonia, bacteremia (spread of the organism through the blood), pustules, and death are common outcomes during infection. The virulence mechanisms are not well understood, although a type III secretion system similar to the one from *Salmonella typhimurium* is necessary. No vaccine exists for this potentially dangerous organism which is thought to have potential as a biological terror agent. The genome of this organism carries a large number of insertion sequences as compared to the related Bukholderia *pseudomallei* (below), and a large number of simple sequence repeats that may function in antigenic variation of cell surface proteins.

*Burkholderia pseudomallei* is a Gram-negative bacterium that causes meliodosis in humans and animals. Meliodosis is a disease found in certain parts of Asia, Thailand, and Australia. *B. pseudomallei* is typically a soil organism and has been recovered from rice paddies and moist tropical soil, but as an opportunistic pathogen can cause disease in susceptible individuals such as those that suffer from diabetes mellitus. The organism can exist intracellularly, and causes pneumonia and bacteremia (spread of the bacterium through the bloodstream). The latency period can be extremely long, with infection preceding disease by decades, and treatment can take months of antibiotic use, with relapse a commonly observed phenomenon. Intercellular spread can occur via induction of actin polymerization at one pole of the cell, allowing movement through the cytoplasm and from cell-to-cell. This organism carries a number of small sequence repeats which may promoter antigenic variation, similar to what was found with the *B. mallei* genome.

*Burkholderia cepacia* is a Gram-negative bacterium composed of at least seven different sub-species, including *Burkholderia multivorans*, *Burkholderia vietnamiensis*, *Burkholderia stabilis*, *Burkholderia cenocepacia* and *Burkholderia ambifaria*. B. cepacia is an important human pathogen which most often causes pneumonia in poeple with underlying lung disease (such as cystic fibrosis or immune problems (such as (chronic granulomatous disease). *B. cepacia* is typically found in water and soil and can survive for prolonged periods in moist environments. Person-to-person spread has been documented; as a result, many hospitals, clinics, and camps for patients with cystic fibrosis have enacted strict isolation precautions *B. cepacia*. Individuals with the bacteria are often treated in a separate area than those without to limit spread. This is because infection with *B. cepacia* can lead to a rapid decline in lung function resulting in death. Diagnosis of *B. cepacia* involves isolation of the bacteria from sputum cultures. Treatment is difficult because *B. cepacia* is naturally resistant to many common antibiotics including aminoglycosides (such as tobramycin) and polymixin B. Treatment typically includes multiple antibiotics and may include ceftazidime, doxycycline, piperacillin, chloramphenicol, and co-trimoxazole.

*Francisella tularensis* was first noticed as the causative agent of a plague-like illness that affected squirrels in Tulare County in California in the early part of the 20th century by Edward Francis. The organism now bears his namesake. The disease is called tularemia and has been noted throughout recorded history. The organism can be transmitted from infected ticks or deerflies to a human, through infected meat, or via aerosol, and thus is a potential bioterrorism agent. It is an aquatic organism, and can be found living inside protozoans, similar to what is observed with *Legionella*. It has a high infectivity rate, and can invade phagocytic and nonphagocytic cells, multiplying rapidly. Once within a macrophage, the organism can escape the phagosome and live in the cytosol.

The invention also finds application in treating oral bacterial pathogens, such as Gram-negative bacteria *Porphyromonas gingivalis, Treponema denticola, Tannerella forsythia, Aggregatibacter actinomycetemcomitans, Campylobacter rectus, Prevotella intermedia, Prevotella nigrescens, Fusobacterium nucleatum, Eikenella corrodens* or *Capnocytophaga ochracea*. Therefore, the methods of the invention may be applied to treat intra-oral bacteria, including intra-oral antibiotic resistant bacteria.

The present invention also finds application in the treatment of peritonitis. Peritonitis is inflammation of the membranes of the abdominal wall and organs. The abdominal organs, such as the stomach and liver, are wrapped in a thin, tough membrane called the visceral peritoneum. The abdominal walls are similarly lined (parietal peritoneum). A protective layer of fat contained in a membrane (the omentum) sits between the organs and the abdominal wall. Lubricating fluid allows all these membranes to slide smoothly over each other. The main function of the peritoneum is to permit free movement of the internal organs during digestion. Peritonitis is inflammation of the peritoneum caused by bacterial infection.

Peritonitis may be diagnosed in a subject via a number of tests, including (a) Physical examination—the abdomen is hard and painful. There are no bowel movements or sounds; (b) Signs of shock—including low blood pressure, abnormal pulse rate and pale skin; (c) Blood tests—to check for which bacteria are responsible; (d) X-rays—of the abdomen; (e) Laparoscopy—a slender tube is inserted through an abdominal incision and the insides examined; and/or (f) Peritoneal fluid culture—a sample of fluid is taken and examined for signs of infection.

The invention also finds use in veterinary applications. A healthy microflora in the gastro-intestinal tract of livestock is of vital importance for health and corresponding production of associated food products. As with humans, the gastrointestinal tract of a healthy animal contains numerous types of bacteria (i.e., *E. coli, Pseudomonas aeruginosa* and *Salmonella* spp.), which live in ecological balance with one another. This balance may be disturbed by a change in diet, stress, or in response to antibiotic or other therapeutic treatment, resulting in bacterial diseases in the animals generally caused by bacterias such as *Salmonella, Campylobacter*, Enterococci, Tularemia and *E. coli*. Bacterial infection in these animals often necessitates therapeutic intervention, which has treatment costs as well being frequently associated with a decrease in productivity.

As a result, livestock are routinely treated with antibiotics to maintain the balance of flora in the gastrointestinal tract. The disadvantages of this approach are the development of antibiotic resistant bacteria and the carry over of such antibiotics and the resistant bacteria into resulting food products for human consumption.

The term "treat", "treating" or "treatment" as used herein also refers to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infections, or (iv) suppress the clinical manifestation of a bacterial infection, or (v) suppress the manifestation of adverse symptoms of the bacterial infections. Further, the terms "treating" and "treatment" may include one or more of, ameliorating a symptom of a bacterial infection in a subject, blocking or ameliorating a recurrence of a symptom of a bacterial infection in a subject, decreasing in severity and/or frequency a symptom of a bacterial infection in a subject, stasis, decreasing, or inhibiting growth of a vegetative form of bacteria in a subject, inhibiting bacterial sporulation in a subject, inhibiting activation of a bacterial spore in a subject, inhibiting germination of a bacterial spore in a subject, and inhibiting outgrowth of a bacterial spore in a subject. Treatment means ameliorating, blocking, reducing, decreasing or inhibiting by about 1% to about 100% versus a subject to which a star shaped peptide polymer or composition of the present invention has not been administered. Preferably, the ameliorating, blocking, reducing, decreasing or inhibiting is 100%, 99%, 98%, 97%, 96%, 95%, 90%, 80%, 70%, 60%, 50%, 40%, 30%, 20%, 10%, 5% or 1% versus a subject to which star shaped peptide polymer or composition of the present invention has not been administered.

Successful treatment may generally mean improvement in any symptoms associated with or caused by a Gram-positive or Gram-negative bacterial infection for example may refer to an improvement in any of the following: fever, inflammation, swelling, vomiting, fatigue, cramping, coughing, sneezing, respiratory illness, diarrhea, meningitis, headaches, joint pain, body aches, blisters, rashes, nausea, chills, dizziness, drowsiness, sleeplessness, gagging, skin irritation, excessive mucus production (e.g. in the eyes, gastrointestinal tract, sinuses, or respiratory system), ulcers, gastrointestinal discomfort, skin loss, hair loss, necrosis, and organ dysfunction. Improvements in any of these symptoms or in the bacterial infection or conditions described herein can be readily assessed according to standard methods and techniques known in the art. The population of subjects treated by the method of the disease includes subjects suffering from the undesirable condition or disease, as well as subjects at risk for development of the condition or disease.

As used herein, the terms "inhibit", "inhibiting" and "inhibition" have their ordinary and customary meanings, and include one or more of inhibiting growth or a function of bacteria, inhibiting growth of a vegetative form of bacteria, inhibiting a function of a vegetative form of bacteria, inhibiting propagation of bacteria, inhibiting bacterial sporulation, inhibiting activation of a bacterial spore, inhibiting germination of a bacterial spore, and inhibiting outgrowth of a bacterial spore. Such inhibition is an inhibition of about 1% to about 100% of the particular activity versus the activity in a subject to which a star shaped peptide polymer or composition of the present invention has not been administered. Preferably, the inhibition is an inhibition of 100%, 99%, 98%, 97%, 96%, 95%, 90%, 80%, 70%, 60%, 50%, 40%, 30%, 20%, 10%, 5% or 1% of the activity versus a subject to which a star shaped peptide polymer or composition of the present invention has not been administered. As used herein, "spore" refers to both the conventionally used terms "spore" and "endospore."

As used herein, the terms "preventing" and "prevention" have their ordinary and customary meanings, and includes one or more of preventing colonization of bacteria in a subject, preventing an increase in the growth of a population of bacteria in a subject, preventing activation, germination or outgrowth of bacterial spores in a subject, preventing sporulation of bacteria in a subject, preventing development of a disease caused by bacteria in a subject, and preventing symptoms of a disease caused by bacteria in a subject. As used herein, the prevention lasts at least about 0.5, 1, 2, 3, 4, 5, 6, 7, 10, 12, 15, 20, 25, 30, 35, 40 or more days after administration of a star shaped peptide polymer or composition of the present invention.

As used herein, "prophylaxis" includes inhibiting the development of a productive or progressive infection by bacteria in a subject, where the prophylaxis lasts at least about 0.5, 1, 2, 3, 4, 5, 6, 7, 10, 12, 15, 20, 25, 30, 35, 40 or more days after administration of a star shaped peptide polymer or composition of the present invention Inhibition against development of a productive or progressive infection by a bacterial infection means that the severity of a bacterial infection in a subject is reduced by about 1% to about 100% versus a subject to which a star shaped peptide polymer or composition of the present invention has not been administered. Preferably, the reduction in severity is a 100%, 99%, 98%, 97%, 96%, 95%, 90%, 80%, 70%, 60%, 50%, 40%, 30%, 20%, 10%, 5% or 1% reduction in severity. The severity of an infection may be based on the amount of bacteria present in a subject, the length of time that the bacteria can be detected in a subject, and/or the severity of a symptom of a bacterial infection, among other factors.

As used herein, the term "contacting" is meant to broadly refer to bringing a bacterial cell and a star shaped peptide polymer of the present invention into sufficient proximity that the star shaped peptide polymer can exert an effect on the bacterial cell. The star shaped peptide polymer may be transported to the location of the bacterial cell, or the star shaped peptide polymer may be situated in a location to which the bacterial cell travels or is brought into contact. The skilled artisan will understand that the term "contacting" includes physical interaction between a star shaped peptide polymer and a bacterial cell, as well as interactions that do not require physical interaction.

Typically, a therapeutically effective dosage is formulated to contain a concentration (by weight) of at least about 0.1% up to about 50%, and all combinations and sub-combinations of ranges therein. The compositions can be formulated to contain one or more star shaped peptide polymers of the invention and/or anti-bacterial compounds in a concentration of from about 0.1 to less than about 50%, for example, about 49, 48, 47, 46, 45, 44, 43, 42, 41 or 40%, with concentrations of from greater than about 0.1%, for example, about 0.2, 0.3, 0.4 or 0.5%, to less than about 40%, for example, about 39, 38, 37, 36, 35, 34, 33, 32, 31 or 30%. Exemplary compositions may contain from about 0.5% to less than about 30%, for example, about 29, 28, 27, 26, 25, 25, 24, 23, 22, 21 or 20%, with concentrations of from greater than about 0.5%, for example, about 0.6, 0.7, 0.8, 0.9 or 1%, to less than about 20%, for example, about 19, 18, 17, 16, 15, 14, 13, 12, 11 or 10%. The compositions can contain from greater than about 1% for example, about 2%, to less than about 10%, for example about 9 or 8%, including concentrations of greater than about 2%, for example, about 3 or 4%, to less than about 8%, for example, about 7 or 6%. The active agent can, for example, be present in a concentration of about 5%. In all cases, amounts may be adjusted to compensate for differences in amounts of active ingredients actually delivered to the treated cells or tissue.

In any aspect of the invention, the amount or concentration of star shaped peptide polymer, anti-bacterial compound or composition of the present invention administered to the subject or contacted to the bacteria does not cause any clinically significant reduction in viability of mammalian cells. Viability of mammalian cells may be determined using a method as described herein, for example in Example 5. Typically, the mammalian cells are those in proximity to the bacteria or on the subject, or which may come in contact with the star shaped peptide polymer, anti-bacterial compound or composition of the present invention during administration.

Pharmaceutical compositions may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. Other routes of administration include intra-oral, intra-sulcular and intra-periodontal pocket. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydropropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as *arachis* oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or *arachis* oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monoleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Compositions of the invention may be formulated for local or topical administration, such as for topical application to the skin. Formulations for topical administration typically comprise a topical vehicle combined with active agent(s), with or without additional optional components.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both nonvolatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylceilulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the bacterial infection to be treated or prevented.

In another embodiment there is provided a kit or article of manufacture including one or more pharmaceutical compositions as described above.

In other embodiments there is provided a kit for use in a therapeutic or prophylactic application mentioned above, the kit including:
a container holding a pharmaceutical composition of the invention;
a label or package insert with instructions for use.

In certain embodiments the kit may contain one or more further active principles or ingredients for treatment of a bacterial infection.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic or prophylactic composition can be used to treat a bacterial infection according to any method described herein.

The present invention also provides a kit when used in any method described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from a bacterial infection described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic, prophylactic or pharmaceutical composition. In one embodiment, the device is a syringe. The device may hold 1-2 mL of the therapeutic composition. The therapeutic or prophylactic composition may be provided in the device in a state that is ready for use or in a state requiring mixing or addition of further components.

It will be understood that the invention disclosed and defined in this specification extends to all alternative combinations of two or more of the individual features mentioned or evident from the text or drawings. All of these different combinations constitute various alternative aspects of the invention.

EXAMPLES

The following non-limiting examples include the use of specific star shaped peptide polymers of the invention which are described herein as SNAPPs (Structurally Nanoengineered Antimicrobial Peptide Polymers).

Example 1

Methods

Bacterial Cell Culture.

Freeze-dried cultures of *Escherichia coli* (*E. coli*, ATCC 25922), *Klebsiella pneumoniae* (*K. pneumoniae*, ATCC 13883), *Pseudomonas aeruginosa* (*P. aeruginosa*, ATCC 47085), *Acinetobacter baumannii* (*A. baumannii*, ATCC 19606), colistin and multidrug-resistant (CMDR) *A. baumannii* (FADDI-AB156), and CMDR *P. aeruginosa* (FADDI-PA067) were grown aerobically and maintained by passage at ambient temperature on horse blood agar (10% v/v defibrinated horse blood, 4.4% w/v Oxoid Blood Agar Base No. 2). Overnight cultures were made from transferring a colony (ca. half a loop) from the agar plates to culture tubes containing sterilized Luria-Bertani broth (LB, 1% w/v Bacto™ Tryptone, 1% w/v NaCl, 0.5% w/v Oxoid Yeast Extract) (20 mL). Bacterial cultures were incubated overnight at 37° C. with aeration and without agitation, with the exception of the two *P. aeruginosa* strains (ATCC 47085 and FADDI-PA067) which were cultured at 37° C. with aeration and agitation (150 rpm). On the next day, for *E. coli, K. pneumonia, P. aeruginosa* (ATCC 47085), and CMDR *P. aeruginosa* (FADDI-PA067), small aliquots (i.e., 0.5-3 mL) were taken from the culture tubes, further diluted with LB (20 mL), and incubated for 3-4 h at 37° C. with aeration before use. All bacterial cultures were cultured without agitation, with the exception of *P. aeruginosa* ATCC 47085 and FADDI-PA067 which were cultured with shaking at 150 rpm. For *A. baumannii*, an aliquot of 0.5 mL was taken from the overnight culture tube, further diluted with LB (200 mL), and incubated overnight at 37° C. with aeration before use.

Bacterial Cell Counting.

A Cell Lab Quanta SC MPL flow cytometer (Beckman Coulter) equipped with a 100 W stabilized mercury arc lamp with wavelengths of 365, 404, and 435 nm, and a 488 nm diode laser was used to count the number of bacterial cells prior to use in assays. The fluorescence from SYTO® 9 was measured through a 525-nm band-pass filter (Fluorescent Channel 1, FL-1), and the red emission of PI was measured with a 670-nm long pass filter (Fluorescent Channel 3, FL-3). Cells were diluted with saline using an appropriate dilution factor and incubated with SYTO® 9 and PI (i.e., 1 mL cell solution to 1 µL of each dye). SYTO® 9 stains the nucleic acids in all cells, while PI stains the nucleic acids in cells with damaged membranes. Using the Cell Lab Quanta SC software, the number of viable cells/mL (SYTO® 9-positive, PI-negative) was obtained.

In Vitro Antimicrobial Experiments.

Bacterial cells (which gave an optical density reading of ~0.7 at 650 nm) were diluted to $2.5 \times 10^6$ cells/mL in MHB and 100 µL of the bacteria solution was added to each well containing either MHB or the test compound(s) at the desired concentrations (100 µL). The 96-well plate was then incubated at 37° C. for 1.5 or 3 h. For each well, microbial solution was diluted with saline (0.9% NaCl solution) using an appropriate dilution factor and placed on a LB agar plate (LB broth containing 15 g/L Oxoid Blood Agar Base No. 2). For *E. coli*, *K. pneumoniae*, and *A. Baumannii* (ATCC 19606 and FADDI-AB156), the agar plates were incubated overnight at room temperature, and then at 37° C. with aeration for 2 h. For *P. Aeruginosa* (ATCC 47085 and FADDI-PA067), the agar plates were incubated at 37° C. with aeration. The number of colony-forming units (CFU) was counted and expressed as CFU/mL. Positive controls consisting of cells without any treatment were used. For MBC determination, concentration-killing curves were plotted with CFU/mL as a function of compound concentration and linear regression analysis was used to determine the lowest concentration (MBC) at which the CFU/mL becomes zero. A minimum of two independent experiments (biological replicates) of the assay were conducted and three technical replicates were used in each experiment. Data is expressed as mean±standard deviation (SD) and analysed using student's t-test.

Statistical Analysis.

Data obtained were determined to be normally distributed. Homogeneity of variances was assessed using the Levene's test (SPSS for Windows, version 12). Statistical analysis was also performed using a one-way classification of ANOVA and student's t-test (two-tailed), where differences were regarded as statistically significant with probability $P<0.05$.

Quantifying Synergy Using the Bliss Independence and Highest Single Agent (HSA) Model.

The Bliss Independence and HSA models were used to calculate drug synergism. Hegreness et al. Proc. Natl. Acad. Sci. U.S.A. 105, 13977-13981 (2008); and Brynildsen et al. Nat. Biotechnol. 31, 160-165 (2013). With the Bliss Independence model, synergism was calculated using the formula, $BIC_{AB}=A+B-AB$ (1), where A and B are the effects of the two drugs in isolation and $BIC_{AB}$ is the combined effect of the two drugs as predicted by the Bliss Independence model. Synergy is observed if $C_{AB}$, which is the experimentally determined combined effect of the two drugs, is greater than $BIC_{AB}$. In the HSA model, if $C_{AB}$ is greater than the greater of A and B, $C_{AB}>\max(A, B)$, synergy is observed. The quantitative effect of the compounds when administered alone (i.e., A and B) or in combination (i.e., $C_{AB}$) was defined as the fractional reduction of the population, $R=1-CFU_t/CFU_0$, where $CFU_t$ is the CFU/mL measured after treatment, and $CFU_0$ is the CFU/mL measured before treatment.

Membrane disruption assays using flow cytometry. Briefly, the membrane disruption assay was conducted as previously described (O'Brien-Simpson et al. PLoS One 11, e0151694 (2016). *E. coli* cells (100 µL, final concentration of $2.5\times10^6$ cells/mL) were added to S16 (100 µL, final concentration of 0.5×, 1×, or 2×MBC) in MHB in a 96-well plate. The plate was then incubated at 37° C. for 90 min. A 50 µL aliquot was taken from each well, transferred to a second 96-well plate and 100 µL of saline and dye mixture (i.e., saline with 0.1% of SYTO® 9 and 0.1% of PI) was added. Each well in the second 96-well plate was analyzed with a Cell Lab Quanta SC MPL flow cytometer. On the two-parameter dot plots obtained, the x-axis represents fluorescent channel 1 (FL1), which measures the fluorescent emission of SYTO® 9. The y-axis represents fluorescent channel 3 (FL3), which measures the fluorescent emission of PI. The % of cells with intact membranes (PI-negative) and cells with compromised membranes (PI-positive) were determined. Positive controls containing cells alone were incorporated. Two independent runs of the assay were conducted and two replicates were used in each run.

Membrane Potential Assay.

Membrane potential was determined by flow cytometry using a BacLight Bacterial Membrane Potential Kit (Invitrogen). When at low concentrations, the dye $DiOC_2(3)$ exhibits green fluorescence in all bacterial cells. The fluorescence shifts towards red emission as the dye molecules become more concentrated and self-associate in healthy cells that are maintaining a membrane potential. The experiments were carried out as previously reported (Lam, S. J. et al. Nat. Microbiol. 1, 10.1038/nmicrobio1.2016.162 (2016)). Data is representative of two independent assays completed in duplicates.

Mammalian Cell Culture.

Rat hepatoma cells (H4IIE) were cultivated in DMEM medium (supplemented with 10% FBS, 1× GlutaMAX™, and 1× penicillin-streptomycin) in a humidified atmosphere containing 5% $CO_2$ at 37° C. Cells were seeded in a T75 flask (ca. $3\times10^6$ cells/ml) and passaged twice a week prior to performing the subsequent cell viability studies.

Apoptosis/Necrosis Assay.

Adherent H4IIE cells (obtained from the ATCC, and throughout the course of the study cells were checked for *mycoplasma* contamination using *Mycoplasma* stain kit, Myc1, Sigma) were grown to 80% confluence and trypsinised prior to assay. H4IIE cells were chosen for this study as they are standard cell lines used in toxicity studies. Cells were diluted 1:2 with 'complete' DMEM and seeded in a 24-well plate (1 mL per well). The cells were incubated at 37° C. in 5% $CO_2$ for 24 h until ca. 95% confluence. The medium was removed. The test compounds (S16 and $AgNO_3$) were prepared at the desired concentrations and 200 µL aliquots of each were added to the cells, after which the cells were incubated at 37° C. in 5% $CO_2$ for 90 min. The cells were then harvested and all well contents were transferred to round-bottomed polypropylene tubes (5 mL). The cells were washed with cold DPBS, then stained with YO-PRO®-1 and PI (0.2 mL from a stock solution, whereby both dyes were diluted 1:1000 in cold DPBS, per well), and incubated on ice for 20 to 30 min. The cells were analyzed by flow cytometry (Cytomics FC 500 MPL System). Standard compensation was performed using single-colour stained cells. Negative controls using untreated cells were included. Two independent runs of the assay were conducted and two replicates were used in each run for each test compound and concentration.

Materials.

Sodium chloride (NaCl, Chem-Supply), potassium chloride (KCl, Chem-Supply), sodium phosphate dibasic ($Na_2HPO_4$, Chem-Supply), potassium phosphate monobasic ($KH_2PO_4$, 99%, Aldrich), D-(+)-glucose solution (100 g/L, Aldrich), thiourea (>99%, Aldrich), ampicillin (Aldrich), gentamicin solution (50 g/L, Adrich), doxycycline hyclate (>98%, Aldrich), tobramycin (Aldrich), imipenem monohydrate (Aldrich), silver nitrate ($AgNO_3$, >99%, Aldrich), and penicillin-streptomycin (Aldrich) were used as received. Dulbecco's Modified Eagle Medium (DMEM, GIBCO Cat. No. 11995), fetal bovine serum (FBS, GIBCO Cat. No. 10099), GlutaMAX™ supplement (100×, GIBCO Cat. No. 35050), MEM non-essential amino acids (MEM NEAA, 100×, GIBCO Cat. No. 11140), Dulbecco's Phosphate Buffered Saline (DPBS, GIBCO 14190), 0.05% trypsin-EDTA (1×, GIBCO Cat. No. 25300), SYTO® 9 green fluorescent nucleic acid stain, and propidium iodide (PI) were purchased from Invitrogen and used as received. Defibrinated horse blood was obtained from Commonwealth Serum Laboratories (CSL) Melbourne. Mueller-Hinton Broth (MHB) (CM0405), Blood Agar Base No. 2 (CM0271), and Yeast Extract (LP0021) were purchased from Oxoid. Bacto™ Tryptone was purchased from BD Biosciences. BacLight Bacterial Membrane Potential Kit (Invitrogen) was used to conduct the membrane potential assay. Vybrant® Apoptosis Assay Kit #4 (YO-PRO®-1/PI, Invitrogen) was used to perform the apoptosis/necrosis assay. 96-well cell culture plates were used for cell culture.

Example 2

In Vitro Screening for SNAPP-Antibiotic Synergism

In this study, all experiments were conducted using a model SNAPP in the form of a nano-sized, 16-arm star-shaped peptide polymer, S16, comprising lysine and valine amino acid residues (FIG. 1). The synthesis and characterization of S16 are as described in Lam et al. Nature Microbiology. (2016) Sep. 12; 1:16162. The mechanism of action of S16 appears to involve outer membrane (OM) destabilization, unregulated ion movement across the cytoplasmic membrane (CM), and induction of the apoptotic-like death pathway, ultimately resulting in cell lysis. As the antimicrobial action is multi-modal where SNAPPs are able to act on multiple cellular targets but different from antibiotic targets (a prerequisite of an antibiotic adjuvant), the inventors hypothesize that S16 could potentially interact synergistically with different classes of antibiotics either by combined multi-modal antimicrobial activities and/or by potentiating or restoring the activity of the conventional antibiotic by acting as an adjuvant.

Figure 2:
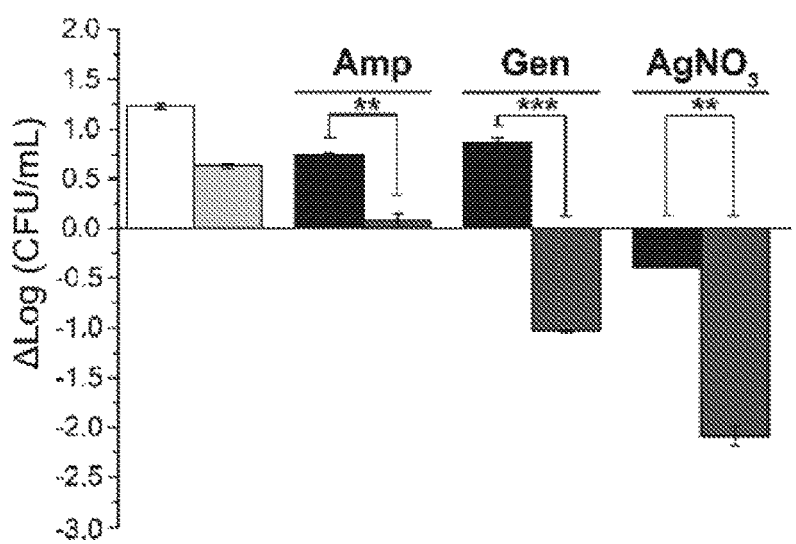
FIG. 2. Screening analysis for synergistic S16-antibiotic pairs. a-f, Log change in colony-forming units (CFU)/mL of *E. coli* (a), *K. pneumoniae* (b), *P. aeruginosa* (c), CMDR *P. aeruginosa* (d), *A. baumannii* (e) and CMDR *A. baumannii* (f) from time zero after treatment for 3 h with S16, a range of antibiotics, and combinations of S16 with the respective antibiotics, with all compounds at their MBC50. All data are expressed as mean±standard deviation as indicated by the error bars (n=3). *P<0.001, P<0.05, Student's t test. Amp=ampicillin, Gen=gentamicin, Dox=doxycycline, Tob=tobramycin, Imi=imipenem.
Figure 2:
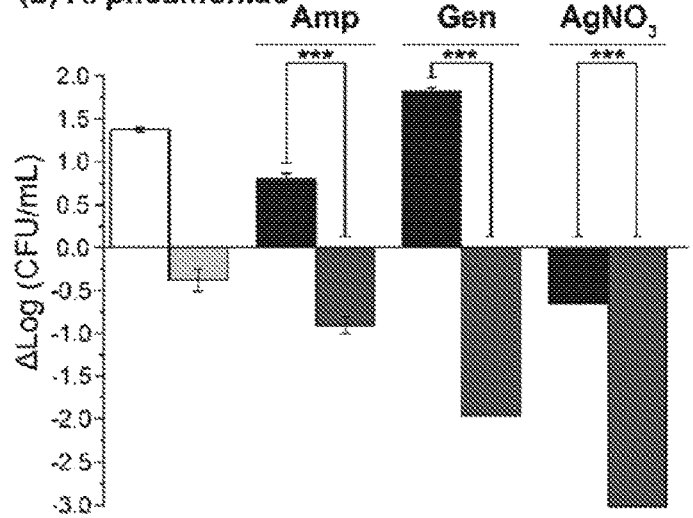
Figure 2:
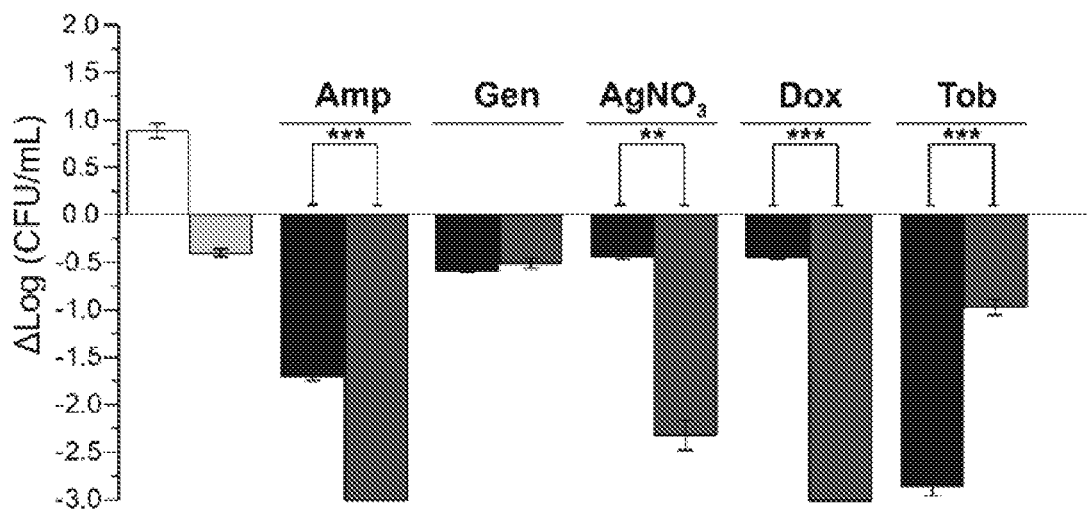
Figure 2:
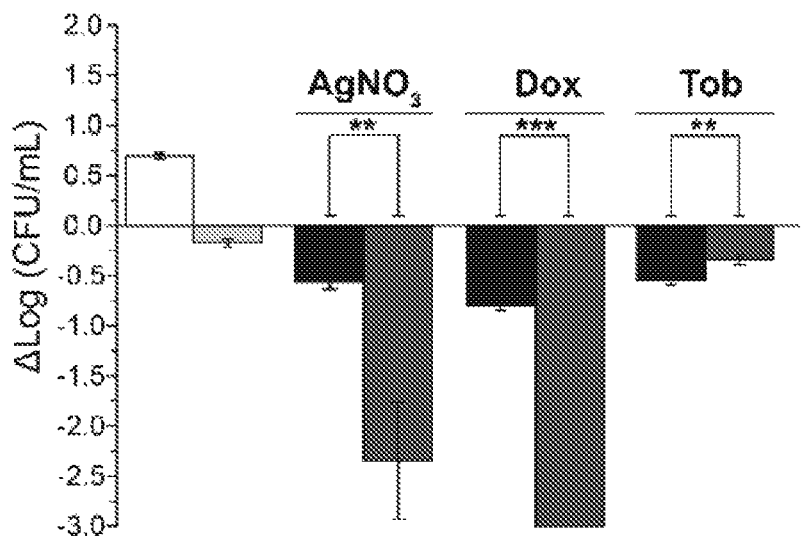
Figure 2:
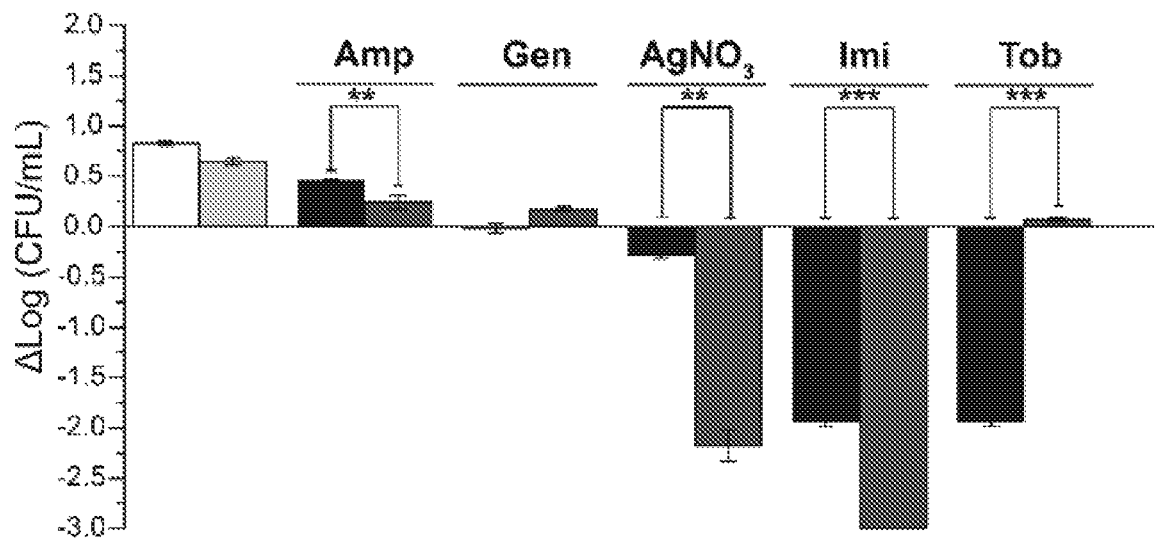
Figure 2:
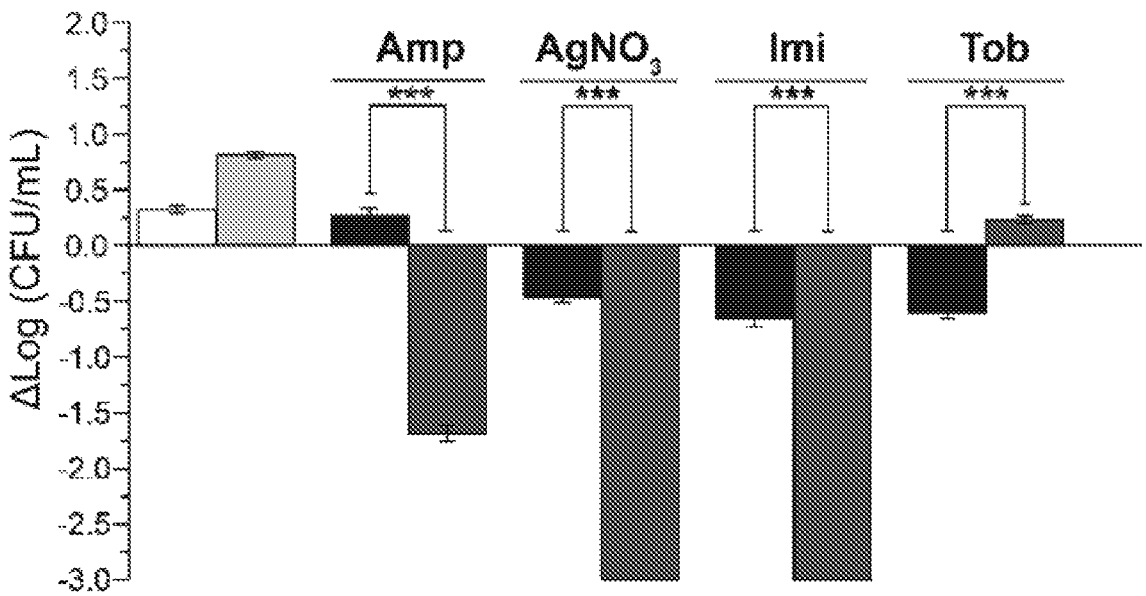

As an initial step, S16 was screened in combination with a model β-lactam (ampicillin), an aminoglycoside (gentamicin), and silver (in the form of dissolved ions, Ag$^+$, from AgNO$_3$) for synergy against wild-type strains of *Escherichia coli, Klebsiella pneumoniae, P. aeruginosa*, and *A. baumannii*, all of which are clinically-relevant Gram-negative pathogens. The antibacterial activities of each compound are reported as minimum bactericidal concentrations (MBCs) in Table 3. MBC determination was selected as the method of choice to evaluate antimicrobial efficacies as it quantifies the concentration needed to cause bacterial cell death and hence is a more stringent approach than the minimum inhibitory concentration (MIC) analysis which measures growth inhibition (Pankey, G. A. & Sabath, L. D. Clin. Infect. Dis. 38, 864-870 (2004)). To determine the extent of synergy between a SNAPP S16-antibiotic pair, bacterial cells were treated with sub-lethal concentrations of the compounds (i.e., MBC50 which is one-half of the MBC), either individually or in combination based on the method reported by Collins and co-workers (Morones-Ramirez et al. Sci. Transl. Med. 5, 190ra81 (2013)). The change in the log of colony-forming unit (CFU) per mL, log(CFU/mL), compared to the untreated control at time zero was monitored after 1.5 (FIG. 5) and 3 h (FIG. 2).

At t=3 h, significantly enhanced antimicrobial activity (as indicated by increased bacterial cell death) was observed against the four bacterial species tested when S16 was co-administered with either ampicillin or AgNO$_3$ ($P<0.05$), compared to when the compounds were administered alone (FIG. 2a-c, e). When S16 and gentamicin were co-administered, enhanced efficacy was only observed against *E. coli* and *K. pneumoniae* ($P<0.001$) (FIG. 2a-b). The effects of co-administration were further investigated by combining S16 with other antibiotics, such as doxycycline (which is used in the treatment of respiratory infections caused by *P. aeruginosa*), imipenem (a common treatment option for serious infections caused by *A. baumannii*), and tobramycin (an aminoglycoside commonly used to treat Gram-negative infections such as those caused by *P. aeruginosa* and *A. baumannii*). Increased efficacy was observed for S16-doxycycline and S16-imipenem combinations against *P. aeruginosa* and *A. baumannii*, respectively ($P<0.001$) (FIGS. 2c and e). Interestingly, antagonism between S16 and tobramycin was indicated when tested against *P. aeruginosa* and *A. baumannii*, as demonstrated by the reduction in bactericidal efficacy compared to when the antibiotic was administered alone (FIGS. 2c and e).

For *P. aeruginosa* and *A. baumannii*, CMDR clinical isolates were also tested in addition to the wild-type strains (FIGS. 2d and f; refer to Tables 4 and 5 for antibiograms). Enhanced antimicrobial activity was demonstrated by the co-administration of S16 with either AgNO$_3$ or doxycycline against CMDR *P. aeruginosa* ($P<0.05$), and S16 with ampicilin, AgNO$_3$ or imipenem against CMDR *A. baumannii* ($P<0.001$). Similar to that observed for wild-type *P. aeruginosa* and A. baumnanii, the combination of S16 and tobramycin against the CMDR isolates was antagonistic. The pairing of S16-ampicillin against CMDR *P. aeruginosa* was deemed redundant and hence not investigated as the bacterial strain used is already highly susceptible to ampicillin (MBC<1.4 μM). Further, we also excluded S16-gentamicin from further investigations with the CMDR isolates as this pairing did not result in any significant change in activity against the wild types compared to the case when the compounds were administered alone.

Figure 5:
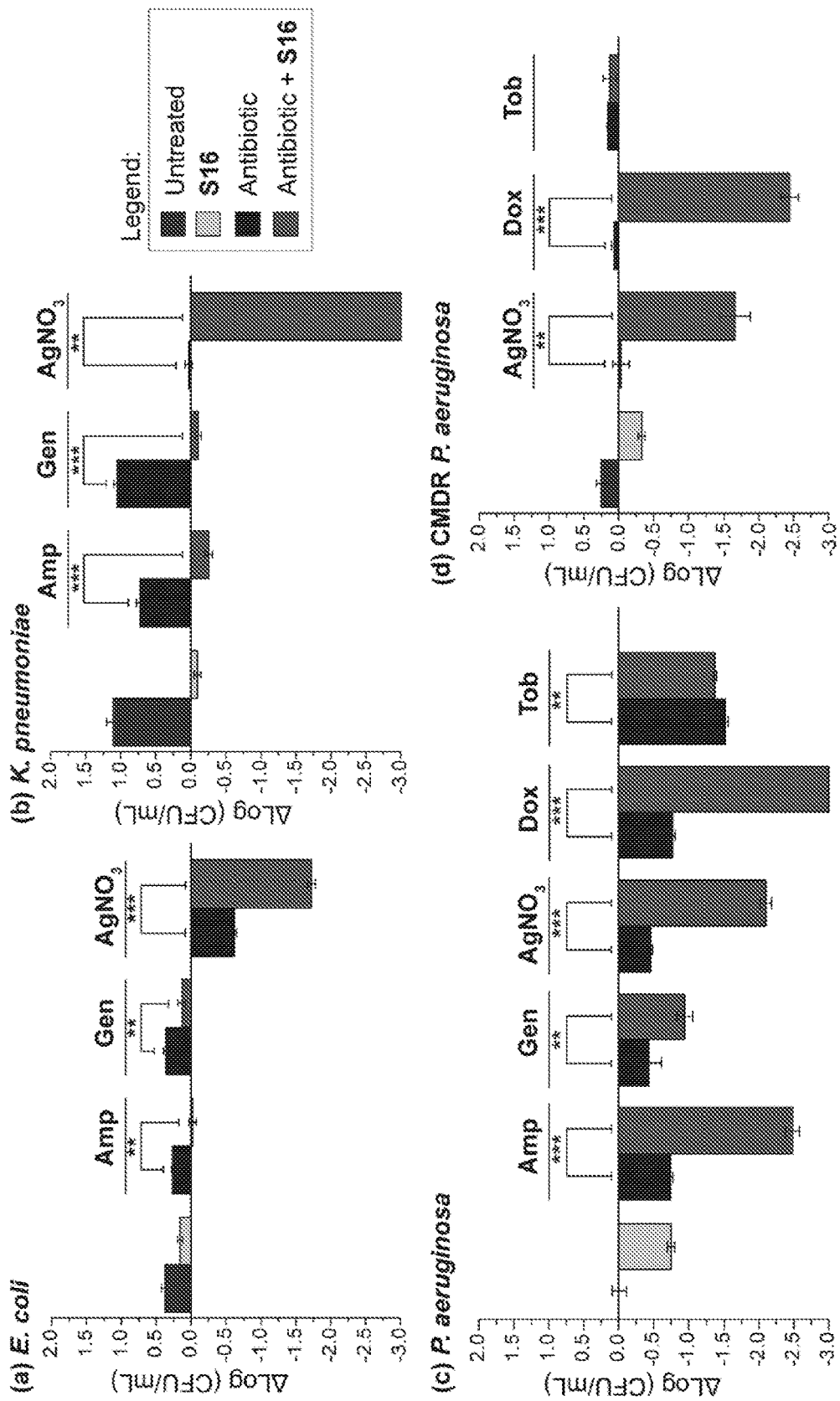
FIG. 5. Screening analysis for synergistic S16-antibiotic pairs. a-f, Log change in colony-forming units (CFU)/mL of *E. coli* (a), *K. pneumoniae* (b), *P. aeruginosa* (c), CMDR *P. aeruginosa* (d), *A. baumannii* (e) and CMDR *A. baumannii* (f) from time zero after treatment for 1.5 h with S16, a range of antibiotics, and combinations of S16 with the respective antibiotics, with all compounds at their MBC50. All data are expressed as mean±standard deviation as indicated by the error bars (n=3). *P<0.001, P<0.05, Student's t test.
Figure 5:
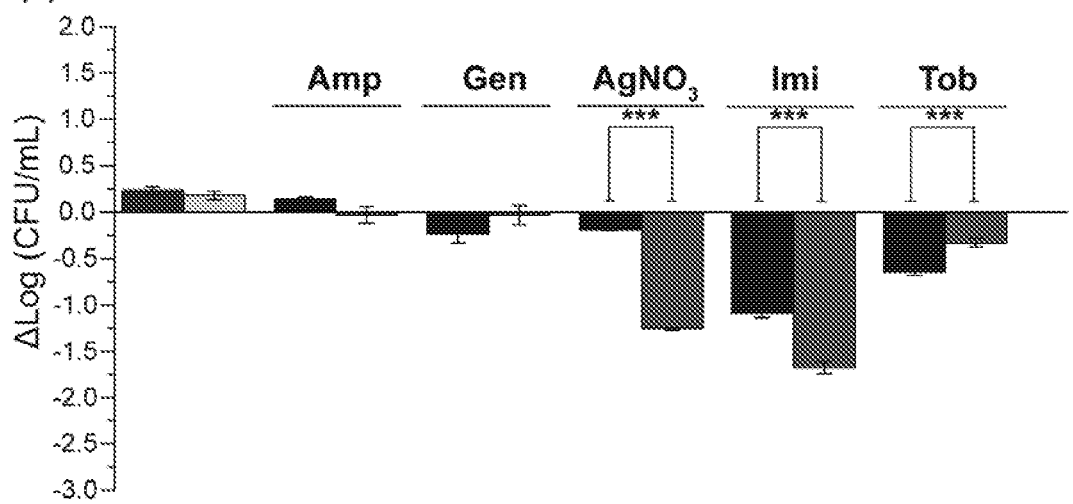
Figure 5:
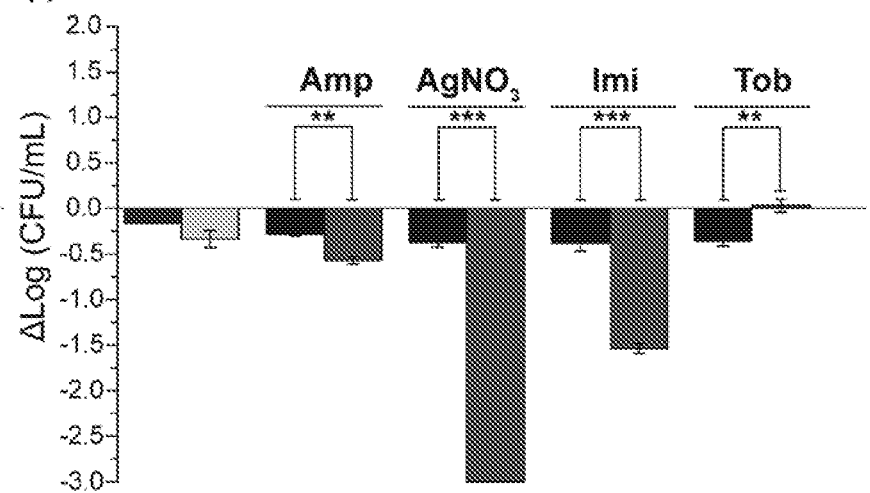

It is noteworthy that at a shorter incubation time of 1.5 h, the results obtained were similar to those obtained at t=3 h, albeit with less pronounced effects for the cases where S16-antibiotic combination therapy resulted in an increase in efficacy (FIG. 5). An exception was noted where the co-administration of S16 with gentamicin resulted in enhancement in efficacy against *P. aeruginosa* at t=1.5 h ($P<0.05$), but not at t=3 h. This could be explained by the growth of the remaining viable cells when incubated beyond 1.5 h with S16-gentamicin, resulting in an increase in cell counts at t=3 h compared to that at 1.5 h.

Example 3

Evaluation of the Degree of Synergy

Following the observations made from the screening analysis (FIG. 2), the Bliss Independence and Highest Single Agent (HSA) models (see 'Methods' for details) were used to evaluate the degree of synergy based on the 3 h time point, which would quantitatively determine if the antimicrobial effect between two compounds was synergistic. The results are shown in Table 1. The two models, while independent of each other, were found to produce identical evaluations of synergism, except in one case where the Bliss Independence model computed functional synergy between S16 and gentamicin against *A. baumannii*, while the HSA model indicated otherwise. As the HSA model has been reported to be a more stringent method to evaluate drug synergism, the aforementioned pair was determined to be non-synergistic against *A. baumannii*. Based on the models, S16 was found to synergize with Ag$^+$ (from AgNO$_3$) against all six bacterial species tested. The combination of S16 with either doxycycline or imipenem was also found to be synergistic against all bacterial species tested (wild-type and CMDR *P. aeruginosa* for S16-doxycycline; wild-type and CMDR *A. baumannii* for S16-imipenem). The antimicrobial effects resulting from the S16-ampicillin combination were found to be synergistic against *K. pneumoniae, P. aeruginosa*, and CMDR *A. baumannii*. While FIG. 2 indicated statistically significant enhancement of activity (P<0.05) against *E. coli* and *A. baumannii* following co-administration of S16 and ampicillin, the antimicrobial effects were not sufficient to satisfy the criteria for synergism based on either the Bliss Independence or HSA models. In these cases, the interactions between the two compounds against the aforementioned bacterial species were deemed 'additive' (i.e., an effect equal to the sum of the treatments) at most. As expected, the S16-tobramycin pairing was found to be non-synergistic against the bacterial species tested.

Figure 6:
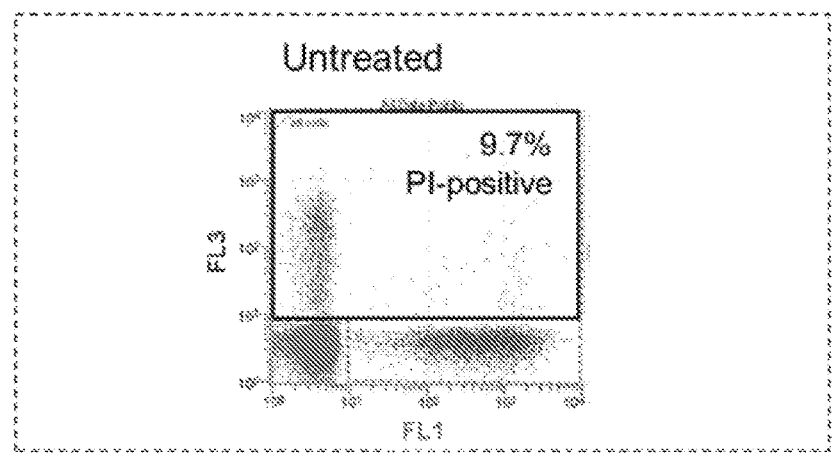
FIG. 6. Effects of SNAPPs on bacterial membranes. a, Uptake of propidium iodide (PI) by *E. coli* after treatment with SNAPP S16. *E. coli* cells were incubated with S16 for 90 min at 0.5×, 1×, and 2×its MBC. After incubation the cells were stained with SYTO® 9 and PI nucleic acid dyes and subjected to flow cytometric analysis. Cells were determined to be 'PI-positive', and hence membrane-disrupted, if fluorescence emitted is captured by FL3 (indicated by the black box). Controls whereby no S16 was added (0 μM) were included. b, Membrane potential flow cytometric dot plots obtained after incubating *E. coli* with 30 μM DiOC$_2$(3) for 1 h in the presence/absence of CCCP (a proton ionophore), and SNAPP S16 at 0.5×, 1×, and 2× its MBC. The controls where CCCP was either absent (−CCCP) or present (+CCCP) represent the normal membrane potential state and fully depolarized state for *E. coli*, respectively. A flow cytometry gate (black polygon) was drawn in each panel to indicate the position of the viable bacteria in the absence of CCCP or SNAPP.
Figure 6:
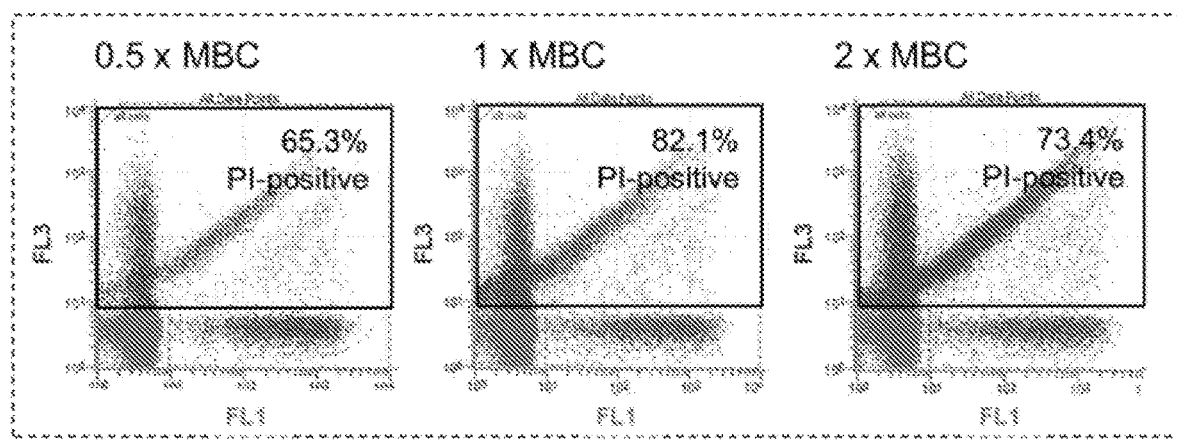

Out of the 23 different S16-antibiotic-bacteria combinations investigated, 15 were found to exhibit synergism between S16 and the antibiotic used. SNAPP S16 adjuvanticity may be attributed to its ability to disrupt the bacterial membrane, as shown by the dose-dependent increase in the uptake of the membrane-impermeable propidium iodide (PI) dye (FIG. 6). Furthermore, the treatment of bacterial cells with S16 also led to membrane potential alterations, causing the formation of mixed hyperpolarized and depolarized bacterial cell populations (FIG. 6). Bacterial membrane disruption and membrane potential dissipation have been reported to result in the abrogation of efflux pumps and the enhanced uptake of antibiotics. As the active efflux of antibiotics is one of the major mechanisms for antibiotic resistance, we propose that the membrane perturbations caused by SNAPPs may account for their adjuvant role in potentiating antibiotic activity against CMDR bacterial species. Further, we postulate that the excellent synergism between S16 and $Ag^+$ may be explained by the similarities in the antimicrobial mechanism of both compounds, where treatment of Gram-negative bacteria with either SNAPPs or $Ag^+$ resulted in increased reactive oxygen species (ROS) production and membrane permeability, as previously reported. This postulation is consistent with previous studies, where high functional synergy between two antimicrobial compounds was attributed to mechanistic analogy between the compounds.

On the other hand, the general lack of synergism between S16 and the aminoglycoside antibiotics tested, as exemplified by the indifference shown by S16-gentamicin towards half of the bacterial species tested and the antagonism between S16 and tobramycin against all four bacterial species tested, may be attributed to the competition for cationic binding sites on the lipopolysaccharide (LPS), which is found on the OM of Gram-negative bacteria. As binding with the LPS layer is the first step in the mode of action of both S16 and aminoglycosides in general, the reduction in available binding sites could lead to a reduction in efficacy for each compound and this may result in the lack of synergy or, in some cases, antagonism as observed. It was noted that the degree of synergy for the pairing between S16 and ampicillin or gentamicin seemed to vary depending on which bacterial species was tested. This could possibly be related to the differences in composition and properties of the outer membranes of Gram-negative bacteria.

Example 4

Effects of Antibiotic Concentration on Synergism

Figure 3:
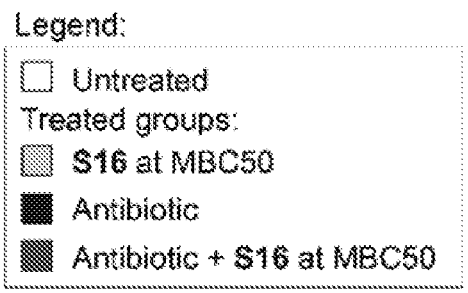
FIG. 3. a-e, Log change in CFU/mL of various bacterial species from time zero after treatment for 3 h with S16 at its MBC50 and a range of antibiotics at the indicated concentrations. The synergistic pairs investigated are S16-ampicillin (Amp) against *P. aeruginosa* (a), 516-AgNO$_3$ (Ag$^+$) against CMDR *P. aeruginosa* (b), S16-doxycycline (Dox) against CMDR *P. aeruginosa* (c), 516-AgNO$_3$ (Ag$^+$) against CMDR *A. baumannii* (d), and S16-imipenem (Imi) against CMDR *A. baumannii* (e). All data are expressed as mean±standard deviation as indicated by the error bars (n=3). *P<0.001, P<0.05, Student's t test.
Figure 3:
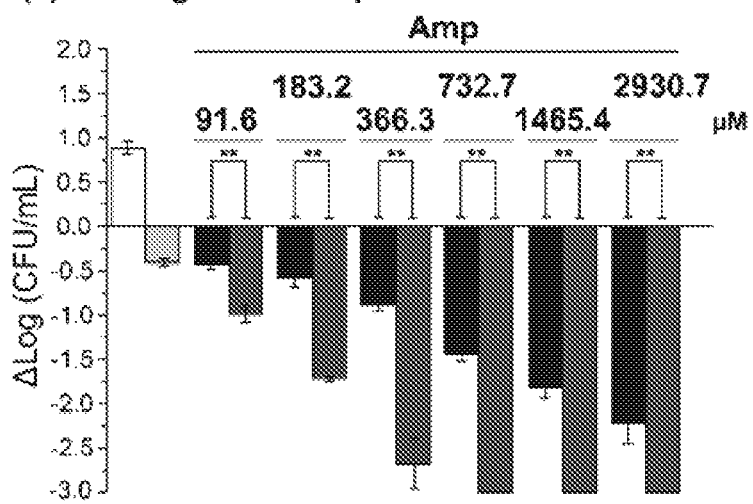
Figure 3:
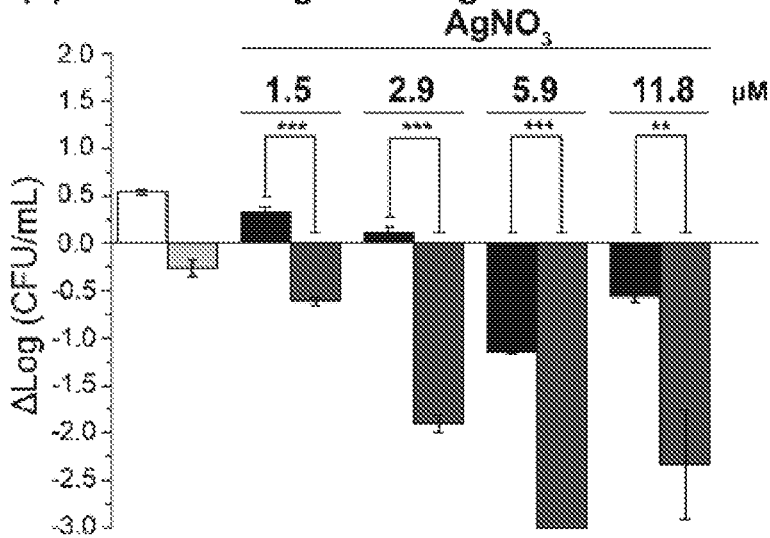
Figure 3:
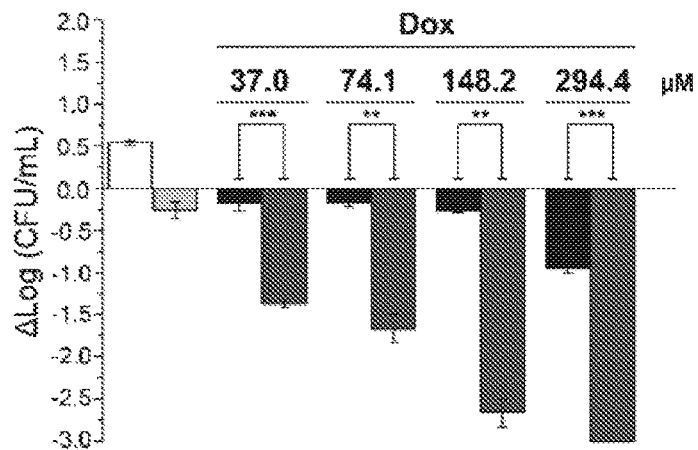
Figure 3:
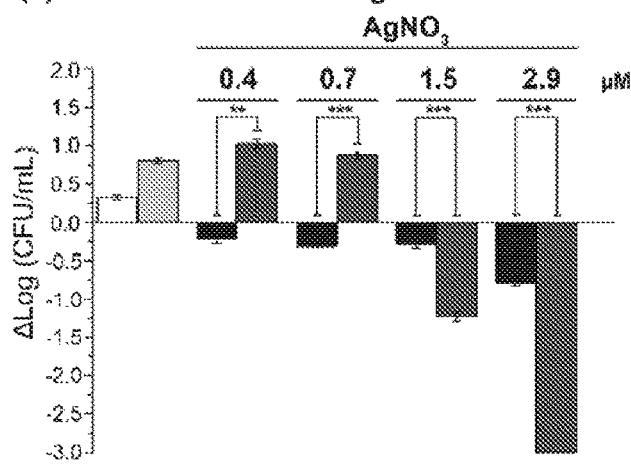
Figure 3:
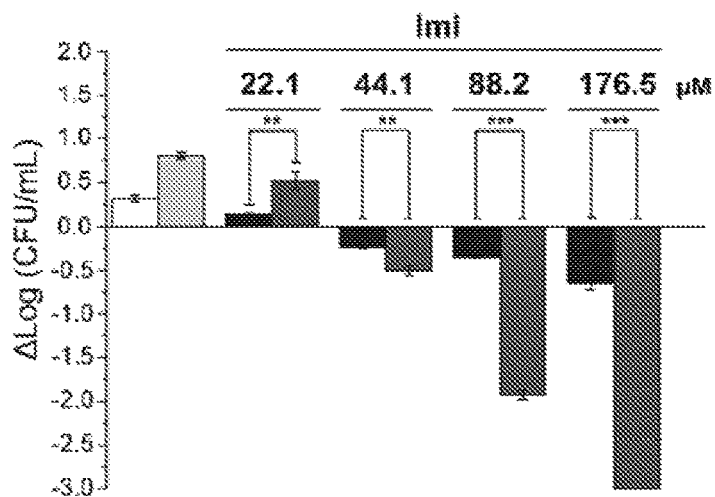
Figure 7:
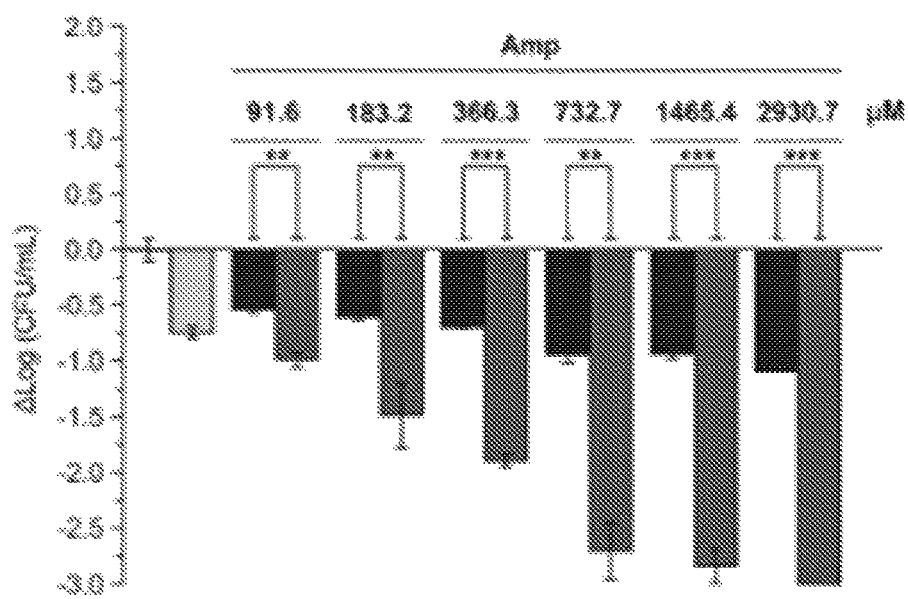
FIG. 7. a-e, Log change in CFU/mL of various bacterial species from time zero after treatment for 1.5 h with S16 at its MBC50 and a range of antibiotics at the indicated concentrations. The synergistic pairs investigated are S16-ampicillin (Amp) against *P. aeruginosa* (a), S16-AgNO$_3$ (Ag$^+$) against CMDR *P. aeruginosa* (b), S16-doxycycline (Dox) against CMDR *P. aeruginosa* (c), S16-AgNO$_3$ (Ag$^+$) against CMDR *A. baumannii* (d), and S16-imipenem (Imi) against CMDR *A. baumannii* (e). All data are expressed as mean±standard deviation as indicated by the error bars (n=3). *P<0.001, P<0.05, Student's t test.
Figure 7:
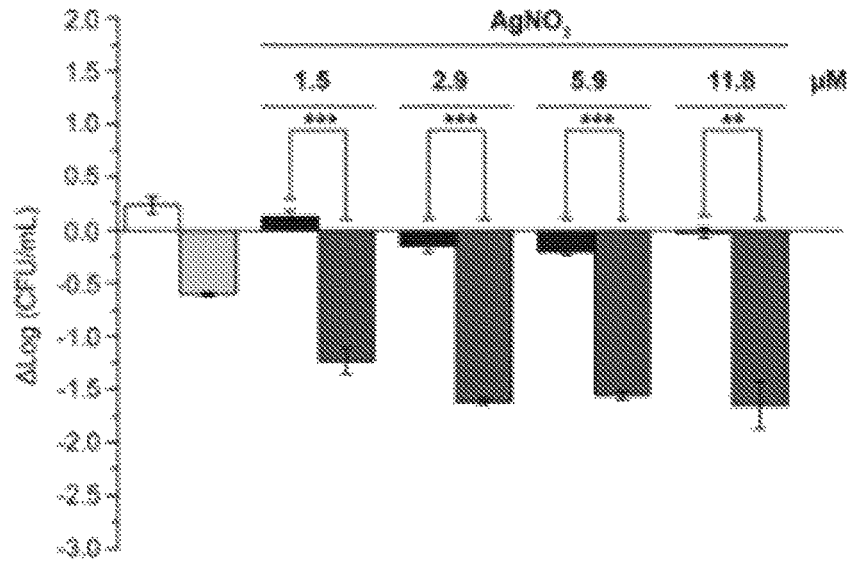
Figure 7:
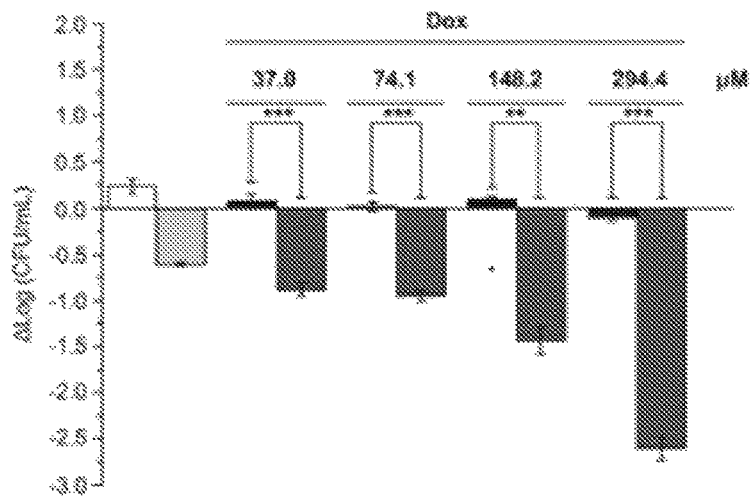
Figure 7:
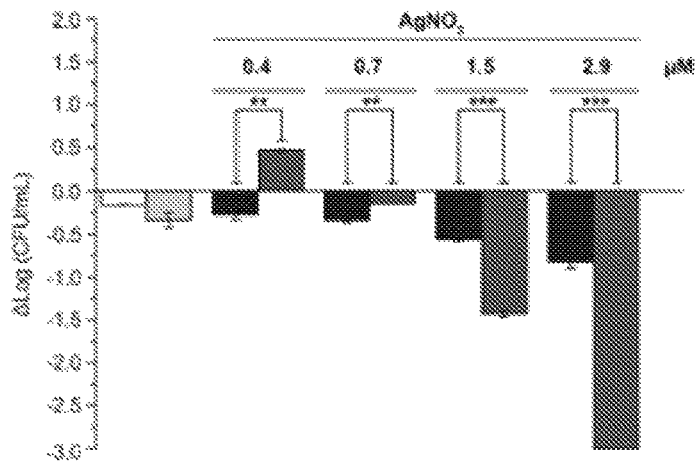
Figure 7:
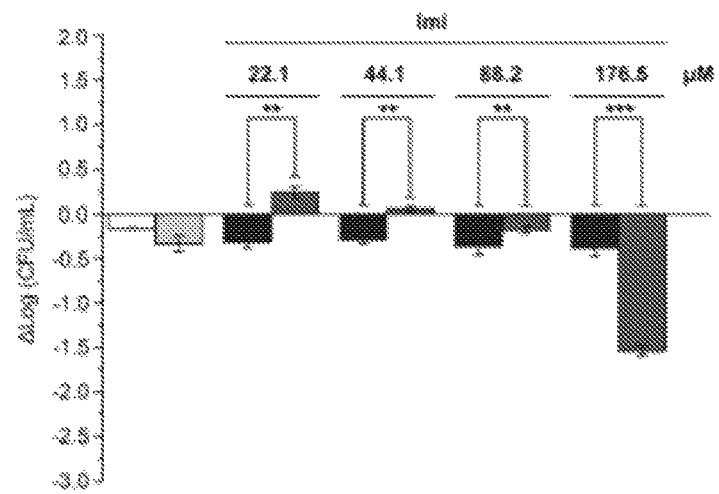
Figure 8:
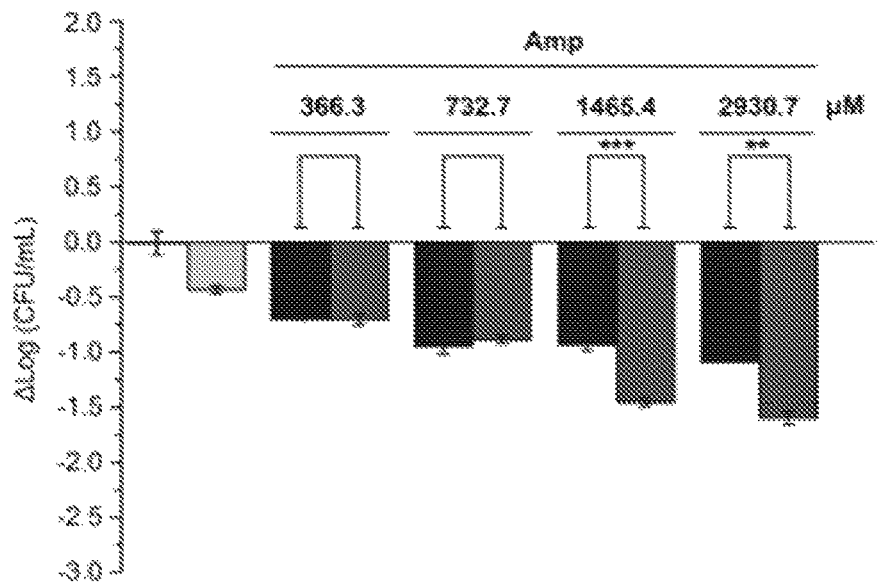
FIG. 8. a-e, Log change in CFU/mL of various bacterial species from time zero after treatment for 1.5 h with S16 at its MBC25 and a range of antibiotics at the indicated concentrations. The synergistic pairs investigated are S16-ampicillin (Amp) against *P. aeruginosa* (a), 516-AgNO$_3$ (Ag$^+$) against CMDR *P. aeruginosa* (b), S16-doxycycline (Dox) against CMDR *P. aeruginosa* (c), 516-AgNO$_3$ (Ag$^+$) against CMDR *A. baumannii* (d), and S16-imipenem (Imi) against CMDR *A. baumannii* (e). All data are expressed as mean±standard deviation as indicated by the error bars (n=3). *P<0.001, P<0.05, Student's t test.
Figure 8:
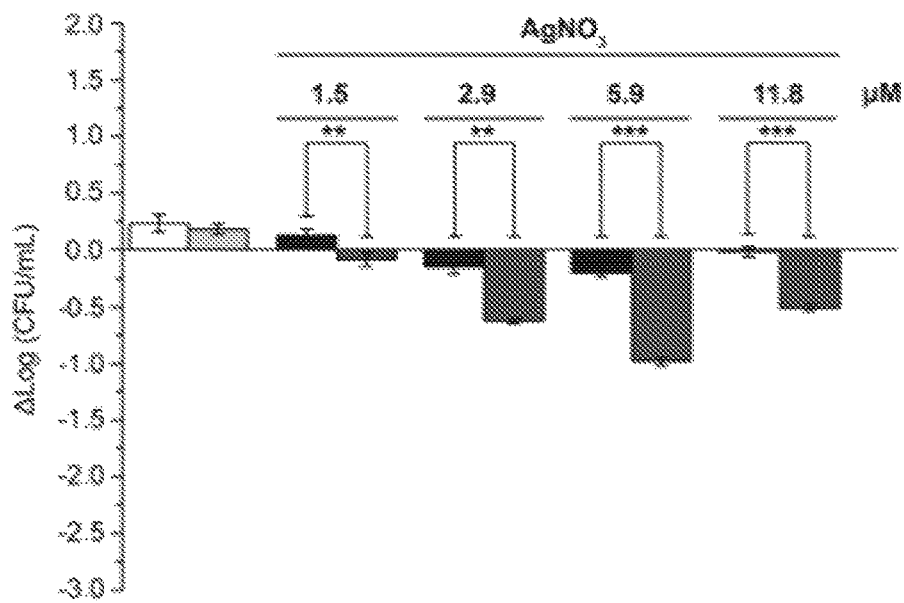
Figure 8:
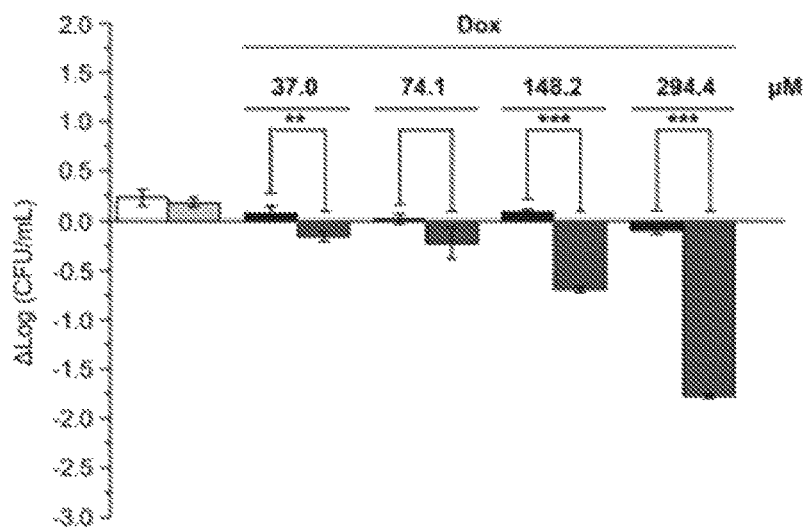
Figure 8:
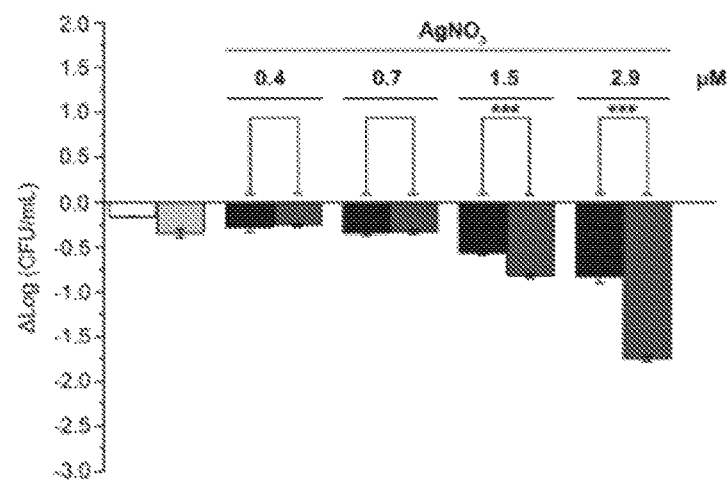
Figure 8:
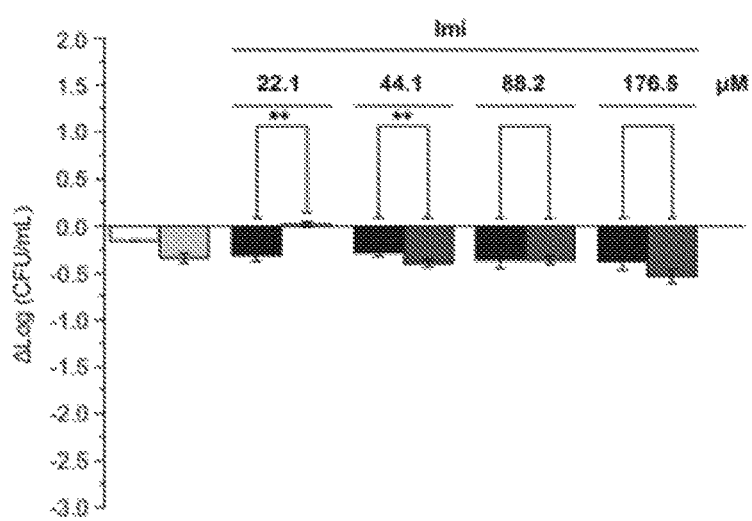
Figure 9:
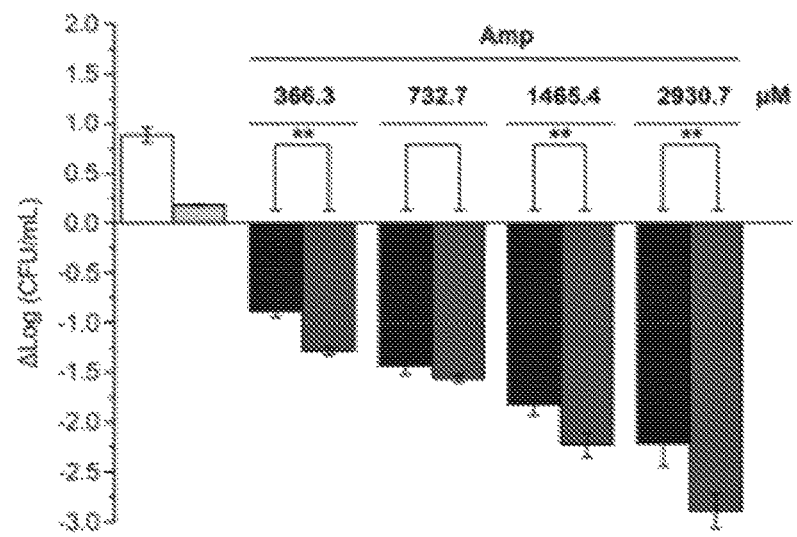
FIG. 9. a-e, Log change in CFU/mL of various bacterial species from time zero after treatment for 3 h with S16 at its MBC25 and a range of antibiotics at the indicated concentrations. The synergistic pairs investigated are S16-ampicillin (Amp) against *P. aeruginosa* (a), 516-AgNO$_3$ (Ag$^+$) against CMDR *P. aeruginosa* (b), S16-doxycycline (Dox) against CMDR *P. aeruginosa* (c), 516-AgNO$_3$ (Ag$^+$) against CMDR *A. baumannii* (d), and S16-imipenem (Imi) against CMDR *A. baumannii* (e). All data are expressed as mean±standard deviation as indicated by the error bars (n=3). *P<0.001, P<0.05, Student's t test.
Figure 9:
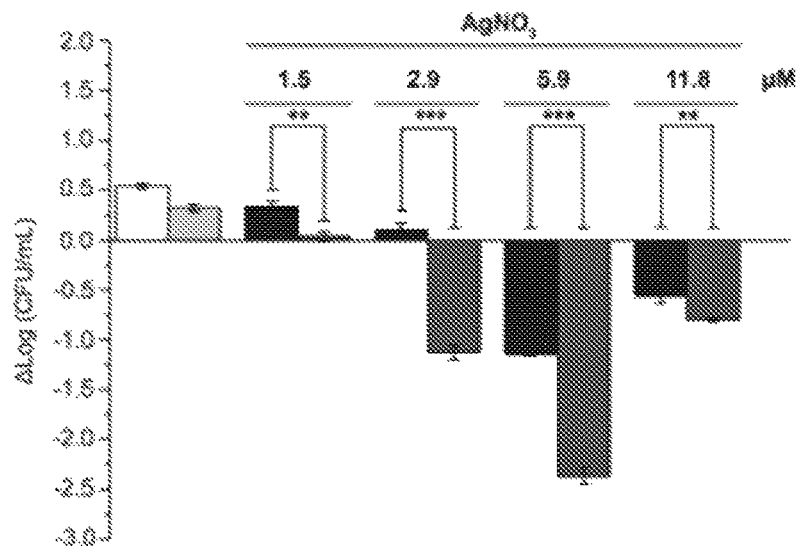
Figure 9:
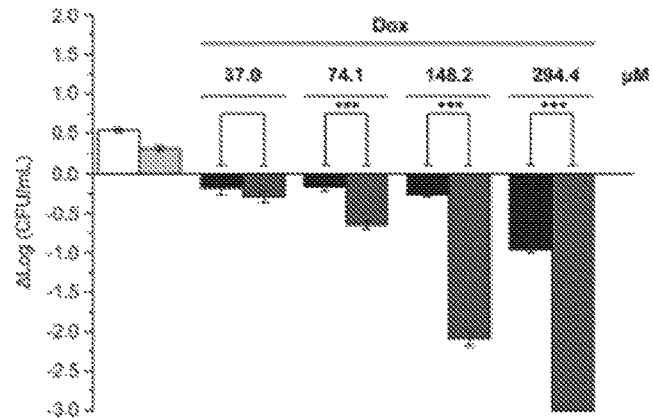
Figure 9:
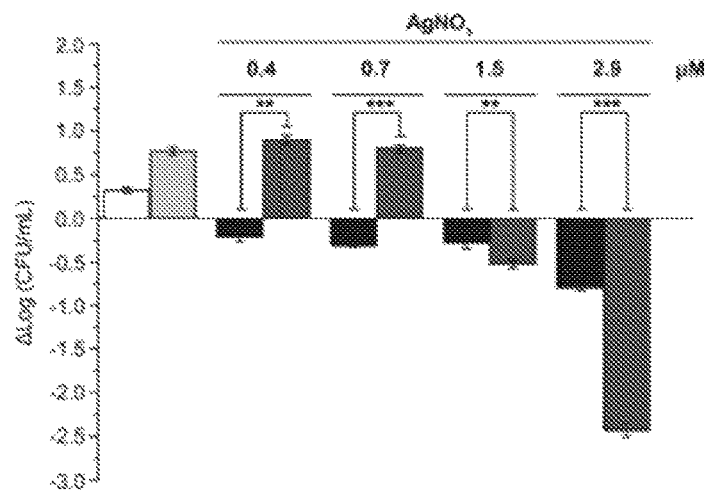
Figure 9:
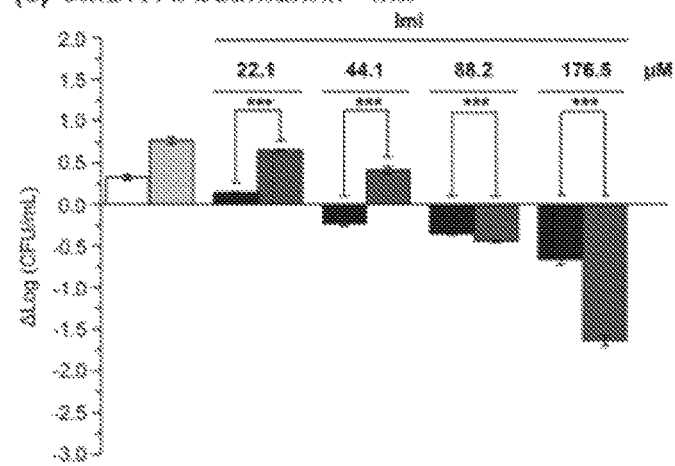

Next, the inventors selected five S16-antibiotic-bacteria combinations, where the bacterial species was found to be resistant to the respective antibiotic, to investigate the effects of antibiotic concentration on S16-drug synergism. The combinations chosen were S16-ampicillin against wild-type ampicillin-resistant *P. aeruginosa*, S16-$Ag^+$ against CMDR isolates of *P. aeruginosa* and *A. baumannii*, S16-doxycycline against CMDR *P. aeruginosa*, and S16-imipenem against CMDR *A. baumannii*. In each case, the S16 concentration was fixed at its MBC50. Based on FIG. 3, increased cell death (P<0.05) following combination treatments for 3 h was observed for all cases even when the antibiotic concentration was reduced below the MBC50 of the antibiotic. For treatments against wild-type and CMDR *P. aeruginosa* in particular, the antibiotic concentrations could be reduced by 8 to 32-fold from the MBC50 of the antibiotic when administered alone (FIG. 3*a-c*). However, it should be noted that a decreasing trend in the extent of efficacy enhancement was observed as the antibiotic concentration used was lowered. The experiments were also conducted in different variations, where either the S16 concentration was decreased to its MBC25 or the incubation time was shortened to 1.5 h (FIGS. 7-9). Generally, enhanced antimicrobial activity (P<0.05) was demonstrated in most cases following reductions in antibiotic concentration, although the effects were less prominent.

Based on the results shown in FIG. 3, the MBCs of the antibiotics when co-administered with S16, hereby denoted as $MBC_{eff}$, were taken as the effective dose that resulted in at least a 2-log reduction in bacterial cell counts. These values were computed and listed in Table 2. By comparing the $MBC_{eff}$ of each antibiotic with its original MBC when administered alone (see Table 3 for the latter), we were able to obtain the extent of reduction in the antibiotic concentration afforded as a result of the S16-antibiotic synergism (Table 2). Notably, while ampicillin on its own is ineffective against *P. aeruginosa* (MBC>5.86 mM), its activity can be improved by synergistic interactions with S16 which results in more than 16-fold reduction in MBC. Further, 3.7 to 6.5-fold reductions in MBC resulting from synergy with S16 were obtained for doxycycline and imipenem which possess poor efficacy against CMDR *P. aeruginosa* and CMDR *A. baumannii*, respectively, when administered alone. The ability of SNAPP S16 to synergize with imipenem, a type of carbapenem from the β-lactam class, is encouraging, as carbapenems have been viewed as the only available treatment option against many severe infections caused by MDR bacteria and the emergence of carbapenem resistance among Gram-negative pathogens have been reported.

Example 5

Mammalian Cell Toxicity Evaluation

Figure 4:
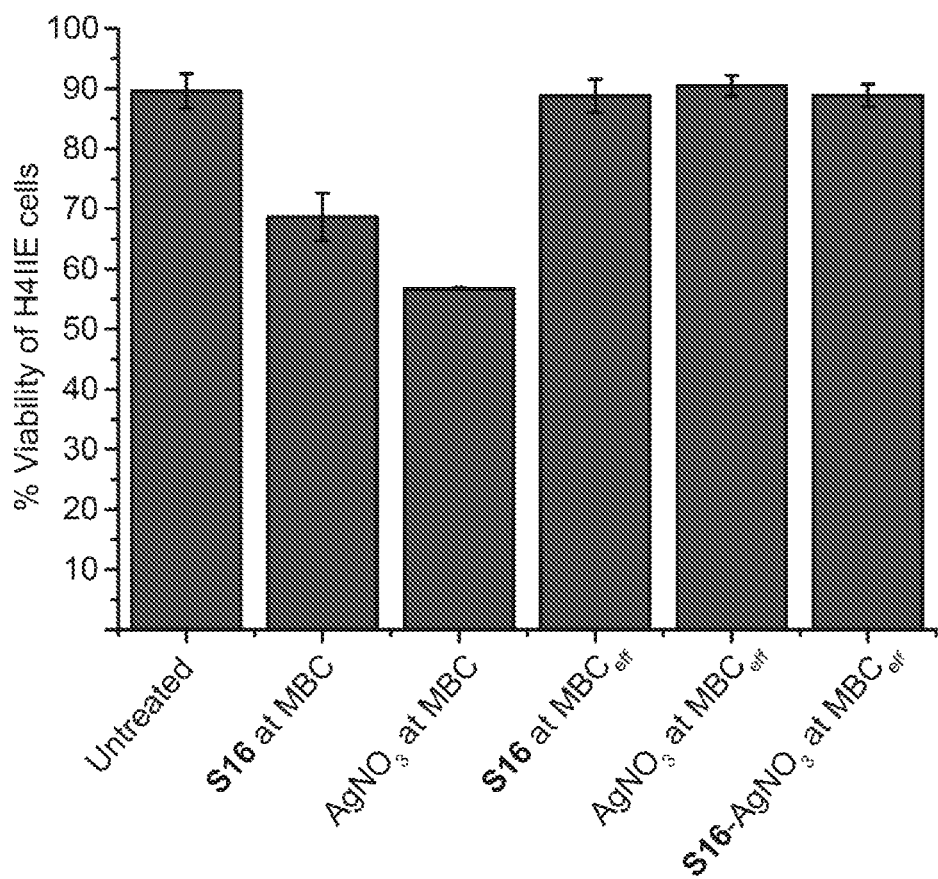
FIG. 4. Effect of SNAPP S16-Ag$^+$ synergistic pair on mammalian cell viability. Percent viability of rat hepatoma (H4IIE) cells after treatment with S16, Ag$^+$ (AgNO$_3$), and co-administration of S16 and Ag$^+$ at the indicated concentrations. MBC=1.6 μM for S16 and 10.6 μM for Ag$^+$; MBC$_{eff}$=0.8 μM for S16 and 2.9 μM for Ag$^+$. Note that the MBC and MBC$_{eff}$ values were taken based on the in vitro activities of the compounds against MDR *A. baumannii*. All data are expressed as mean±standard deviation as indicated by the error bars (n=4).

The use of antibiotics has been linked to adverse side effects on the human body, such as neurotoxicity. Silver ion ($Ag^+$), while approved by the U.S. Food and Drug Administration (FDA) as a topical antimicrobial, has been widely acknowledged to display dose-dependent cytotoxicity which prohibits its systemic use. The inventors hypothesize that synergistic therapy could help to reduce the toxicity of such antibiotics as the effective antibiotic concentrations required would be reduced. As a proof-of-concept study, we selected the S16-$Ag^+$ pair that was found to be synergistic against CMDR *A. baumannii* as a model due to the inherent toxicity of $Ag^+$. The viability of a model mammalian cell line—rat hepatoma H4IIE cells—was evaluated 90 min after incubation with S16, $Ag^+$ or a combination of S16 and $Ag^+$ via an apoptosis/necrosis assay (FIG. 4). When treatment with either S16 or $Ag^+$ was applied at a dose equivalent to their MBC dose, H4IIE cell viability was reduced by 21 and 33%, respectively, compared to the untreated control. However, when the cells were treated with a cocktail of S16 and $Ag^+$ (at dosages equivalent to their $MBC_{eff}$), negligible effect on cell viability was observed as compared to untreated cells.

Since S16 and Ag$^+$ possess synergistic antimicrobial activities, the dosages of S16 and Ag$^+$ required for combination therapy are significantly reduced compared to the dosages required in monotherapy (i.e., 2-fold for S16 and 3.7-fold for Ag$^+$). We suggest that the synergistic antimicrobial effects of SNAPPs with antibiotics could potentially be harnessed as a strategy to formulate highly potent but safe antimicrobial combinations for treatment.

In conclusion, the inventors have demonstrated the ability of SNAPPs to synergize with antibiotics from different classes (i.e., β-lactams, tetracyclines and Ag$^+$) against a range of clinically-relevant Gram-negative pathogens, including CMDR clinical isolates. Notably, excellent synergy was demonstrated by a model SNAPP with Ag$^+$ against all bacterial species tested, which was attributed to the mechanistic similarities of both compounds in terms of ROS production and membrane disruption. The synergism between SNAPPs and ampicillin or gentamicin was found to be species-dependent, whereas highly synergistic interactions were observed for the combination of SNAPPs with either doxycycline or imipenem against the CMDR bacterial species. We also showed that antibiotic doses could be reduced by 3.7 to 16-fold from their original effective dose when co-administered with SNAPPs, while retaining significantly enhanced efficacy against the drug-resistant bacterial species. Furthermore, it was indicated that the use of SNAPPs as an antibiotic adjuvant could mitigate the toxic side-effects of certain antimicrobials. This study demonstrates the potential of the synergistic co-administration of SNAPPs and antibiotics as a novel treatment method against infections caused by drug-resistant Gram-negative bacteria.

Example 6

In Vivo Synergy of SNAPP with Imipenem.

All experiments involving animals were performed according to protocols approved by the University of Melbourne Biochemistry and Molecular Biology, Dental Science, Medicine, Microbiology and Immunology, and Surgery Animal Ethics Committee (Project number 1513489). 10 to 14-week-old female C57BL/6 mice (weighing 23.2±1.7 g, animals under 20 g were not used in this study) were used in all in vivo studies with 3 animals per group. Experiments were conducted without randomization or blinded protocol. Using preliminary peritonitis infection data and a power analysis (using SPSS for Windows, version 12), a sample size 2 would be needed to detect a large effect size (d=0.8) with 95% power using a t test between means with alpha at 0.01. After 1 week of quarantine, inoculation (t=0) was performed by intraperitoneal injection of 300 μL of 2×10$^8$ cells, delivered in MEM, of MDR $A.$ $baumannii$ (FADDI-AB056) with a 25-gauge syringe. Mice received either SNAPP S16 (4.0 or 2.0 mg/kg); imipenem (40 mg/kg) or SNAPP S16 (4.0 mg/kg) with imipenem (40 mg/kg) or or SNAPP S16 (2.0 mg/kg) with imipenem (40 mg/kg) treatment 0.5 h after introduction of the inoculum. An untreated control group was included. At t=16 h, all mice were euthanized and immediately blood was taken from the heart for plating on horse blood agar plates. Colonies were counted and expressed as CFU/mL. The bacterial levels were statistically analyzed using a one-way classification ANOVA and student's t-test (SPSS for Windows, version 12). Data is expressed as mean±standard deviation (SD) of 3 biological replicates.

Figure 10:
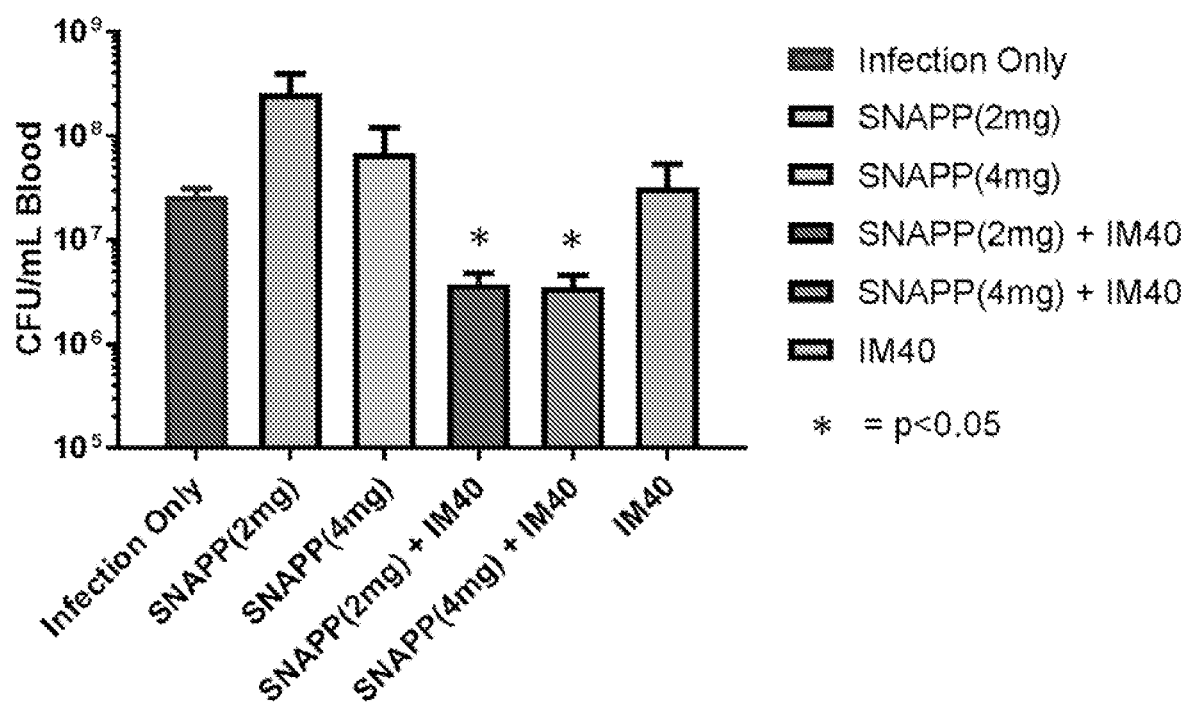
FIG. 10. In vivo synergistic efficacy of SNAPP (S16)+ imipenem in a mouse peritonitis model. Colony forming units (CFU) of CMDR *A. baumannii* (FADDI-AB156) found in the blood of infected mice 16 h after mock (MEM) treatment or treatment with imipenem (40 mg/kg); SNAPP (S16; 4.0 or 2.0 mg/kg) or SNAPP (S16; 4.0 or 2.0 mg/kg)+ imipenem (40 mg/kg). All data are expressed as mean±standard deviation as indicated by the error bars, based on values obtained from at least 3 biological replicates. *P<0.05, Student's t test, significant difference from the mock (MEM) control group.

The synergistic effectiveness of SNAPP S16 and imipenem in vivo was evaluated in a mouse peritonitis model, where the intraperitoneal (i.p.) dose of carbapenem/multidrug resistant (CMDR) $A.$ $baumannii$ (2×10$^8$ CMDR-$A.$ $baumannii$ cells suspended in MEM) which results in the establishment of wide-spread bacterial infection by 16 h (FIG. 10). Thirty minutes after infection mice were injected (i.p.) with a single treatment of SNAPP S16 at two low doses (4.0 or 2.0 mg/kg in MEM) without or with imipenem (40 mg/kg in MEM). Control groups received either MEM (mock treatment, control group) or imipenem (40 mg/kg in MEM). Signs of animal distress were monitored and viable bacteria cell counts (CFU/mL) in blood (bacteraemia) were compared with those of the control group at 16 h (FIG. 10). The doses of 4.0 or 2.0 mg/kg of SNAPP were chosen as these would equate to 0.7 and 0.35× in vitro MBC, respectively, taking into account the average peritoneal/blood volume of mice, and thus would not provide full protection against bacteraemia. Treatment with SNAPP S16 at either the 4.0 or 2.0 mg/kg with imipenem resulted in a significant (p<0.05) 1-log reduction in CMDR-$A.$ $baumannii$ cell counts in blood (FIG. 10) compared to the control groups. The imipenem-treated group or the SNAPP S16 low dose groups did not show any significant difference from the mock-treated group.

Example 7

Synthesis of SNAPPs

This example reports an alternative method for producing SNAPPs. In the examples discussed above, the SNAPPs were prepared through random ring opening polymerisation (ROP) of the cationic capable (?-carboxybenzyl, CBz, Z protected) L-lysine and hydrophobic racemic D,L-valine amino acid N-carboxyanhydride (NCA) monomers. Polymerisation was performed through a core-first approach, initiated by the terminal primary amines of a PAMAM dendrimer core, and conducted at room temperature. However, the inventors have now found that reducing the reaction temperature during polymerisation, to as low as 0° C., can slow down and reduce side reactions in primary amine initiated NCA ROP, resulting in greater "livingness" of the polymers and lead to improved control of polymerisation.

Figure 11:
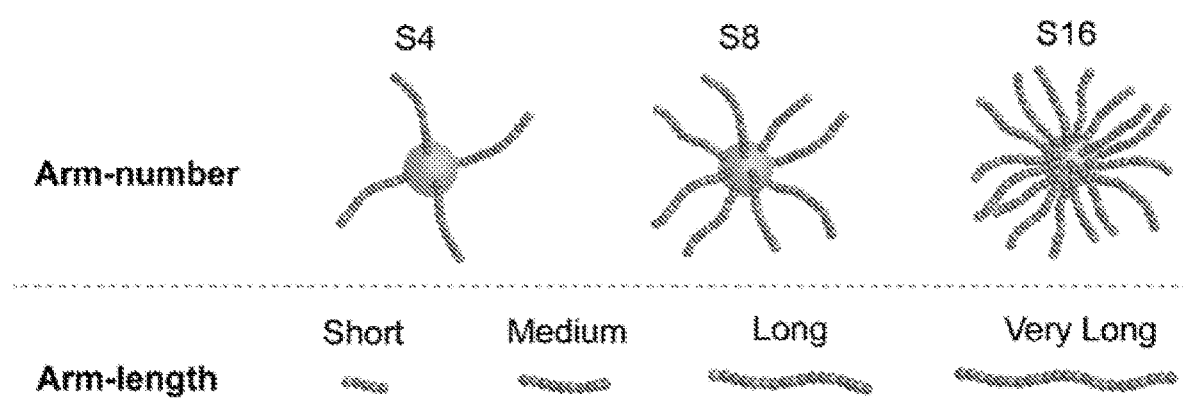
FIG. 11. Scheme illustrating arm number and arm length of star-shaped SNAPPs of Example 7.

FIG. 11 provides an illustration of SNAPPs that were prepared using this alternative method in the form of 4-arm (S4), 8-arm (S8) and 16-arm (S16) stars. Stars of varying arm length were also prepared. Using the core-first approach, NCA monomers were polymerised randomly by primary amine initiation from a PAMAM core under ice (4° C.). The resulting CBz/Z-protected lysine residues were then deprotected with hydrobromic acid (HBr), generating fully water soluble polymers.

Figure 12:
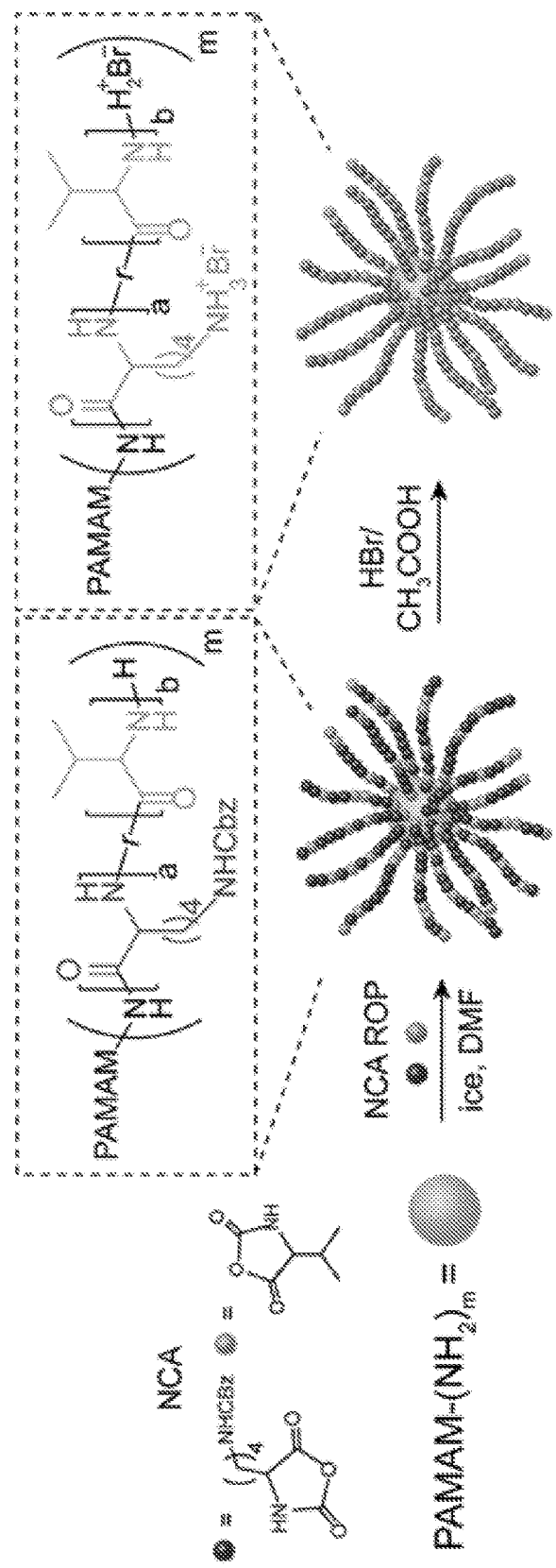
FIG. 12. Scheme illustrating synthesis of SNAPPs of Example 7.

FIG. 12 illustrates the general reaction scheme for the synthesis of lysine and valine SNAPPs in ice through ROP of lysine and valine N-carboxyanhydride (NCAs) monomers by initiation from the terminal amines of poly(amido amine) (PAMAM) dendrimers. First, second and third generation PAMAM dendrimers with 4, 8 and 16 peripheral primary amines respectively were used to prepare S4 (m=4), S8 (m=8) and S16 (m=16) star shaped SNAPPs. Deprotection of lysine CBz group with HBr yielded fully water soluble star SNAPPs.

The methods used to synthesise the NCAs and the SNAPPs, and the method for the subsequent deprotection of the SNAPPs is outlined below.

Synthesis of D,L-Valine and (Z)-L-Lysine N-Carboxyanhydrides (NCAs).

ε-(Z)-L-Lysine and D,L-Valine NCAs were synthesized as per the previous examples, with the inclusion of an additional purification step to remove hydrochloride impurities from the reaction. Dried H-Lys(Z)—OH (2 g, 7.14 mmol) or D,L-Valine (2 g, 17.0 mmol)) were suspended in anhydrous THF (50 mL) in a three-necked round bottomed flask under argon. Triphosgene (lys: 0.85 g, 2.86 mmol, 1.2 equiv. phosgene; val: 2.0 g, 6.74 mmol, 1.2 equiv. phosgene) was then added and the mixture was refluxed at 65° C. for 2 h with continuous stirring. After cooling to room temperature, the reaction mixture was sparged with argon for 45 mins into a sat. NaOH solution, then solvent removed completely in vacuo to a white solid. The solid was then suspected in EtOAc (anhydrous), chilled and placed into a separator funnel where the crude NCA solution was gently washed with chilled saturated brine solution (50 mL), and 0.5% w/v NaHCO$_3$ solution (50 mL). The organic phase was then dried with MgSO4, filtered and concentrated to an oil under low heat, and re-crystalized (×2) from EtOAc (anhydrous) and n-pentane (anhydrous). The resulting crystals were then filtered and washed with n-pentane (dry), then re-precipitated and washed (×2) with dry n-pentane to afford white powder solids (Yields: ~80%) $^1$H NMR (CDCl$_3$): (Z)-L-Lysine NCA $^1$H NMR (400 MHz, CDCl3): $\delta_H$ 1.40-1.60 (m, 4H, NH—CH$_2$—CH$_2$—CH$_2$—CH$_2$—), 1.81-1.94 (m, 2H, NH—CH$_2$—CH$_2$—CH$_2$—CH$_2$—), 3.18 (m, 2H, NH—CH$_2$—CH$_2$—CH$_2$—CH$_2$—), 4.25 (t, 1H, CHN), 4.97 (s, 1H, side chain NH), 5.09 (s, 2H, CH$_2$—ArH), 7.04 (s, 1H, ring NH), 7.3-7.4 (m, 5H, ArH). D,L-Valine NCA $^1$H NMR (400 MHz, CDCl$_3$): $\delta_H$ 1.02 (d, 3H, J=7.0 Hz, CH$_3$), 1.08 (d, 3H, J=7.0 Hz, CH$_3$), 2.25 (m, 1H, CH(CH$_3$)$_2$), 4.22 (d, 1H, J=4.4 Hz, CH-NH), 6.95 (s, 1H, CO—NH).

General procedure for synthesis of (PZLL-r-PVal)$_{arm}$ PAMAM-(NH$_2$)$_{m,core}$ In line with the previous examples, a theoretical lysine-to-valine ratio of approximately 2.5:1 was targeted. To account for different observed reactivity rates of the two monomers, Lys NCA and Val NCA in approximately 2:1 molar ratio were both dissolved in anhydrous DMF ([NCA]$_{total}$=~55 mg/mL) and added via syringe to a test tube containing PAMAM-(NH$_2$)$_m$ (dried) dissolved completely in anhydrous DMSO (volume corresponding to 10% v/v of final reaction volume) under N$_2$. The test tube was then immersed in an ice chest and stirred for 24 h in ice under constant nitrogen flow and with a bleed for CO$_2$ removal (Note: S8$_{VL}$ was stirred for total 50 h). n-butanol (0.86 μL/mg of NCA$_{total}$ added to reaction) was then added to quench remaining NCA monomer and the mixture stirred for a further 1 h. The reaction mixture was then concentrated under vacuum and transferred into diethyl ether to precipitate. The precipitate was then washed thoroughly with ether and dried in vacuo to afford an off-white solid. Average yield ~60%

General Deprotection of (PLL-r-PVal)$_{arm}$ PAMAM-(NH$_2$)$_{m,core}$

Protected star polymer was first fully dissolved in TFA (5 mL/g polymer). 33% HBr in acetic acid was then added (10 mL/g polymer), the reaction mixture stoppered and stirred at room temperature with precipitate forming soon after. After stirring for a total of 2 h at room temperature, the solution was added directly into diethyl ether, washed further in ether (×2) and dried under vacuum. The dried solid was then dissolved up in minimal DI water, transferred to 3.5 kDa dialysis tubing and dialysed against a large volume of DI water (~180 times volume of original dialysis content)(×3) for 24 h. The dialysed solutions were then lyophilised to obtain the deprotected SNAPP as a dried white solid. $^1$H NMR (D$_2$O): $\delta_H$ 0.9 (s, 2(CH$_3$)), 1.3-1.9 (m, NH—CH$_2$—CH$_2$—CH$_2$—CH$_2$—), 2.0 (br s, CH—NH valine), 3.0 (s, NH—CH$_2$—CH$_2$—CH$_2$—CH$_2$—), 4.0-4.15 (s, CH—NH backbone valine), 4.2-4.4 (s, CH—NH backbone lysine).

Characterisation of SNAPPs.

$^1$H NMR analysis was performed using a Varian unity Plus 400 MHz NMR spectrometer using the deuterated solvent as reference. Size exclusion chromatography (SEC) analysis was performed on an aqueous gel permeation chromatography (GPC) units using an eluent of Milli-Q water containing 0.1% v/v trifluoroacetic acid (TFA). The system was operated at a flow rate of 1 mL min$^{-1}$ at 25° C. A Shimadzu Liquid Chromatography system was utilized, equipped with a Shimadzu RID-10 refractometer (A=633 nm) and Wyatt 3-angle light scattering detector, with three Waters Ultrahydrogel columns in series ((i) 250 Å porosity, 6 μm diameter bead size; (ii) and (iii) linear, 10 μm diameter bead size) for separation. The do/dc value of the S4$_M$, S8$_M$, and S16$_M$ SNAPPs were calculated to be 0.187, 0.183, 0.188 respectively at 25° C. using a batch injection protocol and Wyatt ASTRA SEC/LS software. Molecular weight and polydispersity values were calculated on the Wyatt ASTRA SEC/LS software package using Debye modelling with a fit of 2. All GPC samples prepared at a concentration of 5 mg/mL and were filtered through 0.45 μm nylon filters prior to injection. DLS measurements were performed on a Malvern Zetasizer Nano ZS with 4.0 mW HeNe laser operating at 632.8 nm. Analysis was performed at an angle of 173° at a constant temperature of 25±0.01° C. Samples were made to an initial concentration of 1 mg/mL in DMEM (the same media conducted for antibacterial studies) serial dilutions performed until stable spectra was obtained. Measurements were performed in triplicate. All samples filtered through 0.45 μm nylon filters to measurement.

All SNAPPs produced and characterised in this Example and shown in Table 6 displayed potent antimicrobial activity against both Gram-positive and Gram-negative bacteria and only exhibited some cytotoxicity against mammalian cells at high concentrations indicating a large therapeutic index (data not shown).

Tables

TABLE 1

Evaluation of the Absence/Presence of Synergy between S16 and a Range of Antibiotics

| | | MBC in combination (μM) | | Synergistic? (Yes/No) | |
|---|---|---|---|---|---|
| | Antibiotics | | S16 | Bliss* | HAS* |
| E. coli | Amp | 5.7 | 0.4 | No | No |
| | Gen | 2.2 | | Yes | Yes |
| | Ag$^+$ | 1.8 | | Yes | Yes |
| K. pneumoniae | Amp | 327.6 | 0.8 | Yes | Yes |
| | Gen | 1.1 | | Yes | Yes |
| | Ag$^+$ | 5.3 | | Yes | Yes |
| P. aeruginosa | Amp | 2930.7 | 0.7 | Yes | Yes |
| | Gen | 1.2 | | No | No |
| | Ag$^+$ | 0.5 | | Yes | Yes |
| | Dox | 25.3 | | Yes | Yes |
| | Tob | 1.9 | | No | No |
| CMDR | Ag$^+$ | 11.8 | 0.7 | Yes | Yes |
| P. aeruginosa | Dox | 295.3 | | Yes | Yes |
| | Tob | 119.7 | | No | No |
| A. baumannii | Amp | 1465.4 | 0.4 | No | No |
| | Gen | 6.0 | | Yes | No |
| | Ag$^+$ | 4.1 | | Yes | Yes |
| | Imi | 19.0 | | Yes | Yes |
| | Tob | 7.6 | | No | No |

TABLE 1-continued

Evaluation of the Absence/Presence of Synergy between S16 and a Range of Antibiotics

| | | MBC in combination (μM) | | Synergistic? (Yes/No) | |
|---|---|---|---|---|---|
| | | Antibiotics | S16 | Bliss* | HAS* |
| CMDR A. baumannii | Amp | 2930.7 | 0.8 | Yes | Yes |
| | Ag$^+$ | 2.9 | | Yes | Yes |
| | Imi | 177.4 | | Yes | Yes |
| | Tob | 2190.3 | | No | No |

TABLE 2

Fold Reduction of MBC Provided by Synergistic S16-Antibiotic Combinations

| | | MBC in combination, MBC$_{eff}$ (μM) | | Fold reduction of MBC |
|---|---|---|---|---|
| | | Antibiotics | S16 | |
| P. aeruginosa | Amp | 366.3$^a$ | 0.7$^b$ | >16 (99.9% reduction) |
| CMDR P. aeruginosa | Ag$^+$ | 5.9$^a$ | 0.7$^b$ | 6.5 |
| | Dox | 148.2$^a$ | | 4.2 |
| CMDR A. baumannii | Ag$^+$ | 2.9$^a$ | 0.8$^b$ | 3.7 |
| | Imi | 88.2$^a$ | | 4.0 |

$^a$The MBC$_{eff}$ values for the antibiotics were taken as the antibiotic concentrations that resulted in at least a 2-log reduction in CFU/mL when co-administered with S16.
$^b$The MBC$_{eff}$ of S16 is equivalent to its MBC50.

TABLE 3

Minimum Bactericidal Concentrations (MBCs) of S16 and Antibiotics

| | | MBC (μM) | | | | | |
|---|---|---|---|---|---|---|---|
| | | E. coli | K. pneumoniae | P. aeruginosa | CMDR P. aeruginosa | A. baumannii | CMDR A. baumannii |
| Antimicrobial | S16 | 0.7 | 1.5 | 1.4 | 1.4 | 0.9 | 1.6 |
| | Ag$^+$ | 3.5 | 10.6 | 1.2 | 38.3 | 8.2 | 10.6 |
| | Amp | 9.4 | 655.1 | >5860.0 | <1.4 | >2930.7 | >2930.7 |
| | Gen | 3.7 | 2.2 | 2.4 | <1.1 | 12.1 | >1104.5 |
| | Tob | NT$^a$ | NT$^a$ | 3.9 | 239.4 | 15.2 | >2190.3 |
| | Dox | NT$^a$ | NT$^a$ | 50.7 | 629.7 | NT$^a$ | NT$^a$ |
| | Imi | NT$^a$ | NT$^a$ | NT$^a$ | NT$^a$ | 37.8 | 354.8 |

$^a$NT = Not tested.

TABLE 4

Antibiogram of CMDR P. aeruginosa (FADDI-PA067)

| Antibiotic | Susceptibility$^a$ |
|---|---|
| Aztreonam | Resistant |
| Ceftazidime | Resistant |
| Ciprofloxacin | Sensitive |
| Gentamicin | Resistant |
| Piperacillin | Resistant |
| Ticarcillin | Resistant |
| Tobramycin | Resistant |
| Colistin Sulfate | Resistant (>110.8 μM) |

$^a$Susceptibility of the bacteria species towards a particular antibiotic is interpreted based on resistant breakpoints provided by the Clinical and Laboratory Standards Institute.

TABLE 5

Antibiogram of CMDR A. baumannii (FADDI-AB156)

| Antibiotic | MIC (μM) | Susceptibility$^a$ |
|---|---|---|
| Amikacin | ≥109.3 | Resistant |
| Ampicillin | >2930.7 | Resistant |
| Amoxicillin/Clavulanic Acid | ≥87.6 | Resistant |
| Cefazolin | ≥140.8 | Resistant |
| Cefepime | ≥133.2 | Resistant |
| Cefoxitin | ≥149.7 | Resistant |
| Ceftazidime | ≥117.1 | Resistant |
| Ceftriaxone | ≥115.4 | Resistant |
| Ciprofloxacin | ≥12.1 | Resistant |
| Gentamicin | >1104.5 | Resistant |
| Meropenem | ≥41.7 | Resistant |
| Nalidixic Acid | ≥137.8 | Resistant |
| Nitrofurantoin | ≥2149.8 | Resistant |
| Norfloxacin | ≥50.1 | Resistant |
| Piperacillin/Tazobactam | ≥247.3 | Resistant |
| Ticarcillin/Clavulanic Aid | ≥333.0 | Resistant |
| Tobramycin | >2190.3 | Resistant |
| Trimethoprim | ≥55.1 | Resistant |
| Trimethoprim/Sulfamethoxazole | ≥1102.2 | Resistant |
| Imipenem | 354.8 | Resistant |
| Colistin Sulfate | 13.8 | Resistant |

$^a$Susceptibility of the bacteria species towards a particular antibiotic is interpreted based on resistant breakpoints provided by the Clinical and Laboratory Standards Institute (Clinical and Laboratory Standards Institute. M100-S24: Performance Standards for Antimicrobial Susceptibility Testing; Twenty-Fourth Informational Supplement. Clinical and Laboratory Standards Institute (2014)).

TABLE 6

Characterisation of SNAPPs synthesised in Example 7.

| SNAPP code | Arm number | Lys/Val$^a$ | $M_n$ (kDa)$^b$ | Đ$^b$ | Arm DP | $D_h$ (nm)$^c$ |
|---|---|---|---|---|---|---|
| S4$_S$ | 4 | 2.1 | 3.3 | 1.3 | 5 | 1.0 ± 0.4 |
| S4$_M$ | 4 | 2.3 | 8.8 | 1.3 | 12 | 4.4 ± 0.7 |
| S4$_L$ | 4 | 2.5 | 14.1 | 1.5 | 18 | 5.6 ± 0.7 |
| S4$_{VL}$ | 4 | 2.8 | 19.2 | 1.7 | 26 | 6.6 ± 0.5 |
| S8$_M$ | 8 | 2.4 | 23.4 | 1.5 | 15 | 7.9 ± 1.2 |
| S8$_{VL}$ | 8 | 2.6 | 43.4 | 1.8 | 29 | 12.2 ± 0.6 |
| S16$_M$ | 16 | 2.5 | 41.1 | 1.7 | 14 | 9.4 ± 0.5 |

Subscript values represent star arm length (S = small, M = medium, L = long, VL = very long).
$^a$Determined through $^1$H NMR analysis in D$_2$O.
$^b$Absolute number-average molecular weight ($M_n$) and dispersity index (PDI) determined through SEC light scattering using measured dn/dc values.
$^c$Hydrodynamic diameters and standard deviations of SNAPPs determined by DLS. Values represent number distributions in DMEM at concentrations <1 mg/ml. Values represent an average of 3 sets containing 15 measurements per set.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of sensitizing bacteria to an anti-bacterial compound, the method comprising contacting the bacteria with a star shaped peptide polymer, thereby sensitizing the bacteria to an anti-bacterial compound, wherein the star shaped peptide polymer comprises a multifunctional core with a plurality of terminal arms extending therefrom, wherein the terminal arms are random peptide copolymers of at least a cationic amino acid residue and a hydrophobic amino acid residue arranged as follows:

([Cationic Amino Acid]$_a$–ran–[Hydrophobic Amino Acid]$_b$)$_m$ wherein 'm' represents the number of terminal arms and is $2^n$, wherein n is a number including or between 2 and 8, 'a' and 'b' represent the number of repeat units of the amino acids in the peptide copolymer respectively and 'ran' refers to the random copolymerisation of the amino acids; and wherein the copolymer has a molar ratio of cationic amino acid residue to hydrophobic amino acid residue of from about 1.5:1 to about 3.5:1.

2. A method according to claim 1, further comprising the step of contacting the bacteria with the anti-bacterial compound for which the bacteria has been sensitized to.

3. The method of claim 1, wherein the bacteria are present in or on a subject and wherein the method thereby treats a bacterial infection in the subject.

4. A method of claim 1, wherein the bacteria are present in or on a subject and wherein subject has antibiotic hypersensitivity.

5. A method according to claim 1, wherein the antibacterial compound is selected from the group consisting of:
 (1) Macrolides or ketolides such as erythromycin, azithromycin, clarithromycin and telithromycin;
 (2) Beta (β)-lactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefinetazole, cefotaxime, ceftizoxime, ceftriaxone, cefoperazone, ceftazidime, cefixime, cefpodoxime, ceftibuten, cefdinir, cefpirome, cefepime, aztreonam, imipenem, meropenem, ertapenem, doripenem, ceftobiprole, and ceftaroline;
 (3) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, garenoxacin, gemifloxacin and pazufloxacin;
 (4) Antibacterial sulfonanmides and antibacterial sulphanilamides, including para-aminobenzoic acid, sulfadiazine, sulfisoxazole, sulfamethoxazole and sulfathalidine;
 (5) Aminoglycosides such as streptomycin, neomycin, kanamycin, paromycin, gentamicin, tobramycin, amikacin, netilmicin, spectinomycin, sisomicin, dibekacin and isepamicin;
 (6) Tetracyclines such as tetracycline, chlortetracycline, demeclocycline, minocycline, oxytetracycline, methacycline, tigecycline, doxycycline;
 (7) Rifamycins such as rifampicin (also called rifampin), rifapentine, rifabutin, bezoxazinorifamycin and rifaximin;
 (8) Lincosamides such as lincomycin and clindamycin;
 (9) Glycopeptides such as telavancin, vancomycin and teicoplanin or lipopeptides such as daptomycin;
 (10) Streptogramins such as quinupristin and daflopristin;
 (11) Oxazolidinones such as linezolid;
 (12) Polymyxin, colistin and colymycin; and
 (13) Trimethoprim and bacitracin.

6. A method according to claim 1, wherein prior to sensitizing, the bacteria exhibited resistance to any one or more of the antibacterial compounds listed in claim 5.

7. A method according to claim 1, wherein the bacteria comprise, consist essentially of or consist of Gram-negative bacteria.

8. A method according to claim 1, wherein the bacteria comprise, consist essentially of or consist of Gram-positive bacteria.

9. A method according to claim 1, wherein the antibacterial compound is a β-lactam, an aminoglycoside or silver.

10. A method for treating a bacterial infection in a subject caused by, or including, *Escherichia coli*, *Klebsiella pneumoniae*, *P. aeruginosa*, and/or *A. baumannii*, the method comprising administering to the subject a star shaped peptide polymer and an antibacterial compound, thereby treating the bacterial infection in the subject, wherein the star shaped peptide polymer comprises a multifunctional core with a plurality of terminal arms extending therefrom, wherein the terminal arms are random peptide copolymers of at least a cationic amino acid residue and a hydrophobic amino acid residue arranged as follow:

([Cationic Amino Acid]$_a$–ran–[Hydrophobic Amino Acid]$_b$)$_m$ wherein 'm' represents the number of terminal arms and is $2^n$, wherein n is a number including or between 2 and 8, 'a' and 'b' represent the number of repeat units of the amino acids in the peptide copolymer respectively, and 'ran' refers to the random copolymerisation of the amino acids; and wherein the copolymer has a molar ratio of cationic amino acid residue to hydrophobic amino acid residue of from about 1.5:1 to about 3.5:1.

11. A method according to claim 10, wherein the *A. baumannii* present in the infection exhibits resistance to any one or more of Amikacin, Ampicillin, Amoxicillin/Clavulanic Acid, Cefazolin, Cefepime, Cefoxitin, Ceftazidime, Ceftriaxone, Ciprofloxacin, Gentamicin, Meropenem, Nalidixic Acid, Nitrofurantoin, Norfloxacin, Piperacillin/Tazobactam, Ticarcillin/Clavulanic Aid, Tobramycin, Trimethoprim, Trimethoprim/Sulfamethoxazole, Imipenem and Colistin Sulfate.

12. A method according to claim 10, wherein the *P. aeruginosa* present in the infection exhibits resistance to any one or more of Ampicillin, Aztreonam, Ceftazidime, Gentamicin, Piperacillin, Ticarcillin, Tobramycin and Colistin Sulfate.

13. A method according to claim 1, wherein the bacteria are in or on a subject, resulting in a bacterial infection in the subject and wherein the star shaped peptide polymer is administered directly to the site of infection.

14. A method according to claim 1, wherein the copolymer has a molar ratio of cationic amino acid residue to hydrophobic amino acid residue of from about 1.8:1 to about 3:1.

15. A method according to claim 1, wherein the cationic amino acid residue is a lysine residue, and the hydrophobic amino acid residue is a valine residue.

16. A method according to claim 1, wherein the copolymer exhibits a degree of polymerisation of at least 10 and up to 50.

17. A method according to claim 1, wherein the multifunctional core comprises a dendrimer, wherein the dendrimer has a centre in the form of a diamine core, wherein the diamine core is of the form $R^1_2N\text{-}(C_2\text{-}C_6 \text{ alkyl})\text{-}NR^1_2$, where each $R^1$ represents a covalent bond to a separate dendron arm.

18. A method according to claim 1, wherein the multifunctional core includes a number of terminal arms of from at least 4 and up to 256 terminal arms.

19. A method according to claim 18, wherein the number of terminal arms is from at least 4 and up to 64.

20. A method according to claim 1, wherein the star shaped peptide polymer is selected from:

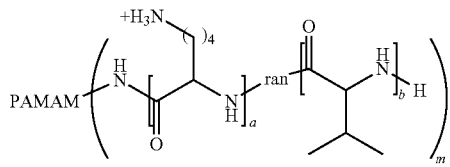

wherein 'm' represents the number of terminal arms and is $2^n$, wherein n is a number including or between 2 and 8, 'a' and 'b' represent the number of repeat units of the lysine and valine respectively, and 'ran' refers to the random copolymerisation of the lysine and valine.

21. A method according to claim 1, wherein n is 4 or 5, and m is 16 or 32 accordingly.

22. A method according to claim 10, wherein n is 4 or 5, and m is 16 or 32 accordingly.

23. A method according to claim 9, wherein the silver is silver nitrate.

24. A method according to claim 10, wherein the multifunctional core is a dendrimer and the dendrimer has a centre in the form of a diamine core, wherein the diamine core is of the form $R^1_2N\text{-}(C_2\text{-}C_6 \text{ alkyl})\text{-}NR^1_2$, where each $R^1$ represents a covalent bond to a separate dendron arm.

25. A method according to claim 10, wherein the star shaped peptide polymer is selected from:

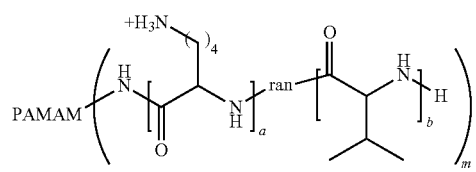

wherein 'm' represents the number of terminal arms and is $2^n$, wherein n is a number including or between 2 and 8, 'a' and 'b' represent the number of repeat units of lysine and valine in the peptide copolymer respectively and 'ran' refers to the random copolymerisation of the lysine and valine.

26. A method according to claim 10, wherein the copolymer has a molar ratio of cationic amino acid residue to hydrophobic amino acid residue of from about 1.8:1 to about 3:1.

* * * * *

UNITED STATES PATENT AND TRADEMARK OFFICE
CERTIFICATE OF CORRECTION

PATENT NO. : 11,154,589 B2  
APPLICATION NO. : 16/343556  
DATED : October 26, 2021  
INVENTOR(S) : Greg GuangHua Qiao et al.

It is certified that error appears in the above-identified patent and that said Letters Patent is hereby corrected as shown below:

On the Title Page

Column 2 (item (56), OTHER PUBLICATIONS), Line 1, delete "Infectionsm" and replace with -- Infections --.

In the Claims

Column 47, Lines 46-47, Claim 5, delete "cepalothin," and replace with -- cephalothin, --.

Column 47, Line 49, Claim 5, delete "cefinetazole," and replace with -- cefmetazole, --.

Column 47, Line 60, Claim 5, delete "sulfonanmides" and replace with -- sulfonamides --.

Column 47, Line 65, Claim 5, delete "paromycin," and replace with -- paromomycin, --.

Column 48, Line 10, Claim 5, delete "daflopristin;" and replace with -- dalfopristin; --.

Signed and Sealed this  
Eighth Day of February, 2022

Drew Hirshfeld  
*Performing the Functions and Duties of the*  
*Under Secretary of Commerce for Intellectual Property and*  
*Director of the United States Patent and Trademark Office*